US008765431B2

(12) United States Patent
Sherman et al.

(10) Patent No.: US 8,765,431 B2
(45) Date of Patent: Jul. 1, 2014

(54) METHOD FOR ENZYMATIC PRODUCTION OF DECARBOXYLATED POLYKETIDES AND FATTY ACIDS

(75) Inventors: David H. Sherman, Ann Arbor, MI (US); Janet L. Smith, Ann Arbor, MI (US); Liangcai Gu, Boston, MA (US); Jennifer Gehret, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 223 days.

(21) Appl. No.: 12/842,549

(22) Filed: Jul. 23, 2010

(65) Prior Publication Data
US 2011/0091952 A1  Apr. 21, 2011

Related U.S. Application Data

(60) Provisional application No. 61/227,987, filed on Jul. 23, 2009.

(51) Int. Cl.
*C12P 5/00* (2006.01)
*C12N 9/10* (2006.01)
*C12N 9/16* (2006.01)
*C07H 21/04* (2006.01)
*C07K 1/00* (2006.01)

(52) U.S. Cl.
USPC .......... 435/166; 435/193; 435/196; 536/23.2; 530/350

(58) Field of Classification Search
USPC ........... 435/166, 193, 196; 536/23.2; 530/350
See application file for complete search history.

(56) References Cited

U.S. PATENT DOCUMENTS

| RE30,985 | E  | 6/1982  | Cartaya |
| 4,419,446 | A  | 12/1983 | Howley et al. |
| 4,560,655 | A  | 12/1985 | Baker |
| 4,601,978 | A  | 7/1986  | Karin |
| 4,657,866 | A  | 4/1987  | Kumar |
| 4,767,704 | A  | 8/1988  | Cleveland et al. |
| 4,816,567 | A  | 3/1989  | Cabilly et al. |
| 4,927,762 | A  | 5/1990  | Darfler |
| 4,946,778 | A  | 8/1990  | Ladner et al. |
| 4,965,199 | A  | 10/1990 | Capon et al. |
| 5,122,469 | A  | 6/1992  | Mather et al. |
| 2006/0240528 | A1 | 10/2006 | Leadlay et al. |

FOREIGN PATENT DOCUMENTS

| EP | 73657 A1 | 3/1983 |
| EP | 244234 A2 | 11/1987 |
| EP | 402226 A1 | 12/1990 |
| WO | WO-87/00195 A1 | 1/1987 |
| WO | WO-94/11026 A2 | 5/1994 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Akey et al., Crystal structures of dehydratase domains from the curacin polyketide biosynthetic pathway, *Structure*, 18:94-105 (2010).
Akey et al., Structural basis for macrolactonization by the pikromycin thioesterase, *Nat. Chem. Biol.*, 2:537-42 (2006).
Anzalone et al., Bismuth compounds in organic synthesis. A one-pot synthesis of homoallyl ethers and homoallyl acetates from aldehydes catalyzed by bismuth triflate, *J. Org. Chem.*, 70:2091-6 (2005).
Barnes et al., Methods for growth of cultured cells in serum-free medium, *Anal. Biochem.*, 102:255-70 (1980).
Better et al., Production and scale up of chimeric Fab fragments from bacteria, IN: *Advances in Gene Technology: The Molecular Biology of Immune Diseases and the Immune Response*, ICSU Short Reports, 10:105 (1990).
Better et al., *Escherichia coli* secretion of an active chimeric antibody fragment, *Science*, 240: 1041-3 (1988).
Better et al., Potent anti-CD5 ricin A chain immunoconjugates from bacterially produced Fab' and F(ab')2, *Proc. Natl. Acad. Sci. USA*, 90:457-61 (1993).
Bonanno et al., Structural genomics of enzymes involved in sterol/isoprenoid biosynthesis, *Proc. Natl. Acad. Sci. USA*, 98:12896-901 (2001).
Caffrey, The stereochemistry of ketoreduction, *Chem. Biol.*, 12:1060-2 (2005).
Calderone et al., Convergence of isoprene and polyketide biosynthetic machinery: isoprenyl-S-carrier proteins in the pksX pathway of *Bacillus subtilis*, *Proc. Natl. Acad. Sci. USA*, 103:8977-82 (2006).
Calderone et al., Incorporation of nonmethyl branches by isoprenoid-like logic: multiple beta-alkylation events in the biosynthesis of myxovirescin A1, *Chem. Biol.*, 14:835-46 (2007).

(Continued)

*Primary Examiner* — Ganapathirama Raghu
(74) *Attorney, Agent, or Firm* — Marshall, Gerstein & Borun LLP

(57) ABSTRACT

Disclosed herein are methods of preparing alkenes from beta-hydroxy or beta-sulfate carboxylic acid or carboxylic acid derivatives using thioesterase and optionally a sulfotransferase.

19 Claims, 16 Drawing Sheets

(56) References Cited

OTHER PUBLICATIONS

Carter et al., High level *Escherichia coli* expression and production of a bivalent humanized antibody fragment, *Biotechnology (NY)*, 10:163-7 (1992).

Chang et al., Biosynthetic pathway and gene cluster analysis of curacin A, an antitubulin natural product from the tropical marine cyanobacterium *Lyngbya majuscula*, *J. Nat. Prod.*, 67:1356-67 (2004).

Chang et al., The barbamide biosynthetic gene cluster: a novel marine cyanobacterial system of mixed polyketide synthase (PKS)-nonribosomal peptide synthetase (NRPS) origin involving an unusual trichloroleucyl starter unit, *Gene*, 296:235-47 (2002).

Chapman et al., Sulfotransferases: structure, mechanism, biological activity, inhibition, and synthetic utility, *Angew. Chem. Int. Ed. Engl.*, 43:3526-48 (2004).

Choi et al., Isolation of the biosynthetic gene cluster for tautomycetin, a linear polyketide T cell-specific immunomodulator from *Streptomyces* sp. CK4412, *Microbiology*, 153:1095-102 (2007).

Clackson et al., Making antibody fragments using phage display libraries, *Nature*, 352:624-8 (1991).

Collaborative Computation Project, No. 4, The CCP4 suite: programs for protein crystallography, *Acta Crystallogr. D Biol. Crystallogr.*, 50:760-3 (1994).

Delano, The PyMOL molecular graphics system, 11 slides, circa 2000, Accessed on the Internet at: http://pymol.sourceforge.net/overview/sId001.htm.

Delproposto et al., Mocr: a novel fusion tag for enhancing solubility that is compatible with structural biology applications, *Protein Expr. Purif.*, 63:40-9 (2009).

Donnelly et al., An expression vector tailored for large-scale, high-throughput purification of recombinant proteins, *Protein Expr. Purif.*, 47:446-54 (2006).

Dorrestein et al., Facile detection of acyl and peptidyl intermediates on thiotemplate carrier domains via phosphopantetheinyl elimination reactions during tandem mass spectrometry, *Biochemistry*, 45:12756-66 (2006).

Emsley et al., Coot: model-building tools for molecular graphics, *Acta Crystallogr. D Biol. Crystallogr.*, 60:2126-32 (2004).

Fischbach et al., Assembly-line enzymology for polyketide and nonribosomal Peptide antibiotics: logic, machinery, and mechanisms, *Chem. Rev.*, 106:3468-96 (2006).

Fischbach et al., The evolution of gene collectives: How natural selection drives chemical innovation, *Proc. Natl. Acad. Sci. USA*, 105:4601-8 (2008).

Fischetti et al., Mini-beam collimator enables microcrystallography experiments on standard beamlines, *J. Synchrotron Radiat.*, 16:217-25 (2009).

Fleer et al., Stable multicopy vectors for high-level secretion of recombinant human serum albumin by *Kluyveromyces* yeasts, *Biotechnology (NY)*, 9:968-75 (1991).

Geders et al., Crystal structure of the ECH2 catalytic domain of CurF from *Lyngbya majuscula*. Insights into a decarboxylase involved in polyketide chain beta-branching, *J. Biol. Chem.*, 282:35954-63 (2007).

Geysen et al., Use of peptide synthesis to probe viral antigens for epitopes to a resolution of a single amino acid., *Proc. Natl. Acad. Sci. USA*, 81:3998-4002 (1984).

Giraldes et al., Structural and mechanistic insights into polyketide macrolactonization from polyketide-based affinity labels, *Nat. Chem. Biol.*, 2:531-6 (2006).

Graham et al., Characteristics of a human cell line transformed by DNA from human adenovirus type 5, *J. Gen. Virol.*, 36:59-74 (1977).

Gu et al., GNAT-like strategy for polyketide chain initiation, *Science*, 318:970-4 (2007).

Gu et al., Metabolic coupling of dehydration and decarboxylation in the curacin A pathway: functional identification of a mechanistically diverse enzyme pair, *J. Am. Chem. Soc.*, 128:9014-5 (2006).

Gu et al., Metamorphic enzyme assembly in polyketide diversification, *Nature*, 459:731-5 (2009).

Gu et al., Polyketide decarboxylative chain termination preceded by o-sulfonation in curacin a biosynthesis, *J. Am. Chem. Soc.*, 131:16033-5 (2009).

Ham et al., Media and growth requirements, *Methods Enzymol.*, 58:44-93 (1979).

Jones, Proteinase mutants of *Saccharomyces cerevisiae*, *Genetics*, 85:23-33 (1977).

Khosla et al., Structure and mechanism of the 6-deoxyerythronolide B synthase, *Annu. Rev. Biochem.*, 76:195-221 (2007).

Kohler et al., Continuous cultures of fused cells secreting antibody of predefined specificity, *Nature*, 256:495-7 (1975).

Kozbor et al., The production of monoclonal antibodies from human lymphocytes, *Immunology Today*, 4:72-9 (1983).

Ledford et al., Space charge effects in Fourier transform mass spectrometry. Mass calibration, *Anal. Chem.*, 56:2744-8 (1984).

Marks et al., By-passing immunization. Human antibodies from V-gene libraries displayed on phage, *J. Mol. Biol.*, 222:581-97 (1991).

Mather et al., Culture of testicular cells in hormone-supplemented serum-free medium, *Ann. NY Acad. Sci.*, 383:44-68 (1982).

Mather, Establishment and characterization of two distinct mouse testicular epithelial cell lines, *Biol. Reprod.*, 23:243-51 (1980).

Morrison et al., Chimeric human antibody molecules: mouse antigen-binding domains with human constant region domains, *Proc. Natl. Acad. Sci. USA*, 81:6851-5 (1984).

Murshudov et al., Refinement of macromolecular structures by the maximum-likelihood method, *Acta Crystallogr. D Biol. Crystallogr.*, 53:240-55 (1997).

Nelson et al., Catalytic asymmetric acyl halide—aldehyde cyclocondensations. A strategy for enantioselective catalyzed cross aldol reaction, J. Am. Chem. Soc., 121:9742-3 (1999).

Neuberger et al., Recombinant antibodies possessing novel effector functions, *Nature*, 312:604-8 (1984).

Otwinowski, Processing of X-ray Diffraction Data Collected in Oscillation Mode Methods in Enzymology, 276:307-26 (1997).

Painter et al., Optimal description of a protein structure in terms of multiple groups undergoing TLS motion, *Acta Crystallogr. D Biol. Crystallogr.*, 62:439-50 (2006).

Roongsawang et al., In vivo characterization of tandem C-terminal thioesterase domains in arthrofactin synthetase, *Chembiochem.*, 8:501-12 (2007).

Sanchez et al., Cloning and characterization of a phosphopantetheinyl transferase from *Streptomyces verticillus* ATCC15003, the producer of the hybrid peptide-polyketide antitumor drug bleomycin, *Chem. Biol.*, 8:725-38 (2001).

Schuttelkopf et al., PRODRG: a tool for high-throughput crystallography of protein-ligand complexes, *Acta Crystallogr. D Biol. Crystallogr.*, 60:1355-63 (2004).

Senko et al., A high-performance modular data system for Fourier transform ion cyclotron resonance mass spectrometry, *Rapid Commun. Mass Spectrom.*, 10:1839-44 (1996).

Spafford et al., Iron(III) p-toluenesulfonate catalyzed synthesis of homoallyl ethers from acetals and Idehydes, *Tetrahedron Lett.*, 48:8665-7 (2007).

Stinchcomb et al., Isolation and characterisation of a yeast chromosomal replicator, *Nature*, 282:39-43 (1979).

Strehmel et al., Synthesis of 4-sulfonatooxy-2,2,6,6-tetramethylpiperidine-1-yloxyl derivatives for investigation of ionic liquids, *Tetrahedron Lett.*, 49:586-8 (2008).

Takeda et al., Construction of chimaeric processed immunoglobulin genes containing mouse variable and human constant region sequences, *Nature*, 314:452-4 (1985).

Terwilliger et al., Automated MAD and MIR structure solution, *Acta Crystallogr. D BBiol. Crystallogr.*, 55:849-61 (1999).

Terwilliger, Automated main-chain model building by template matching and iterative fragment extension, *Acta Crystallogr. D Biol. Crystallogr.*, 59:38-44 (2003).

Terwilliger, Maximum-likelihood density modification, *Acta Crystallogr. D Biol. Crystallogr.*, 56:965-72 (2000).

Thompson et al., Multiple sequence alignment using ClustalW and ClustalX, *Curr. Protoc. Bioinformatics*, Chapter 2, Unit 2 3 (2002).

(56) References Cited

OTHER PUBLICATIONS

Tsai et al., Crystal structure of the macrocycle-forming thioesterase domain of the erythromycin polyketide synthase: versatility from a unique substrate channel, *Proc. Natl. Acad. Sci. USA*, 98:14808-13 (2001).

Urlaub et al., Isolation of Chinese hamster cell mutants deficient in dihydrofolate reductase activity, *Proc. Natl. Acad. Sci. USA*, 77:4216-20 (1980).

Van Den Berg et al., Kluyveromyces as a host for heterologous gene expression: expression and secretion of prochymosin, *Biotechnology (NY)*, 8:135-9 (1990).

Verdier-Pinard et al., Structure-activity analysis of the interaction of curacin A, the potent colchicine site antimitotic agent, with tubulin and effects of analogs on the growth of MCF-7 breast cancer cells, *Mol. Pharmacol.*, 53:62-76 (1998).

Walsh, Polyketide and nonribosomal peptide antibiotics: modularity and versatility, *Science*, 303:1805-10 (2004).

Walsh, The chemical versatility of natural-product assembly lines, *Acc. Chem. Res.*, 41:4-10 (2008).

Yaniv, Enhancing elements for activation of eukaryotic promoters, *Nature*, 297:17-8 (1982).

Chuck et al., Molecular recognition of diketide substrates by a β-ketoacyl-acyl carrier protein synthase domain within a bimodular polyketide synthase, Chem. Biol., 4(10):757-66 (1997).

Kumar et al., A thioesterase for chemoselective hydrolysis of S-actyl sulfanylalkanoates, Org. Lett., 3(2):283-5 (2001).

International Search Report and Written Opinion from corresponding International application No. PCT/US2010/043057, mailing date Mar. 14, 2011.

International Preliminary Report on Patentability for corresponding International application No. PCT/US2010/043057, dated Jan. 24, 2012.

\* cited by examiner

```
CurM              1505  QAAPITERQDILKNYIQLVVAKTLGINPSKISTDDNFVELGMDSLMGMEVVNKLSGDLDF
CyanothecePCC7424       ----PQRTEVLITYLQSSIARILHLSPADISPSDSLVDLGMDSLMVMEAINTLKKDLQL
CyanothecePCC7822       -ALSPEQRTEALTAYLQSAMAQIMQLSPSQISGEDSLLDIGMDSLMIMEAINQLKRDLQL
Synechococcus           INLEASQRADYLLDYLRRSVAQILKLEIEQIQSHDSLLDLGMDSLMIMEAIASLKQDLQL
Haliangium              --------------EHLVELLNLEPEAVTRDAELAALGLDSMLSLELGEAIRDELEL
Pseudomonas             --------------EAREHALQDYLLGLFRAAATVATESLDVSASIEAWGLDSLVLMEILKTVRMDLGL
                                          *  *** : *   ::  : *

CurM                    IIYPREFYERPTIDSLTQYLSAELSE----------DNLATQPSPTS-LEIFATKSSPSGNS
CyanothecePCC7424       MLYPREIYEHPKIEALATYLGTEFEG----------THGQSPKSPQHNPQKQELVVSRFSKT
CyanothecePCC7822       MLYPREIYQHPKIEALANYLAAEFER----------THG---KGQIPVTSKQELVVSRLITIA
Synechococcus           MLYPREIYERPRLDVLTAYLAAEFTK----------AHDSEAATAAAAIPSQSLSVKTKKQW
Haliangium              TVYPRELAEIRTLAELETLLGRLADERVSLQARPAAAPHDAEPELGAPLEPELESPLGPE
Pseudomonas             IIYPREMYTHSTLSQFAHYLAGQLRAG----------NDEPLAGGDSRQRHEDYLSPLADLA
                         :****:        :          *

CurM                    ARPASVSSRLPGIIFILSSPRSGSTLLRVMLAGHSSLFSPPELHLLIPFNTMKERQEQLNL
CyanothecePCC7424       YQPLTITKKLPGIIFILSSPRAGSTLLRVMFAGHPDLISPPELHLLPFNTMGQRDQELAL
CyanothecePCC7822       NQPLTITKKLPGILFILSSPRAGSTLLRVMLAGHPDLASPPELHLLPFNSMGQRNQELAL
Synechococcus           QKPD--HKNPNPIAFILSSPRSGSTLLRVMLAGHPGLYSPPELHLLPFETMGDRHQELGL
Haliangium              GERLRGAPLREGPVFVLSAPRSGSTLLRVMLAGHSRLFAPPELHLLVAADLAAWRD--SP
Pseudomonas             GVVQDVADRVPGVAFILSSPRSGSTLLRAMLQGHDQVFAPPELHLLGYTSLAQWHEATKE
                             *   .:.  *****.*.:  **    ..    *******

CurM                    SYLGEGLQKTFMEVKNLDATASQALIKDLESQNLSIQQVYGMLQENIAPRLLVDKSPTYA
CyanothecePCC7424       SYLGEGLQRAFMELGGLDSQTSQSLIEELIHQNTSIPDVYQRLQELAGNRLLVDKSPTYG
CyanothecePCC7822       SYLGEGLQRAFMDLQGLDSATSQQLIERLIAEDISIPDVYEMLQQSAGKRLLVDKSPTYG
Synechococcus           SHLGEGLQRALMDLENLTPEASQAKVNQWVKANTPIADIYAYLQRQAEQRLLIDKSPSYG
Haliangium              RHLDEGLLEALVQLGQGTPEDVRALIDQWVAEGLSIADTYRRLMDLCAPLALVDKSPSSV
Pseudomonas             NYFDQGLQRALMELHEGSLDEAVSLLGQWVDQDIAVAEVYRFMRERSGCGLLVDKSPSYA
                          :*         :                  *      : ****:**
```

FIGURE 12

| | |
|---|---|
| CurM | MEPTILERGEALFANSKYIYLVRHPYSVIESFVRMRMQKLVGLGEENPYRVAEQVWAKSN |
| CyanothecePCC7424 | MQREILDRGEAMFEGAKYIHLVRHPYSVIDSFSRMRMDKLVGVSGDNPYSIAESVWLESN |
| CyanothecePCC7822 | MQREILDRAEAIFEGAKYIHLVRHPYPVIDSFCRMRMDKLVGSEGDNPYQLAESIWWESN |
| Synechococcus | SDRHILDHSEILFDQAKYIHLVRHPYAVIESFTRLRMDKLLGAEQQNPYALAESIWRTSN |
| Haliangium | MDRDALMRVAREFPDARFWLVRHPLAVVESMIRRRIHAVVGAVED-PQTFAEQTWCQSV |
| Pseudomonas | SNPKALLQAELAFDKPRYIHLVRNPLAMIESFSRMRMHKLLGQQDNDGISTAERIWLEGN |
| | : * : :::: * ::::*: * :: ::. ** . |

| | |
|---|---|
| CurM | QNILNFLS-QLEPERQHQIRYEDLVKKPQQVLSQLCDFLNVPFEPELLQPYQGDRMTGGV |
| CyanothecePCC7424 | RNILDFSQ-TIDKERYYQLRYEDLVTQPSQMMRSLCEFLDIPFNSALLDPYQGDRMTDGV |
| CyanothecePCC7822 | RNIIEFSK-TISSDRYYQLRYEDLVTQPSQAMQALCEFLDIPFDSALLDPYQGQRMTDGV |
| Synechococcus | RNILDLGR-TVGADRYLQVIYEDLVRDPRKVLTNICDFLGVDFDEALLNPYSGDRLTDGL |
| Haliangium | DNALALRD-EVGAERFVTLRYEALVRDPAAAMAHLCDALGLAYEDALLRPYEGERMTDGL |
| Pseudomonas | LNLEAFFARHVEAERVLRVDYETLVRDPETTLRGICAFIDIEEFQPSMTMPYGVGRMNDGV |
| | * :: * .:* *.:: .: :: .:**:.: |

| | |
|---|---|
| CurM | HQKSLSISDPNFLKHNTIDESLADKWKTIQLPYPLKSETQRIASQLSYELPNLVTTPTNQ |
| CyanothecePCC7424 | YNQSISVGDPNFSQRRQIDPKLADAWKKIHLPQPLGDTTLRLAASFNYELPHETVLPS--- |
| CyanothecePCC7822 | YNQSMSVGDPNFSKRKQIDPKLADAWKDIQLPHPLGDNTRQLAISLNYPLPHQNIP---- |
| Synechococcus | HQQSMGVGDPNFLQHKTIDPALADKWRSITLPAALQLDTIQLAETFAYDLPQEPQLT--- |
| Haliangium | HDGSLSIGDPGFKERRDIEPTLADAWREVRLPRPPSAALCERAQRLGYPVASQRELVS--- |
| Pseudomonas | REGSLAIEDPNFLKRDRVDASLADAWRHRSLDRPLWPQTVALAGRLGYDEALPASAKR--- |
| | .: * *** : ** : * |

| | |
|---|---|
| CurM | QPQVSTTPSTEQPIMEEKFLEFGGNQICLCSWGSPEHPVVLCIHGILEQGLAWQEVALPL |
| CyanothecePCC7424 | PPRRGVGGEVISIPMQENYLTIRGLKLCLCSWGPEDGELILCIHGILEQGAAWEEVATRL |
| CyanothecePCC7822 | PLLRGEGGITEEVHLEEYINIRGLNLCLCSWGPKQGELILCVHGILEQGAAWGQMATRL |
| Synechococcus | PQTQSLP-------SMVERFVTVRGLETCLCEWGDRHQPLVLLHGILEQGASWQLIAPQL |
| Haliangium | --------------DLVLSTWGPESGDAVVCIHGHLDQGPLWTPVADRL |
| Pseudomonas | --------------DEAARQTLNVQAGEVSLSVSAWGRYEHPDYLCLHGLLDQATVWDDIAQNL |
| | . : ::*:* * |

FIGURE 12 (CONT)

```
CurM              AAQGYRVVAPDLFGHGRSSHLEMVTSYSSLTFLAQIDRVIQELPDQPLLLVGHSMGAMLA
CyanothecePCC7424 AQKGYRVIAPDLRGHGKSDHVGNGGSYNLIDFLGDLDAIATHLTDKPFTLVGHSLGSIIA
CyanothecePCC7822 AGLGYRVVAPDLRGQKSDHVGKGGSYNLIDFLADLDAIANSLTDQPFTLVGHSLGSIIA
Synechococcus     AAQGYWVAPDLRGHGKSAHAQ---SYSMLDFLADVDALAKQLGDRPFTLVGHSMGSIIG
Haliangium        AAQGLRVLAPDLRGHGRSPHGS----LGLFEHLADLDALLAAQAPGRIVLVGHSLGALIA
Pseudomonas       YASGRSCIAPDIRGHGLSGHGSPQRLPALLDYVMDTDAVHRASGTQPLELVAHSFGAVIA
                   *   :****:***  *    *     .  : ::     *  ::    :  * **:::::

CurM              TAIASVRPKKIKELILVELPLPAEESKKESAVNQLTTCLDYLSSTPQHPIFPDVATAASR
CyanothecePCC7424 AMFTSIRPEKVKHLVLVETVLPTEVHEGD-TVEQLATHLNYLSSPPKHPVFPDVETAAKR
CyanothecePCC7822 AMFTSIRPEKVKNLVLVETVLPTEVSQTD-AVEQLATHLNYLASPPEHPVFPDVETAAKR
Synechococcus     AMYAGIRQTQVEKLILVETIVPNDIDDAE-TGNHLTTHLDYLAAPPQHPIFPSLEVAARR
Haliangium        AFYAAARPERVAKLVLLDPGLPSPLSEGP---GAALARALDRRRD-AAHAPMAGLDEAARR
Pseudomonas       VAYAAAFPERVKKLWLIEPVLLAEKRHDP---RLFYREMVQFLAAPHEHLPLGSLQQAAER
                   :  .     * :* ::. ::               :      . .        ** *

CurM              LRQAIPSLSEEFSYILAQRITQPNQGG--VRWSWDAIIRTRSIILGLNNLPGGRSQYLEMLK
CyanothecePCC7424 LQTATPAMSEQLAMKLAKRITQAGEGG-IQWRWDSLLRTRAGIEFNGIN--RSRYLSLLK
CyanothecePCC7822 LQTATPAMSEALAISLAKRITEPCEGG-IRWRWDSLLRTRAGIEFNGIN--RSRYISLLE
Synechococcus     LRQATPQLPKDLSAFLTQRSTKSVEKG-VQWRWDAFLRTRAGIEFNGIS--RRRYLALLK
Haliangium        LRRAIPDLSEAWSRELAERVSEQRGEH-RVWRWDPRLRVLSGEGFD----RDTALEILA
Pseudomonas       IRAVSSFLTQDRACELAERMTTVGDDGERRWTWDPRLRFRAGLGLGLDR----DTYLQILH
                   :   .  .   .  : :*  :        : * *. :* .        :  .:*

CurM              SIQVPTTLVYGDSSKLNRPEDLQQQKMTMTQAKRVFLSGG--HNLHIDAAAALASLILTS-
CyanothecePCC7424 QIQAKITLIYGDQSDFNRPEDLQLQQQTMSQANRIVVNGG--HNLHLEAFEELANIING--
CyanothecePCC7822 QIQAPITLIYGDNSDFNRPEDLQAQQKAMSAAKRIILKGG--HNLHLDAYEQLANIIKQIL
Synechococcus     DIQAPITLIYGDQSEFNRPADLQAIQAALPQAQRLTVAGG--HNLHFENPQAIAQIVYQ--
Haliangium        SQHAPVTVAFAARGDRARPEDRRAIEDALGSATFVELDTASHHLHLARTEDVVGLIVERA
Pseudomonas       ALEVDVHIVFGRDSRSNRRKDIELQAQGLDDDCVTFIDGG--HNLHLQHPDE---------
                              .     :        .               *:.
```

FIGURE 12 (CONT)

```
CurM            |-----------------|-2211
CyanothecePCC7424 |-----------------|
CyanothecePCC7822 |-----GKTGQSF-----|
Synechococcus    |-----------------|
Haliangium       |-AAQSTMSSPDRSTNAP|
Pseudomonas      |-----------------|
```

FIGURE 12 (CONT)

SEQUENCE LISTING

```
<160> NUMBER OF SEQ ID NOS: 26

<210> SEQ ID NO 1
<211> LENGTH: 2211
<212> TYPE: PRT
<213> ORGANISM: Unknown
<220> FEATURE:
<223> OTHER INFORMATION: CurM protein sequence

<400> SEQUENCE: 1

Met Ser Asn Val Ser Lys Thr Thr Gln Gln Asp Val Ser Gln Glu
1               5                   10                  15

Val Leu Gln Val Leu Gln Glu Met Arg Ser Arg Leu Glu Ala Val Asn
                20                  25                  30

Lys Ala Lys Thr Glu Pro Ile Ala Ile Val Gly Met Ala Cys Arg Phe
            35                  40                  45

Pro Gly Gly Ala Asn Asp Pro Ser Thr Tyr Trp Arg Leu Leu His Asp
        50                  55                  60

Gly Ile Asp Ala Ile Thr Pro Val Pro Pro His Arg Trp Asp Val Asn
65                  70                  75                  80
```

```
Ala His Tyr Glu Pro Asn Pro Glu Ile Pro Gly Lys Ala Tyr Thr Lys
             85                  90                  95

Gln Gly Gly Phe Ile Glu Gln Val Asp Gln Phe Asp Pro Leu Phe Phe
        100                 105                 110

Gly Ile Ser Pro Arg Glu Ala Ile Ser Leu Asp Pro Gln Tyr Arg Leu
        115                 120                 125

Leu Leu Glu Val Thr Trp Glu Ala Leu Glu Asn Ala Gly Gln Thr Trp
130                 135                 140

Thr Asn Leu Lys Asn Ser Lys Thr Ser Val Phe Met Gly Val Ser Thr
145                 150                 155                 160

Asp Asp Tyr Ala Ser Leu Ser Asn Pro Ile Leu Ile Asn Asn Arg Ser
                165                 170                 175

Leu Gly Val Gly Arg Ile Ser His Leu Leu Gly Leu Gln Gly Ser Asn
            180                 185                 190

Ile Gln Leu Asp Thr Ala Cys Ser Ser Ser Leu Val Ala Ile His Leu
        195                 200                 205

Ala Cys Gln Ser Leu Arg Ser Gly Glu Ser Asn Leu Ala Leu Val Gly
    210                 215                 220

Gly Val Asn Leu Ile Leu Ser Pro Ile Ser Thr Ile Gly Arg Cys Thr
225                 230                 235                 240

Met Lys Ala Leu Ser Pro Asp Gly Arg Cys Lys Thr Phe Asp Ala Ala
                245                 250                 255

Ala Asn Gly Tyr Gly Gln Ala Glu Gly Cys Gly Val Val Val Leu Lys
            260                 265                 270

Arg Leu Ser Asp Ala Ile Thr Asp Gly Asp Leu Ile Ser Ala Leu Ile
        275                 280                 285

Arg Gly Ser Ala Ile Asn His Asp Gly Pro Ser Ser Gly Leu Thr Val
    290                 295                 300

Pro Asn Gly Met Ala Gln Lys Gln Val Ile Gln Gln Ala Leu Ser Asn
305                 310                 315                 320

Ala Arg Leu Glu Pro His Gln Val Ser Tyr Leu Glu Ala His Gly Thr
                325                 330                 335

Gly Thr Ala Leu Gly Asp Pro Ile Glu Ile Glu Ala Leu Ala Ala Ile
            340                 345                 350

Tyr Gly Lys Asn Arg Pro Val Asp Gln Pro Leu Val Val Gly Ser Val
        355                 360                 365

Lys Thr Asn Ile Gly His Leu Glu Ala Ala Gly Val Ser Ala Leu
    370                 375                 380

Ile Lys Val Val Leu Ala Leu Gln His Gln Glu Ile Pro Pro His Leu
385                 390                 395                 400

His Leu Lys Gln Pro Asn Pro Tyr Val Asp Trp Asp Lys Leu Pro Ile
                405                 410                 415

Lys Ile Pro Thr Ser Leu Met Pro Trp Asn Cys Glu Ala Lys Pro Arg
            420                 425                 430

Ile Ala Gly Ile Ser Ser Phe Gly Ile Ser Gly Thr Asn Ala His Leu
        435                 440                 445

Leu Leu Glu Glu Val Pro Glu Leu Ile Lys Gly Gln Lys Ala Lys Gly
    450                 455                 460

Lys Ser Glu Asn Asp Leu Glu Arg Pro Leu His Ile Leu Thr Leu Ser
465                 470                 475                 480

Thr Lys Thr Glu Lys Ala Leu Glu Glu Leu Val Ser Arg Tyr Gln Asn
                485                 490                 495
```

```
His Trp Glu Thr Tyr Pro Glu Leu Ala Ile Ser Asp Val Cys Tyr Thr
                500                 505                 510
Ala Asn Thr Gly Arg Ala Gln Phe Asn His Arg Leu Ala Val Ile Ala
            515                 520                 525
Ser Gly Ser Glu Glu Leu Thr Gln Lys Leu Arg Gln His Thr Ala Gly
        530                 535                 540
Glu Glu Val Val Gly Val Phe Ser Gly Lys Val Pro Asn Ser Gly Ser
545                 550                 555                 560
Glu Ser Lys Val Ala Phe Leu Phe Thr Gly Gln Gly Ser Gln Tyr Leu
                565                 570                 575
Asn Met Gly Arg Gln Leu Tyr Glu Thr Gln Pro Thr Phe Arg Gln Ala
            580                 585                 590
Leu Asp Thr Cys Asp His Ile Leu Arg Pro Tyr Leu Asp Asn Pro Leu
        595                 600                 605
Leu Glu Ile Leu Tyr Pro Gln Asp Ala Gln Lys Ser Asn Asp Ser Pro
        610                 615                 620
Leu Asp Gln Thr Gly Tyr Thr Gln Pro Ala Leu Phe Ser Ile Glu Tyr
625                 630                 635                 640
Ala Leu Leu Lys Leu Trp Glu Ser Trp Gly Ile Lys Pro Asn Val Val
                645                 650                 655
Met Gly His Ser Val Gly Glu Tyr Val Ala Ala Thr Val Ala Gly Val
            660                 665                 670
Phe Ser Leu Glu Asp Gly Leu Lys Leu Ile Ala Ala Arg Gly Arg Leu
        675                 680                 685
Met Gln Gly Leu Pro Ala Gly Gly Glu Met Val Ser Val Met Ala Ser
        690                 695                 700
Glu Ser Lys Val Leu Glu Thr Leu Lys Ala Met Ser Leu Glu Asp Lys
705                 710                 715                 720
Val Ala Ile Ala Ala Ile Asn Gly Pro Glu Ser Ile Val Ile Ser Gly
                725                 730                 735
Glu Ala Glu Ala Ile Arg Ala Met Ala Thr His Leu Glu Ser Val Gly
            740                 745                 750
Ile Lys Thr Lys Gln Leu Gln Val Ser His Ala Phe His Ser Pro Leu
        755                 760                 765
Met Glu Pro Met Leu Ala Glu Phe Glu Ala Val Ala Asn Gln Ile Thr
        770                 775                 780
Tyr His Gln Pro Arg Ile Pro Ile Ile Ser Asn Val Thr Gly Thr Lys
785                 790                 795                 800
Ala Asp Lys Ser Ile Ala Thr Ala Gln Tyr Trp Val Asn His Val Arg
                805                 810                 815
Gln Pro Val Arg Phe Ala Gln Gly Met Ala Thr Leu His Gln Gln Gly
            820                 825                 830
Tyr Glu Thr Phe Leu Glu Ile Gly Ala Lys Pro Ile Leu Leu Gly Met
        835                 840                 845
Gly Lys Gln Cys Leu Ser Pro Asp Val Gly Val Trp Leu Pro Ser Leu
        850                 855                 860
Arg His Gly Val Asp Glu Trp Gln Gln Ile Leu Ser Ser Leu Gly Gln
865                 870                 875                 880
Leu Tyr Val Gln Gly Ala Lys Val Asp Trp Ser Gly Phe Asp Arg Asp
                885                 890                 895
Tyr Ser Arg Glu Lys Val Val Leu Pro Thr Tyr Pro Phe Gln Arg Glu
            900                 905                 910
```

```
Arg Tyr Trp Val Glu Thr Ser Ile Asn Gln Gln Val Cys Ser
        915                 920                 925

Gly Glu Pro Asn Leu Gln Gly Thr Pro Glu Gly Thr Ser Thr Thr Ile
    930                 935                 940

Val Lys Leu Leu Ser Gln Gly Asn Thr Lys Glu Leu Ala Glu Lys Val
945                 950                 955                 960

Glu Lys Thr Ser Asp Leu Pro Pro Glu Gln Leu Lys Leu Leu Pro Asp
            965                 970                 975

Leu Leu Ala Ser Leu Ser Gln Gln His Gln Gln Glu Leu Ala Arg Leu
                980                 985                 990

Thr Thr Lys Lys Trp Phe Tyr Lys Val Gln Trp Ile Ser Gln Ala Ile
        995                 1000                1005

Lys Pro Gln Arg Asn Lys Ser Asn Asn Gln Val Cys His Trp Leu
    1010                1015                1020

Ile Leu Thr Asp Ser Lys Gly Leu Gly Lys Ser Leu Ala Thr His
    1025                1030                1035

Leu Gln Gln Leu Gly Asn Glu Cys Ser Val Val Tyr Gln Ala Asp
    1040                1045                1050

Asn Tyr Gln Asn Tyr Glu Pro Gly Ile Tyr His Ile Asn Pro Ser
    1055                1060                1065

His Pro Gln Glu Phe Glu Gln Val Tyr Gln Thr Ile Phe Glu Asn
    1070                1075                1080

Gly Lys Leu Pro Leu Gln Lys Val Ile His Leu Trp Ser Leu Asp
    1085                1090                1095

Thr Ala Ser Glu Gln Asp Leu Thr Thr Glu Thr Leu Glu Gln Ala
    1100                1105                1110

Gln Leu Trp Gly Cys Gly Ser Thr Leu His Leu Leu Gln Thr Leu
    1115                1120                1125

Val Lys Asn Pro Asn Ser Thr Pro Pro Lys Leu Trp Met Ile Thr
    1130                1135                1140

Arg Gly Thr Gln Pro Val Leu Ser Pro Thr Glu Lys Leu Thr Val
    1145                1150                1155

Ala Thr Ser Pro Leu Trp Gly Leu Gly Arg Thr Ile Ala Ser Glu
    1160                1165                1170

His Pro Gln Leu Trp Gly Gly Leu Val Asp Leu Asp Pro Gln Gly
    1175                1180                1185

Ser Glu Asp Glu Val Glu Val Leu Leu Gln Gln Ile Ile Asp Ser
    1190                1195                1200

Gln Lys Glu Asp His Leu Ala Val Arg Asn Arg Lys Ile Tyr Val
    1205                1210                1215

Ala Arg Leu Leu Lys His Ile Pro Gln Glu Ser Gln Pro Leu Ser
    1220                1225                1230

Leu Arg Ser Asp Ala Thr Tyr Leu Ile Thr Gly Gly Leu Gly Ala
    1235                1240                1245

Leu Gly Leu Lys Thr Ala Ala Trp Met Ala Glu Lys Gly Ala Arg
    1250                1255                1260

Asn Leu Val Leu Ile Ser Arg Arg Gln Pro Ser Glu Gln Ala Gln
    1265                1270                1275

Gln Thr Ile Gln Ser Leu Glu Leu Gly Thr Gln Val Lys Val
    1280                1285                1290

Leu Ser Ala Asp Ile Ser Val Glu Ser Asp Val Ala Asn Ile Leu
    1295                1300                1305

Glu Gln Ile Gln Thr Ser Leu Pro Pro Leu Leu Gly Val Ile His
```

```
            1310                1315                1320

Ala Ala Gly Val Leu Asp Asp Gly Leu Leu Gln Gln Thr Asn Trp
    1325                1330                1335

Glu Arg Phe Thr Lys Val Met Ala Pro Lys Val Asn Gly Thr Trp
    1340                1345                1350

Asn Leu His Lys Leu Thr Gln His Leu Ser Leu Asp Phe Phe Val
    1355                1360                1365

Cys Phe Ser Ser Met Ser Ser Leu Leu Gly Ser Pro Gly Gln Gly
    1370                1375                1380

Asn Tyr Ala Ala Ala Asn Ala Phe Met Asp Ala Val Val His Tyr
    1385                1390                1395

Arg Arg Glu Met Gly Leu Pro Gly Leu Ser Ile Asn Trp Gly Gly
    1400                1405                1410

Trp Ser Glu Gly Gly Met Ala Thr Arg Leu Ala Ser Gln His Gln
    1415                1420                1425

Asn Arg Met Gln Thr Ala Gly Ile Ser Leu Ile Ser Pro Glu Gln
    1430                1435                1440

Gly Ile Gln Val Leu Glu Glu Leu Val Arg Thr Gln Ser Thr Ala
    1445                1450                1455

Gln Val Gly Val Leu Pro Val Asp Trp Ser Val Leu Ala Lys Gln
    1460                1465                1470

Phe Ser Ser Ala Asn Pro Ser Ser Leu Leu Leu Glu Leu Leu Gln
    1475                1480                1485

Gln Glu Thr Ser Ser Glu Lys Thr Asp Glu Arg Ile Leu Glu Lys
    1490                1495                1500

Leu Gln Ala Ala Pro Ile Thr Glu Arg Gln Asp Ile Leu Lys Asn
    1505                1510                1515

Tyr Ile Gln Leu Val Val Ala Lys Thr Leu Gly Ile Asn Pro Ser
    1520                1525                1530

Lys Ile Ser Thr Asp Asp Asn Phe Val Glu Leu Gly Met Asp Ser
    1535                1540                1545

Leu Met Gly Met Glu Val Val Asn Lys Leu Ser Gly Asp Leu Asp
    1550                1555                1560

Phe Ile Ile Tyr Pro Arg Glu Phe Tyr Glu Arg Pro Thr Ile Asp
    1565                1570                1575

Ser Leu Thr Gln Tyr Leu Ser Ala Glu Leu Ser Glu Asp Asn Leu
    1580                1585                1590

Ala Thr Gln Pro Ser Pro Thr Ser Leu Glu Ile Phe Ala Thr Lys
    1595                1600                1605

Ser Ser Pro Ser Gly Asn Ser Ala Arg Pro Ala Ser Val Ser Ser
    1610                1615                1620

Arg Leu Pro Gly Ile Ile Phe Ile Leu Ser Ser Pro Arg Ser Gly
    1625                1630                1635

Ser Thr Leu Leu Arg Val Met Leu Ala Gly His Ser Ser Leu Phe
    1640                1645                1650

Ser Pro Pro Glu Leu His Leu Leu Pro Phe Asn Thr Met Lys Glu
    1655                1660                1665

Arg Gln Glu Gln Leu Asn Leu Ser Tyr Leu Gly Glu Gly Leu Gln
    1670                1675                1680

Lys Thr Phe Met Glu Val Lys Asn Leu Asp Ala Thr Ala Ser Gln
    1685                1690                1695

Ala Leu Ile Lys Asp Leu Glu Ser Gln Asn Leu Ser Ile Gln Gln
    1700                1705                1710
```

```
Val Tyr Gly Met Leu Gln Glu Asn Ile Ala Pro Arg Leu Leu Val
1715                1720                1725

Asp Lys Ser Pro Thr Tyr Ala Met Glu Pro Thr Ile Leu Glu Arg
1730                1735                1740

Gly Glu Ala Leu Phe Ala Asn Ser Lys Tyr Ile Tyr Leu Val Arg
1745                1750                1755

His Pro Tyr Ser Val Ile Glu Ser Phe Val Arg Met Arg Met Gln
1760                1765                1770

Lys Leu Val Gly Leu Gly Glu Glu Asn Pro Tyr Arg Val Ala Glu
1775                1780                1785

Gln Val Trp Ala Lys Ser Asn Gln Asn Ile Leu Asn Phe Leu Ser
1790                1795                1800

Gln Leu Glu Pro Glu Arg Gln His Gln Ile Arg Tyr Glu Asp Leu
1805                1810                1815

Val Lys Lys Pro Gln Gln Val Leu Ser Gln Leu Cys Asp Phe Leu
1820                1825                1830

Asn Val Pro Phe Glu Pro Glu Leu Leu Gln Pro Tyr Gln Gly Asp
1835                1840                1845

Arg Met Thr Gly Gly Val His Gln Lys Ser Leu Ser Ile Ser Asp
1850                1855                1860

Pro Asn Phe Leu Lys His Asn Thr Ile Asp Glu Ser Leu Ala Asp
1865                1870                1875

Lys Trp Lys Thr Ile Gln Leu Pro Tyr Pro Leu Lys Ser Glu Thr
1880                1885                1890

Gln Arg Ile Ala Ser Gln Leu Ser Tyr Glu Leu Pro Asn Leu Val
1895                1900                1905

Thr Thr Pro Thr Asn Gln Gln Pro Gln Val Ser Thr Thr Pro Ser
1910                1915                1920

Thr Glu Gln Pro Ile Met Glu Glu Lys Phe Leu Glu Phe Gly Gly
1925                1930                1935

Asn Gln Ile Cys Leu Cys Ser Trp Gly Ser Pro Glu His Pro Val
1940                1945                1950

Val Leu Cys Ile His Gly Ile Leu Glu Gln Gly Leu Ala Trp Gln
1955                1960                1965

Glu Val Ala Leu Pro Leu Ala Ala Gln Gly Tyr Arg Val Val Ala
1970                1975                1980

Pro Asp Leu Phe Gly His Gly Arg Ser Ser His Leu Glu Met Val
1985                1990                1995

Thr Ser Tyr Ser Ser Leu Thr Phe Leu Ala Gln Ile Asp Arg Val
2000                2005                2010

Ile Gln Glu Leu Pro Asp Gln Pro Leu Leu Leu Val Gly His Ser
2015                2020                2025

Met Gly Ala Met Leu Ala Thr Ala Ile Ala Ser Val Arg Pro Lys
2030                2035                2040

Lys Ile Lys Glu Leu Ile Leu Val Glu Leu Pro Leu Pro Ala Glu
2045                2050                2055

Glu Ser Lys Lys Glu Ser Ala Val Asn Gln Leu Thr Thr Cys Leu
2060                2065                2070

Asp Tyr Leu Ser Ser Thr Pro Gln His Pro Ile Phe Pro Asp Val
2075                2080                2085

Ala Thr Ala Ala Ser Arg Leu Arg Gln Ala Ile Pro Ser Leu Ser
2090                2095                2100
```

| Glu | Glu | Phe | Ser | Tyr | Ile | Leu | Ala | Gln | Arg | Ile | Thr | Gln | Pro | Asn |
| | 2105 | | | | 2110 | | | | | 2115 | | | | |

| Gln | Gly | Gly | Val | Arg | Trp | Ser | Trp | Asp | Ala | Ile | Ile | Arg | Thr | Arg |
| | 2120 | | | | | 2125 | | | | 2130 | | | | |

| Ser | Ile | Leu | Gly | Leu | Asn | Asn | Leu | Pro | Gly | Gly | Arg | Ser | Gln | Tyr |
| | 2135 | | | | | 2140 | | | | 2145 | | | | |

| Leu | Glu | Met | Leu | Lys | Ser | Ile | Gln | Val | Pro | Thr | Thr | Leu | Val | Tyr |
| | 2150 | | | | | 2155 | | | | 2160 | | | | |

| Gly | Asp | Ser | Ser | Lys | Leu | Asn | Arg | Pro | Glu | Asp | Leu | Gln | Gln | Gln |
| | 2165 | | | | | 2170 | | | | 2175 | | | | |

| Lys | Met | Thr | Met | Thr | Gln | Ala | Lys | Arg | Val | Phe | Leu | Ser | Gly | Gly |
| | 2180 | | | | | 2185 | | | | 2190 | | | | |

| His | Asn | Leu | His | Ile | Asp | Ala | Ala | Ala | Ala | Leu | Ala | Ser | Leu | Ile |
| | 2195 | | | | | 2200 | | | | 2205 | | | | |

| Leu | Thr | Ser |
| | 2210 | |

```
<210> SEQ ID NO 2
<211> LENGTH: 6633
<212> TYPE: DNA
<213> ORGANISM: Unknown
<220> FEATURE:
<223> OTHER INFORMATION: CurM nucleotide sequence

<400> SEQUENCE: 2
atgagcaatg tttctaaaac aacccaacaa gatgtatcct ctcaagaggt gcttcaagta      60
ttacaagaaa tgcggagtag gcttgaagca gtcaacaaag caaaaactga accaatcgct     120
attgtgggca tggcctgtcg gtttcctggt ggagctaatg acccatctac atattggcgc     180
ttattacatg atggaataga tgctattaca ccagtaccac ctcaccgttg ggatgttaat     240
gctcattacg agcctaaccc agaaattcca ggaaaagcct acaccaaaca gggtggattt     300
attgagcaag ttgaccagtt cgacccttg ttttttggta ttctcctcg ggaggcaatt      360
agtttagatc ctcagtacag actacttta gaagttacct gggaagctct ggaaaatgct     420
gggcaaacat ggactaacct taagaatagt aaaacaagtg tattcatggg cgtctccacg     480
gatgactatg cgagtctgag taatcctatt cttattaata atcgaagtct tggtgtaggt     540
cgtatttctc atttacttgg tttacaaggg tctaatatac agttagatac agcttgttca     600
agttctttag ttgcgatcca tctagcttgt caaagtttgc gatcaggaga atctaattta     660
gcattagtag gtgagtgaa tttaatctta tcaccaatca gtactattgg ccgctgtaca     720
atgaaagcac tatcccctga tggtcgctgc aagactttg atgctgcggc taacggttat     780
ggtcaggcag aaggatgtgg tgttgtcgtt ttgaagcgtt tgtccgatgc aattactgat     840
ggtgatttaa tttcagcact tatccgaggt tctgcaatca atcacgatgg acctagtagc     900
ggtcttacag ttcctaatgg aatggcccag aaacaagtga ttcaacaagc cttgagcaat     960
gctaggttag aacccatca ggtgagctat ttggaagctc atgggacagg aactgcttta    1020
ggagacccca tcgaaataga agctttggcc gcaatatatg gcaaaaatcg tccagtggat    1080
cagcctttag tagttggttc cgtgaagact aatattggac ttagaggc agccgcaggt    1140
gtatcagctt taattaaggt cgttttagca cttcagcatc aagaaattcc acctcattta    1200
cacttaaagc agcctaatcc ctatgtagat tgggataaat taccaattaa aataccaact    1260
tcattaatgc cttggaattg tgaagccaaa ccgagaatag cagggattag ttcttttggt    1320
ataagtggca ctaatgctca tttactcttg gaagaggttc ctgagctaat caagggtcaa    1380
```

```
aaggcaaaag gaaaaagtga aaatgactta gaacgtcccc tccatatact aaccctgtca   1440
accaagacag aaaaagcgct cgaagagtta gtcagtcgtt atcaaaacca ttgggaaact   1500
tatccagaat tggctatctc agatgtctgt tacacagcta acacaggacg tgcccagttt   1560
aaccatcgcc tagccgttat tgcctctggc tcagaggaat aacacaaaa acttcggcaa    1620 cacacagcag gggaagaagt agttggagtt ttttctggca aagtacccaa tagtggcagt   1680
gagagcaaag tagctttctt atttacaggt cagggttccc agtatttgaa tatgggaagg   1740
caattgtatg aaactcaacc tactttcgt caagctttag atacatgtga ccatatcctg     1800
cgtccttacc tggacaatcc actcctagaa attctatacc ctcaagatgc acaaaagtca   1860
aatgattctc cactagatca aactggttac acccaaccag ctctgttctc tattgaatac   1920
gctttgctga agttatggga atcttgggt attaagccaa atgtcgtgat gggtcacagt    1980
gtgggagaat atgtagcagc aacagtagca ggagtattta gtttagaaga tggcttgaaa   2040
ctaattgccg ctagaggaag gttaatgcaa ggattacctg ctggtggaga gatggtttca   2100
gttatggctt cagagtccaa ggttctagag actctgaagg caatgtccct agaagacaaa   2160
gtagcaatag cagccatcaa tggacccgaa agcatagtca tttccggtga agctgaagcc   2220
attagagcga tggcaactca cctcgaatca gtaggcatca aaaccaaaca gctacaagta   2280
tcccatgctt tccattcacc cttgatggaa cccatgttgg cagagtttga agctgtagcc   2340
aatcaaatca cctaccatca acccaggatt cccatcatat ctaacgtcac aggcacaaaa   2400
gcagacaaga gcatagccac agcccaatat tgggtcaatc atgtgcgcca accggtaagg   2460
tttgcccaag gtatggcaac cttgcaccaa caaggctatg aaactttcct agaaattgga   2520
gccaaaccaa tattattagg tatgggcaag caatgtctat cgccagacgt tggtgtgtgg   2580
ctgccatctt tgcgtcatgg agtggatgaa tggcaacaga ttctttcaag tttaggacag   2640
ttatatgtac agggagccaa agtagattgg tcaggatttg atcgagatta tagccgtgag   2700
aaagtagtat tgccaactta cccattccaa cgagaacggt attgggtaga aactagtata   2760
aatcaacaac aagttgtatg ctctggggag ccaaacctcc aaggtactcc tgaaggtacg   2820
agtactacta tcgttaaatt actcagccaa ggaaatacta aagagttagc agaaaaagtc   2880
gaaaaaacta gtgatttacc accggaacag ttgaaattat taccggattt attagcctca   2940
ttatctcaac aacatcaaca agaattagcc agattaacta ccaaaaaatg gttttataaa   3000
gtccagtgga tatctcaagc tataaaaccc caacgaaaca aatcaaataa tcaagtctgt   3060
cattggttga ttttgacaga ttcaaaagga ttgggcaaat cttttggccac tcatttgcaa   3120 cagctgggaa atgaatgcag tgtagtttat caagctgata attatcaaaa ttatgaacca   3180
gggatttatc acattaatcc atctcatccc caggaatttg aacaagtata tcaaacaata   3240
ttcgaaaacg gtaaattacc cttacaaaag gtaattcatc tgtggagttt ggatactgct   3300
tctgaacaag atttaaccac cgaaaacctta gaacaagcgc aactatgggg atgtggcagt   3360
acactgcact tattacaaac tttagtcaaa aaccccaact caacaccacc aaaactctgg   3420
atgatcacca gagggactca acctgtattg tcaccaacag agaaactaac agtggcaaca   3480
tcaccattgt ggggattagg tagaacgatc gcttctgaac atccgcagct ttggggaggt   3540
ttggtagatc tcgatccaca gggttccgaa gatgaggtgg aagtactatt acaacagata   3600
atagatagtc aaaagaaga ccatctagcg gtgcgcaatc gcaaaatata cgttgctcgt    3660
ttactcaagc acattcccca agaatctcaa cccctgtcac tgcgatctga tgccacatac   3720
```

```
ctaattactg gaggattagg agccctgggg ttgaagacag cagcatggat ggcagaaaaa   3780
ggagctagaa atttagtttt aatcagtcgt cgtcaaccct ctgagcaagc acaacaaacg   3840
attcaaagtt tggaagaatt aggcactcaa gtaaaagttc tttcagcaga tatatcagtt   3900
gaatccgatg tcgccaatat cctagagcaa attcaaacat ctctacccccc actactaggt   3960
gtaattcatg cagcaggcgt tttggatgat ggcctactgc aacaaaccaa ttgggagcgc   4020
tttacgaaag tgatggcccc caaagtcaac gggacttgga atctacataa attaacccag   4080
catttatccc tagatttctt tgtttgcttc tcatctatga gttccttatt aggttcaccc   4140
ggtcaaggaa actatgctgc agctaatgct tttatggatg ctgtagttca ttatcgtagg   4200
gagatgggat taccaggatt aagtattaac tggggaggct ggtctgaagg tggtatggcg   4260
actcgtcttg caagtcagca tcaaaatcga atgcaaacgg cagggataag tttgatttct   4320
ccagagcaag aatacaagt attagaggaa cttgtacgca ctcagtctac agcacaggtg   4380
ggagtattgc ctgtagattg gtcggtattg gcaaaacaat ttagttcggc aaatccaagt   4440
tctttactat tagaactctt gcaacaggag acaagctcag aaaagacaga cgaacgcatt   4500
ttagaaaaat tgcaagctgc accaataact gaacgtcaag atattttgaa aaattatatt   4560
caattggtag tagcaaaaac tctcggaatc aatccatcaa aaatttccac tgatgacaat   4620
tttgtagagt tgggtatgga ttccctaatg ggaatggaag ttgtcaataa acttagtggc   4680
gacctagatt ttattatcta tcccagagag ttttacgaac gaccaacaat cgactccctg   4740
actcaatatt tgagtgctga gttgagtgaa gataatcttg ctactcaacc atctccaaca   4800
agcttagaaa tctttgcaac caaaagttca cctagtggaa actctgcacg tccagcctcc   4860
gtctcttcac gtcttcctgg tattattttt atcctttcga gtccccgctc aggttcaact   4920
ttactcagag tcatgctagc gggtcattct tccctgtttt caccaccgga gttgcatctg   4980
ttacccttta acaccatgaa ggagcgacag gagcaactaa acctttctta cttggggaa   5040
gggctacaaa aaactttcat ggaagtaaaa aacctggatg caacagctag tcaggctcta   5100
attaaagacc tcgagtcaca gaacttatca attcagcagg tatatgggat gctccaggag   5160
aacatagcac ctcgtctact cgtagacaag tctcctactt atgctatgga gcccactatc   5220
ctagaacgag gggaagcact cttttgctaac tccaaataca tttatctagt tcgtcatccc   5280
tactcagtca tagaatcatt tgtgcggatg cggatgcaaa aacttgtcgg gttaggtgag   5340
gaaaatcctt accgggtagc ggagcaggtg tgggctaaga gtaaccagaa cattctaaat   5400
ttcctgagcc agttggagcc agagcgtcag catcagattc gctatgaaga cttggtgaaa   5460
aaacctcaac aagtgctatc ccaactatgc gactttctca atgttcccct cgagccagaa   5520
cttttgcaac cttatcaggg cgatcgcatg acagggggtg ttcatcaaaa gtcattgtca   5580
atcagtgacc ctaacttcct caaacacaat actattgatg agagcttggc agacaaatgg   5640
aaaacgattc aattacctta tccgttgaag tcagaaactc aacggatagc cagccaactt   5700
agttatgagt tgccaaacct agttacaact ccgacaaatc aacagcctca gtctctaca   5760
actccctcaa cagagcagcc tattatggag gaaaaattcc tggagttcgg aggaaatcag   5820
atctgtctgt gtagttgggg ttccccggag catcctgtag ttctgtgtat tcatggaatt   5880
ttggaacaag gattagcttg gcaagaagtc gcacttcctc tagcagcaca aggttatcgg   5940
gtagtggctc ctgacttatt tggtcacggg cgctcttctc atttggaaat ggtgacttct   6000
tatagttcac tgacatttt agctcagata gaccgggtaa ttcaggaatt accagaccaa   6060
cctttgttgt tagtaggtca ttccatgggt gccatgctgg caactgcgat cgctagcgtg   6120
```

```
cgaccaaaga aaatcaaaga gttgattttg gtagaacttc cgctacctgc tgaggaaagc    6180
aagaaagaat ccgcagttaa tcagctaacg acttgtttag actatctcag ttctactcct    6240
caacatccca tctttcctga tgtggcaact gctgcaagta ggttgcgtca agcgatacct    6300
agtctgtcag aagaatttc ttatatctta gctcagcgaa ttacacaacc aaatcaaggt    6360
ggagttcgct ggagttggga tgcaattatt cgtactcgtt ctattctggg tttaaacaat    6420
ttacctggtg gtcgatctca atatttggag atgctcaaat ctatccaagt tccgactacg    6480
ttagtttatg gagatagtag caaactaaat cgaccagaag atttgcaaca acagaaaatg    6540
actatgactc aagctaaacg agttttctg tcaggagggc ataatcttca tattgatgct    6600
gctgctgctt tagcatcact tatcttaaca tcc                                  6633
```

<210> SEQ ID NO 3
<211> LENGTH: 283
<212> TYPE: PRT
<213> ORGANISM: Unknown
<220> FEATURE:
<223> OTHER INFORMATION: CurM protein sequence (TE fragment)

<400> SEQUENCE: 3

```
Met Glu Glu Lys Phe Leu Glu Phe Gly Gly Asn Gln Ile Cys Leu Cys
1               5                   10                  15

Ser Trp Gly Ser Pro Glu His Pro Val Val Leu Cys Ile His Gly Ile
            20                  25                  30

Leu Glu Gln Gly Leu Ala Trp Gln Glu Val Ala Leu Pro Leu Ala Ala
        35                  40                  45

Gln Gly Tyr Arg Val Val Ala Pro Asp Leu Phe Gly His Gly Arg Ser
    50                  55                  60

Ser His Leu Glu Met Val Thr Ser Tyr Ser Ser Leu Thr Phe Leu Ala
65                  70                  75                  80

Gln Ile Asp Arg Val Ile Gln Glu Leu Pro Asp Gln Pro Leu Leu Leu
                85                  90                  95

Val Gly His Ser Met Gly Ala Met Leu Ala Thr Ala Ile Ala Ser Val
            100                 105                 110

Arg Pro Lys Lys Ile Lys Glu Leu Ile Leu Val Glu Leu Pro Leu Pro
        115                 120                 125

Ala Glu Glu Ser Lys Lys Glu Ser Ala Val Asn Gln Leu Thr Thr Cys
    130                 135                 140

Leu Asp Tyr Leu Ser Ser Thr Pro Gln His Pro Ile Phe Pro Asp Val
145                 150                 155                 160

Ala Thr Ala Ala Ser Arg Leu Arg Gln Ala Ile Pro Ser Leu Ser Glu
                165                 170                 175

Glu Phe Ser Tyr Ile Leu Ala Gln Arg Ile Thr Gln Pro Asn Gln Gly
            180                 185                 190

Gly Val Arg Trp Ser Trp Asp Ala Ile Ile Arg Thr Arg Ser Ile Leu
        195                 200                 205

Gly Leu Asn Asn Leu Pro Gly Gly Arg Ser Gln Tyr Leu Glu Met Leu
    210                 215                 220

Lys Ser Ile Gln Val Pro Thr Thr Leu Val Tyr Gly Asp Ser Ser Lys
225                 230                 235                 240

Leu Asn Arg Pro Glu Asp Leu Gln Gln Gln Lys Met Thr Met Thr Gln
                245                 250                 255

Ala Lys Arg Val Phe Leu Ser Gly Gly His Asn Leu His Ile Asp Ala
            260                 265                 270
```

```
Ala Ala Ala Leu Ala Ser Leu Ile Leu Thr Ser
        275                 280

<210> SEQ ID NO 4
<211> LENGTH: 284
<212> TYPE: PRT
<213> ORGANISM: Unknown
<220> FEATURE:
<223> OTHER INFORMATION: CurM protein sequence (ST fragment)

<400> SEQUENCE: 4

Ser Ser Arg Leu Pro Gly Ile Ile Phe Ile Leu Ser Ser Pro Arg Ser
1               5                   10                  15

Gly Ser Thr Leu Leu Arg Val Met Leu Ala Gly His Ser Ser Leu Phe
            20                  25                  30

Ser Pro Pro Glu Leu His Leu Leu Pro Phe Asn Thr Met Lys Glu Arg
        35                  40                  45

Gln Glu Gln Leu Asn Leu Ser Tyr Leu Gly Glu Gly Leu Gln Lys Thr
    50                  55                  60

Phe Met Glu Val Lys Asn Leu Asp Ala Thr Ala Ser Gln Ala Leu Ile
65                  70                  75                  80

Lys Asp Leu Glu Ser Gln Asn Leu Ser Ile Gln Gln Val Tyr Gly Met
                85                  90                  95

Leu Gln Glu Asn Ile Ala Pro Arg Leu Leu Val Asp Lys Ser Pro Thr
            100                 105                 110

Tyr Ala Met Glu Pro Thr Ile Leu Glu Arg Gly Glu Ala Leu Phe Ala
        115                 120                 125

Asn Ser Lys Tyr Ile Tyr Leu Val Arg His Pro Tyr Ser Val Ile Glu
    130                 135                 140

Ser Phe Val Arg Met Arg Met Gln Lys Leu Val Gly Leu Gly Glu Glu
145                 150                 155                 160

Asn Pro Tyr Arg Val Ala Glu Gln Val Trp Ala Lys Ser Asn Gln Asn
                165                 170                 175

Ile Leu Asn Phe Leu Ser Gln Leu Glu Pro Glu Arg Gln His Gln Ile
            180                 185                 190

Arg Tyr Glu Asp Leu Val Lys Lys Pro Gln Gln Val Leu Ser Gln Leu
        195                 200                 205

Cys Asp Phe Leu Asn Val Pro Phe Glu Pro Glu Leu Leu Gln Pro Tyr
    210                 215                 220

Gln Gly Asp Arg Met Thr Gly Gly Val His Gln Lys Ser Leu Ser Ile
225                 230                 235                 240

Ser Asp Pro Asn Phe Leu Lys His Asn Thr Ile Asp Glu Ser Leu Ala
                245                 250                 255

Asp Lys Trp Lys Thr Ile Gln Leu Pro Tyr Pro Leu Lys Ser Glu Thr
            260                 265                 270

Gln Arg Ile Ala Ser Gln Leu Ser Tyr Glu Leu Pro
        275                 280

<210> SEQ ID NO 5
<211> LENGTH: 88
<212> TYPE: PRT
<213> ORGANISM: Unknown
<220> FEATURE:
<223> OTHER INFORMATION: CurM peptide sequence (ACP fragment)

<400> SEQUENCE: 5

Gln Ala Ala Pro Ile Thr Glu Arg Gln Asp Ile Leu Lys Asn Tyr Ile
```

```
                1               5                  10                  15
        Gln Leu Val Val Ala Lys Thr Leu Gly Ile Asn Pro Ser Lys Ile Ser
                        20                  25                  30
        Thr Asp Asp Asn Phe Val Glu Leu Gly Met Asp Ser Leu Met Gly Met
                    35                  40                  45
        Glu Val Val Asn Lys Leu Ser Gly Asp Leu Asp Phe Ile Ile Tyr Pro
                50                  55                  60
        Arg Glu Phe Tyr Glu Arg Pro Thr Ile Asp Ser Leu Thr Gln Tyr Leu
        65                  70                  75                  80

Ser Ala Glu Leu Ser Glu Asp Asn
                        85

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ggatgcggat gcaaaaactt g                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
cggatgcaaa aacttgtcgg g                                              21

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
catatgacag acgaacgcat tttag                                          25

<210> SEQ ID NO 9
<211> LENGTH: 26
<212> TYPE: DNA
<213> ORGANISM: Artificial Sequence
<220> FEATURE:
<223> OTHER INFORMATION: Synthetic nucleotide

<400> SEQUENCE: 9
gcggccgcta agcttgttgg agatgg                                         26

<210> SEQ ID NO 10
<211> LENGTH: 27
<212> TYPE: DNA
<213> ORGANISM: Artificial Sequence
<220> FEATURE:
<223> OTHER INFORMATION: Synthetic nucleotide

<400> SEQUENCE: 10
catatgatct ttgcaaccaa aagttca                                        27

<210> SEQ ID NO 11
```

```
<211> LENGTH: 271
<212> TYPE: PRT
<213> ORGANISM: Pseudomonas entomophiliaL48

<400> SEQUENCE: 11

Arg Gln Thr Leu Asn Val Gln Ala Gly Glu Val Ser Leu Ser Val Ser
1               5                   10                  15

Ala Trp Gly Arg Tyr Glu His Pro Asp Tyr Leu Cys Leu His Gly Leu
            20                  25                  30

Leu Asp Gln Ala Thr Val Trp Asp Ile Ala Gln Asn Leu Tyr Ala
        35                  40                  45

Ser Gly Arg Ser Cys Ile Ala Pro Asp Ile Arg Gly His Gly Leu Ser
    50                  55                  60

Gly His Gly Ser Pro Gln Arg Leu Pro Ala Leu Leu Asp Tyr Val Met
65                  70                  75                  80

Asp Thr Asp Ala Val His Arg Ala Ser Gly Thr Gln Pro Leu Glu Leu
                85                  90                  95

Val Ala His Ser Phe Gly Ala Val Ile Ala Val Ala Tyr Ala Ala Ala
            100                 105                 110

Phe Pro Glu Arg Val Lys Lys Leu Trp Leu Ile Glu Pro Val Leu Leu
        115                 120                 125

Ala Glu Lys Arg His Asp Pro Arg Leu Phe Tyr Arg Glu Met Val Gln
    130                 135                 140

Phe Leu Ala Ala Pro His Glu His Leu Pro Leu Gly Ser Leu Gln Gln
145                 150                 155                 160

Ala Ala Glu Arg Ile Arg Ala Val Ser Ser Phe Leu Thr Gln Asp Arg
                165                 170                 175

Ala Cys Glu Leu Ala Glu Arg Met Thr Thr Val Gly Asp Asp Gly Glu
            180                 185                 190

Arg Arg Trp Thr Trp Asp Pro Arg Leu Arg Phe Arg Ala Gly Leu Gly
        195                 200                 205

Leu Gly Leu Asp Arg Asp Thr Tyr Leu Gln Ile Leu His Ala Leu Glu
    210                 215                 220

Val Asp Val His Ile Val Phe Gly Arg Asp Ser Arg Ser Asn Arg Arg
225                 230                 235                 240

Lys Asp Ile Glu Leu Gln Ala Gln Gly Leu Asp Asp Cys Val Thr
                245                 250                 255

Phe Ile Asp Gly Gly His Asn Leu His Leu Gln His Pro Asp Glu
            260                 265                 270

<210> SEQ ID NO 12
<211> LENGTH: 289
<212> TYPE: PRT
<213> ORGANISM: Haliangium ochraceum DSM 14365

<400> SEQUENCE: 12

Tyr Pro Val Ala Ser Gln Arg Glu Leu Val Ser Asp Leu Val Leu Ser
1               5                   10                  15

Thr Trp Gly Pro Glu Ser Gly Asp Ala Val Val Cys Ile His Gly His
            20                  25                  30

Leu Asp Gln Gly Pro Leu Trp Thr Pro Val Ala Asp Arg Leu Ala Ala
        35                  40                  45

Gln Gly Leu Arg Val Leu Ala Pro Asp Leu Arg Gly His Gly Arg Ser
    50                  55                  60

Pro His Gly Ser Leu Gly Leu Phe Glu His Leu Ala Asp Leu Asp Ala
65                  70                  75                  80
```

```
Leu Leu Ala Ala Gln Ala Pro Gly Arg Ile Val Leu Val Gly His Ser
                85                  90                  95

Leu Gly Ala Leu Ile Ala Ala Phe Tyr Ala Ala Ala Arg Pro Glu Arg
            100                 105                 110

Val Ala Lys Leu Val Leu Leu Asp Pro Gly Leu Pro Ser Pro Leu Ser
        115                 120                 125

Glu Gly Pro Gly Ala Ala Leu Ala Arg Ala Leu Asp Arg Arg Arg Asp
    130                 135                 140

Ala Ala His Ala Pro Met Ala Gly Leu Asp Glu Ala Ala Arg Arg Leu
145                 150                 155                 160

Arg Arg Ala Ile Pro Asp Leu Ser Glu Ala Trp Ser Arg Glu Leu Ala
                165                 170                 175

Glu Arg Val Ser Glu Gln Arg Gly Glu His Arg Val Trp Arg Trp Asp
            180                 185                 190

Pro Arg Leu Arg Val Leu Ser Gly Glu Gly Phe Asp Arg Asp Thr Ala
        195                 200                 205

Leu Glu Ile Leu Ala Ser Gln His Ala Pro Val Thr Val Ala Phe Ala
    210                 215                 220

Ala Arg Gly Asp Arg Ala Arg Pro Glu Asp Arg Arg Ala Ile Glu Asp
225                 230                 235                 240

Ala Leu Gly Ser Ala Thr Phe Val Glu Leu Asp Thr Ala Ser His His
                245                 250                 255

Leu His Leu Ala Arg Thr Glu Asp Val Val Gly Leu Ile Val Glu Arg
            260                 265                 270

Ala Ala Ala Gln Ser Thr Met Ser Ser Pro Asp Arg Ser Thr Asn Ala
        275                 280                 285

Pro

<210> SEQ ID NO 13
<211> LENGTH: 276
<212> TYPE: PRT
<213> ORGANISM: Synechococcus PCC 7002

<400> SEQUENCE: 13

Met Val Glu Arg Phe Val Thr Val Arg Gly Leu Glu Thr Cys Leu Cys
1               5                   10                  15

Glu Trp Gly Asp Arg His Gln Pro Leu Val Leu Leu His Gly Ile
            20                  25                  30

Leu Glu Gln Gly Ala Ser Trp Gln Leu Ile Ala Pro Gln Leu Ala Ala
        35                  40                  45

Gln Gly Tyr Trp Val Val Ala Pro Asp Leu Arg Gly His Gly Lys Ser
    50                  55                  60

Ala His Ala Gln Ser Tyr Ser Met Leu Asp Phe Leu Ala Asp Val Asp
65                  70                  75                  80

Ala Leu Ala Lys Gln Leu Gly Asp Arg Pro Phe Thr Leu Val Gly His
                85                  90                  95

Ser Met Gly Ser Ile Ile Gly Ala Met Tyr Ala Gly Ile Arg Gln Thr
            100                 105                 110

Gln Val Glu Lys Leu Ile Leu Val Glu Thr Ile Val Pro Asn Asp Ile
        115                 120                 125

Asp Asp Ala Glu Thr Gly Asn His Leu Thr Thr His Leu Asp Tyr Leu
    130                 135                 140

Ala Ala Pro Pro Gln His Pro Ile Phe Pro Ser Leu Glu Val Ala Ala
145                 150                 155                 160
```

```
Arg Arg Leu Arg Gln Ala Thr Pro Gln Leu Pro Lys Asp Leu Ser Ala
            165                 170                 175
Phe Leu Thr Gln Arg Ser Thr Lys Ser Val Glu Lys Gly Val Gln Trp
        180                 185                 190
Arg Trp Asp Ala Phe Leu Arg Thr Arg Ala Gly Ile Glu Phe Asn Gly
    195                 200                 205
Ile Ser Arg Arg Arg Tyr Leu Ala Leu Leu Lys Asp Ile Gln Ala Pro
210                 215                 220
Ile Thr Leu Ile Tyr Gly Asp Gln Ser Glu Phe Asn Arg Pro Ala Asp
225                 230                 235                 240
Leu Gln Ala Ile Gln Ala Leu Pro Gln Ala Gln Arg Leu Thr Val
                245                 250                 255
Ala Gly Gly His Asn Leu His Phe Glu Asn Pro Gln Ala Ile Ala Gln
            260                 265                 270
Ile Val Tyr Gln
            275

<210> SEQ ID NO 14
<211> LENGTH: 279
<212> TYPE: PRT
<213> ORGANISM: Cyanothece PCC 7424

<400> SEQUENCE: 14

Met Gln Glu Asn Tyr Leu Thr Ile Arg Gly Leu Lys Leu Cys Leu Cys
1               5                   10                  15
Ser Trp Gly Pro Glu Asp Gly Glu Leu Ile Leu Cys Ile His Gly Ile
            20                  25                  30
Leu Glu Gln Gly Ala Ala Trp Glu Glu Val Ala Thr Arg Leu Ala Gln
        35                  40                  45
Lys Gly Tyr Arg Val Ile Ala Pro Asp Leu Arg Gly His Gly Lys Ser
    50                  55                  60
Asp His Val Gly Asn Gly Gly Ser Tyr Asn Leu Ile Asp Phe Leu Gly
65                  70                  75                  80
Asp Leu Asp Ala Ile Ala Thr His Leu Thr Asp Lys Pro Phe Thr Leu
                85                  90                  95
Val Gly His Ser Leu Gly Ser Ile Ile Ala Ala Met Phe Thr Ser Ile
            100                 105                 110
Arg Pro Glu Lys Val Lys His Leu Val Leu Val Glu Thr Val Leu Pro
        115                 120                 125
Thr Glu Val His Glu Gly Asp Thr Val Glu Gln Leu Ala Thr His Leu
    130                 135                 140
Asn Tyr Leu Ser Ser Pro Pro Lys His Pro Val Phe Pro Asp Val Glu
145                 150                 155                 160
Thr Ala Ala Lys Arg Leu Gln Thr Ala Thr Pro Ala Met Ser Glu Gln
                165                 170                 175
Leu Ala Met Lys Leu Ala Lys Arg Ile Thr Gln Ala Gly Glu Gly Gly
            180                 185                 190
Ile Gln Trp Arg Trp Asp Ser Leu Leu Arg Thr Arg Ala Gly Ile Glu
        195                 200                 205
Phe Asn Gly Ile Asn Arg Ser Arg Tyr Leu Ser Leu Leu Lys Gln Ile
    210                 215                 220
Gln Ala Lys Ile Thr Leu Ile Tyr Gly Asp Gln Ser Asp Phe Asn Arg
225                 230                 235                 240
Pro Glu Asp Leu Gln Leu Gln Gln Gln Thr Met Ser Gln Ala Asn Arg
```

```
                    245                 250                 255

Ile Val Val Asn Gly Gly His Asn Leu His Leu Glu Ala Phe Glu Glu
            260                 265                 270

Leu Ala Asn Ile Ile Asn Gly
            275

<210> SEQ ID NO 15
<211> LENGTH: 288
<212> TYPE: PRT
<213> ORGANISM: Cyanothece PCC 7822

<400> SEQUENCE: 15

Leu Glu Glu Glu Tyr Ile Asn Ile Arg Gly Leu Asn Leu Cys Leu Cys
1               5                   10                  15

Ser Trp Gly Pro Lys Gln Gly Glu Leu Ile Leu Cys Val His Gly Ile
            20                  25                  30

Leu Glu Gln Gly Ala Ala Trp Gly Gln Met Ala Thr Arg Leu Ala Gly
        35                  40                  45

Leu Gly Tyr Arg Val Val Ala Pro Asp Leu Arg Gly Gln Gly Lys Ser
    50                  55                  60

Asp His Val Gly Lys Gly Gly Ser Tyr Asn Leu Ile Asp Phe Leu Ala
65                  70                  75                  80

Asp Leu Asp Ala Ile Ala Asn Ser Leu Thr Asp Gln Pro Phe Thr Leu
                85                  90                  95

Val Gly His Ser Leu Gly Ser Ile Ile Ala Ala Met Phe Thr Ser Ile
            100                 105                 110

Arg Pro Glu Lys Val Lys Asn Leu Val Leu Val Glu Thr Val Leu Pro
        115                 120                 125

Thr Glu Val Ser Gln Thr Asp Ala Val Glu Gln Leu Ala Thr His Leu
    130                 135                 140

Asn Tyr Leu Ala Ser Pro Pro Glu His Pro Val Phe Pro Asp Val Glu
145                 150                 155                 160

Thr Ala Ala Lys Arg Leu Gln Thr Ala Thr Pro Ala Met Ser Glu Ala
                165                 170                 175

Leu Ala Ile Ser Leu Ala Lys Arg Ile Thr Glu Pro Cys Glu Gly Gly
            180                 185                 190

Ile Arg Trp Arg Trp Asp Ser Leu Leu Arg Thr Arg Ala Gly Ile Glu
        195                 200                 205

Phe Asn Gly Ile Asn Arg Ser Arg Tyr Ile Ser Leu Leu Glu Gln Ile
    210                 215                 220

Gln Ala Pro Ile Thr Leu Ile Tyr Gly Asp Asn Ser Asp Phe Asn Arg
225                 230                 235                 240

Pro Glu Asp Leu Gln Ala Gln Lys Ala Met Ser Ala Ala Lys Arg
                245                 250                 255

Ile Ile Leu Lys Gly Gly His Asn Leu His Leu Asp Ala Tyr Glu Gln
            260                 265                 270

Leu Ala Asn Ile Ile Lys Gln Ile Leu Gly Lys Thr Gly Gln Ser Phe
        275                 280                 285

<210> SEQ ID NO 16
<211> LENGTH: 29
<212> TYPE: DNA
<213> ORGANISM: Artificial Sequence
<220> FEATURE:
<223> OTHER INFORMATION: Synthetic nucleotide

<400> SEQUENCE: 16
```

```
ggatccttat tgaggctgtt gatttgtcg                                         29
```

<210> SEQ ID NO 17
<211> LENGTH: 25
<212> TYPE: DNA
<213> ORGANISM: Artificial Sequence
<220> FEATURE:
<223> OTHER INFORMATION: Synthetic nucleotide

<400> SEQUENCE: 17

```
catatgcaag tctctacaac tccct                                             25
```

<210> SEQ ID NO 18
<211> LENGTH: 29
<212> TYPE: DNA
<213> ORGANISM: Artificial Sequence
<220> FEATURE:
<223> OTHER INFORMATION: Synthetic nucleotide

<400> SEQUENCE: 18

```
gcggccgcgg atgttaagat aagtgatgc                                         29
```

<210> SEQ ID NO 19
<211> LENGTH: 323
<212> TYPE: PRT
<213> ORGANISM: Unknown
<220> FEATURE:
<223> OTHER INFORMATION: CurM protein sequence (ST structure)
<220> FEATURE:
<221> NAME/KEY: DOMAIN
<222> LOCATION: (4)..(323)

<400> SEQUENCE: 19

```
Ser Asn Ala Ser Pro Thr Ser Leu Glu Ile Phe Ala Thr Lys Ser Ser
1               5                   10                  15

Pro Ser Gly Asn Ser Ala Arg Pro Ala Ser Val Ser Ser Arg Leu Pro
            20                  25                  30

Gly Ile Ile Phe Ile Leu Ser Ser Pro Arg Ser Gly Ser Thr Leu Leu
        35                  40                  45

Arg Val Met Leu Ala Gly His Ser Ser Leu Phe Ser Pro Pro Glu Leu
    50                  55                  60

His Leu Leu Pro Phe Asn Thr Met Lys Glu Arg Gln Glu Gln Leu Asn
65                  70                  75                  80

Leu Ser Tyr Leu Gly Glu Gly Leu Gln Lys Thr Phe Met Glu Val Lys
                85                  90                  95

Asn Leu Asp Ala Thr Ala Ser Gln Ala Leu Ile Lys Asp Leu Glu Ser
            100                 105                 110

Gln Asn Leu Ser Ile Gln Gln Val Tyr Gly Met Leu Gln Glu Asn Ile
        115                 120                 125

Ala Pro Arg Leu Leu Val Asp Lys Ser Pro Thr Tyr Ala Met Glu Pro
    130                 135                 140

Thr Ile Leu Glu Arg Gly Glu Ala Leu Phe Ala Asn Ser Lys Tyr Ile
145                 150                 155                 160

Tyr Leu Val Arg His Pro Tyr Ser Val Ile Glu Ser Phe Val Arg Met
                165                 170                 175

Arg Met Gln Lys Leu Val Gly Leu Gly Glu Glu Asn Pro Tyr Arg Val
            180                 185                 190

Ala Glu Gln Val Trp Ala Lys Ser Asn Gln Asn Ile Leu Asn Phe Leu
        195                 200                 205
```

```
Ser Gln Leu Glu Pro Glu Arg Gln His Gln Ile Arg Tyr Glu Asp Leu
210                 215                 220

Val Lys Lys Pro Gln Gln Val Leu Ser Gln Leu Cys Asp Phe Leu Asn
225                 230                 235                 240

Val Pro Phe Glu Pro Glu Leu Leu Gln Pro Tyr Gln Gly Asp Arg Met
                245                 250                 255

Thr Gly Gly Val His Gln Lys Ser Leu Ser Ile Ser Asp Pro Asn Phe
                260                 265                 270

Leu Lys His Asn Thr Ile Asp Glu Ser Leu Ala Asp Lys Trp Lys Thr
                275                 280                 285

Ile Gln Leu Pro Tyr Pro Leu Lys Ser Glu Thr Gln Arg Ile Ala Ser
290                 295                 300

Gln Leu Ser Tyr Glu Leu Pro Asn Leu Val Thr Thr Pro Thr Asn Gln
305                 310                 315                 320

Gln Pro Gln

<210> SEQ ID NO 20
<211> LENGTH: 323
<212> TYPE: PRT
<213> ORGANISM: Unknown
<220> FEATURE:
<223> OTHER INFORMATION: CurM protein sequence (ST structure)
<220> FEATURE:
<221> NAME/KEY: DOMAIN
<222> LOCATION: (4)..(323)

<400> SEQUENCE: 20

Ser Asn Ala Ser Pro Thr Ser Leu Glu Ile Phe Ala Thr Lys Ser Ser
1               5                   10                  15

Pro Ser Gly Asn Ser Ala Arg Pro Ala Ser Val Ser Ser Arg Leu Pro
                20                  25                  30

Gly Ile Ile Phe Ile Leu Ser Ser Pro Arg Ser Gly Ser Thr Leu Leu
                35                  40                  45

Arg Val Met Leu Ala Gly His Ser Ser Leu Phe Ser Pro Pro Glu Leu
50                  55                  60

His Leu Leu Pro Phe Asn Thr Met Lys Glu Arg Gln Glu Gln Leu Asn
65                  70                  75                  80

Leu Ser Tyr Leu Gly Glu Gly Leu Gln Lys Thr Phe Met Glu Val Lys
                85                  90                  95

Asn Leu Asp Ala Thr Ala Ser Gln Ala Leu Ile Lys Asp Leu Glu Ser
                100                 105                 110

Gln Asn Leu Ser Ile Gln Val Tyr Gly Met Leu Gln Glu Asn Ile
                115                 120                 125

Ala Pro Arg Leu Leu Val Asp Lys Ser Pro Thr Tyr Ala Met Glu Pro
130                 135                 140

Thr Ile Leu Glu Arg Gly Glu Ala Leu Phe Ala Asn Ser Lys Tyr Ile
145                 150                 155                 160

Tyr Leu Val Arg His Pro Tyr Ser Val Ile Glu Ser Phe Val Arg Met
                165                 170                 175

Arg Met Gln Lys Leu Val Gly Leu Gly Glu Glu Asn Pro Tyr Arg Val
                180                 185                 190

Ala Glu Gln Val Trp Ala Lys Ser Asn Gln Asn Ile Leu Asn Phe Leu
                195                 200                 205

Ser Gln Leu Glu Pro Glu Arg Gln His Gln Ile Arg Tyr Glu Asp Leu
210                 215                 220

Val Lys Lys Pro Gln Gln Val Leu Ser Gln Leu Cys Asp Phe Leu Asn
```

```
                     225                 230                 235                 240

Val Pro Phe Glu Pro Glu Leu Leu Gln Pro Tyr Gln Gly Asp Arg Met
                245                 250                 255

Thr Gly Gly Val His Ala Ala Ser Leu Ser Ile Ser Asp Pro Asn Phe
            260                 265                 270

Leu Lys His Asn Thr Ile Asp Glu Ser Leu Ala Asp Lys Trp Lys Thr
        275                 280                 285

Ile Gln Leu Pro Tyr Pro Leu Lys Ser Glu Thr Gln Arg Ile Ala Ser
    290                 295                 300

Gln Leu Ser Tyr Glu Leu Pro Asn Leu Val Thr Thr Pro Thr Asn Gln
305                 310                 315                 320

Gln Pro Gln

<210> SEQ ID NO 21
<211> LENGTH: 286
<212> TYPE: PRT
<213> ORGANISM: Unknown
<220> FEATURE:
<223> OTHER INFORMATION: CurM protein sequence (TE structure)
<220> FEATURE:
<221> NAME/KEY: DOMAIN
<222> LOCATION: (4)..(286)

<400> SEQUENCE: 21

Ser Asn Ala Met Glu Glu Lys Phe Leu Glu Phe Gly Gly Asn Gln Ile
1               5                   10                  15

Cys Leu Cys Ser Trp Gly Ser Pro Glu His Pro Val Val Leu Cys Ile
            20                  25                  30

His Gly Ile Leu Glu Gln Gly Leu Ala Trp Gln Glu Val Ala Leu Pro
        35                  40                  45

Leu Ala Ala Gln Gly Tyr Arg Val Val Ala Pro Asp Leu Phe Gly His
    50                  55                  60

Gly Arg Ser Ser His Leu Glu Met Val Thr Ser Tyr Ser Ser Leu Thr
65                  70                  75                  80

Phe Leu Ala Gln Ile Asp Arg Val Ile Gln Glu Leu Pro Asp Gln Pro
                85                  90                  95

Leu Leu Leu Val Gly His Ser Met Gly Ala Met Leu Ala Thr Ala Ile
            100                 105                 110

Ala Ser Val Arg Pro Lys Lys Ile Lys Glu Leu Ile Leu Val Glu Leu
        115                 120                 125

Pro Leu Pro Ala Glu Glu Ser Lys Lys Glu Ser Ala Val Asn Gln Leu
    130                 135                 140

Thr Thr Cys Leu Asp Tyr Leu Ser Ser Thr Pro Gln His Pro Ile Phe
145                 150                 155                 160

Pro Asp Val Ala Thr Ala Ala Ser Arg Leu Arg Gln Ala Ile Pro Ser
                165                 170                 175

Leu Ser Glu Glu Phe Ser Tyr Ile Leu Ala Gln Arg Ile Thr Gln Pro
            180                 185                 190

Asn Gln Gly Gly Val Arg Trp Ser Trp Asp Ala Ile Ile Arg Thr Arg
        195                 200                 205

Ser Ile Leu Gly Leu Asn Asn Leu Pro Gly Gly Arg Ser Gln Tyr Leu
    210                 215                 220

Glu Met Leu Lys Ser Ile Gln Val Pro Thr Thr Leu Val Tyr Gly Asp
225                 230                 235                 240

Ser Ser Lys Leu Asn Arg Pro Glu Asp Leu Gln Gln Gln Lys Met Thr
                245                 250                 255
```

```
Met Thr Gln Ala Lys Arg Val Phe Leu Ser Gly Gly His Asn Leu His
            260                 265                 270

Ile Asp Ala Ala Ala Ala Leu Ala Ser Leu Ile Leu Thr Ser
        275                 280                 285

<210> SEQ ID NO 22
<211> LENGTH: 680
<212> TYPE: PRT
<213> ORGANISM: Pseudomonas entomophila L48

<400> SEQUENCE: 22

Glu Ala Arg Glu His Ala Leu Gln Asp Tyr Leu Leu Gly Leu Phe Arg
1               5                   10                  15

Ala Ala Ala Thr Val Ala Thr Glu Ser Leu Asp Val Ser Ala Ser Ile
            20                  25                  30

Glu Ala Trp Gly Leu Asp Ser Leu Val Leu Met Glu Ile Leu Lys Thr
        35                  40                  45

Val Arg Met Asp Leu Gly Leu Ile Ile Tyr Pro Arg Glu Met Tyr Thr
    50                  55                  60

His Ser Thr Leu Ser Gln Phe Ala His Tyr Leu Ala Gly Gln Leu Arg
65                  70                  75                  80

Ala Gly Asn Asp Glu Pro Leu Ala Gly Gly Asp Ser Arg Gln Arg His
                85                  90                  95

Glu Asp Tyr Leu Ser Pro Leu Ala Asp Leu Ala Gly Val Val Gln Asp
            100                 105                 110

Val Ala Asp Arg Val Pro Gly Val Ala Phe Ile Leu Ser Ser Pro Arg
        115                 120                 125

Ser Gly Ser Thr Leu Leu Arg Ala Met Leu Gln Gly His Asp Gln Val
    130                 135                 140

Phe Ala Pro Pro Glu Leu His Leu Leu Gly Tyr Thr Ser Leu Ala Gln
145                 150                 155                 160

Trp His Glu Ala Thr Lys Glu Asn Tyr Phe Asp Gln Gly Leu Gln Arg
                165                 170                 175

Ala Leu Met Glu Leu His Glu Gly Ser Leu Asp Glu Ala Val Ser Leu
            180                 185                 190

Leu Gly Gln Trp Val Asp Gln Asp Ile Ala Val Ala Glu Val Tyr Arg
        195                 200                 205

Phe Met Arg Glu Arg Ser Gly Cys Gly Leu Leu Val Asp Lys Ser Pro
    210                 215                 220

Ser Tyr Ala Ser Asn Pro Lys Ala Leu Leu Gln Ala Glu Leu Ala Phe
225                 230                 235                 240

Asp Lys Pro Arg Tyr Ile His Leu Val Arg Asn Pro Leu Ala Met Ile
                245                 250                 255

Glu Ser Phe Ser Arg Met Arg Met His Lys Leu Leu Gly Gln Gln Asp
            260                 265                 270

Asn Asp Gly Ile Ser Thr Ala Glu Arg Ile Trp Leu Glu Gly Asn Leu
        275                 280                 285

Asn Leu Glu Ala Phe Phe Ala Arg His Val Glu Ala Glu Arg Val Leu
    290                 295                 300

Arg Val Asp Tyr Glu Thr Leu Val Arg Asp Pro Glu Thr Thr Leu Arg
305                 310                 315                 320

Gly Ile Cys Ala Phe Leu Asp Ile Glu Phe Gln Pro Ser Met Thr Met
                325                 330                 335

Pro Tyr Gly Val Gly Arg Met Asn Asp Gly Val Arg Glu Gly Ser Leu
```

```
                    340                 345                 350
Ala Ile Glu Asp Pro Asn Phe Leu Lys Arg Asp Arg Val Asp Ala Ser
                355                 360                 365

Leu Ala Asp Ala Trp Arg His Arg Ser Leu Asp Arg Pro Leu Trp Pro
            370                 375                 380

Gln Thr Val Ala Leu Ala Gly Arg Leu Gly Tyr Asp Glu Ala Leu Pro
385                 390                 395                 400

Ala Ser Ala Lys Arg Asp Glu Ala Arg Gln Thr Leu Asn Val Gln
                405                 410                 415

Ala Gly Glu Val Ser Leu Ser Val Ser Ala Trp Gly Arg Tyr Glu His
            420                 425                 430

Pro Asp Tyr Leu Cys Leu His Gly Leu Leu Asp Gln Ala Thr Val Trp
            435                 440                 445

Asp Asp Ile Ala Gln Asn Leu Tyr Ala Ser Gly Arg Ser Cys Ile Ala
            450                 455                 460

Pro Asp Ile Arg Gly His Gly Leu Ser Gly His Gly Ser Pro Gln Arg
465                 470                 475                 480

Leu Pro Ala Leu Leu Asp Tyr Val Met Asp Thr Asp Ala Val His Arg
                485                 490                 495

Ala Ser Gly Thr Gln Pro Leu Glu Leu Val Ala His Ser Phe Gly Ala
            500                 505                 510

Val Ile Ala Val Ala Tyr Ala Ala Ala Phe Pro Glu Arg Val Lys Lys
            515                 520                 525

Leu Trp Leu Ile Glu Pro Val Leu Leu Ala Glu Lys Arg His Asp Pro
            530                 535                 540

Arg Leu Phe Tyr Arg Glu Met Val Gln Phe Leu Ala Ala Pro His Glu
545                 550                 555                 560

His Leu Pro Leu Gly Ser Leu Gln Gln Ala Ala Glu Arg Ile Arg Ala
                565                 570                 575

Val Ser Ser Phe Leu Thr Gln Asp Arg Ala Cys Glu Leu Ala Glu Arg
            580                 585                 590

Met Thr Thr Val Gly Asp Gly Glu Arg Arg Trp Thr Trp Asp Pro
            595                 600                 605

Arg Leu Arg Phe Arg Ala Gly Leu Gly Leu Gly Leu Asp Arg Asp Thr
610                 615                 620

Tyr Leu Gln Ile Leu His Ala Leu Glu Val Asp Val His Ile Val Phe
625                 630                 635                 640

Gly Arg Asp Ser Arg Ser Asn Arg Arg Lys Asp Ile Glu Leu Gln Ala
                645                 650                 655

Gln Gly Leu Asp Asp Asp Cys Val Thr Phe Ile Asp Gly Gly His Asn
            660                 665                 670

Leu His Leu Gln His Pro Asp Glu
            675                 680

<210> SEQ ID NO 23
<211> LENGTH: 675
<212> TYPE: PRT
<213> ORGANISM: Haliangium ochraceum DSM 14365

<400> SEQUENCE: 23

Glu His Leu Val Glu Leu Leu Asn Leu Glu Pro Glu Ala Val Thr Arg
1               5                   10                  15

Asp Ala Glu Leu Ala Ala Leu Gly Leu Asp Ser Met Leu Ser Leu Glu
            20                  25                  30
```

-continued

```
Leu Gly Glu Ala Ile Arg Asp Glu Leu Glu Leu Thr Val Tyr Pro Arg
         35                  40                  45
Glu Leu Ala Glu Ile Arg Thr Leu Ala Glu Leu Glu Thr Leu Leu Gly
 50                  55                  60
Arg Leu Ala Asp Glu Arg Val Ser Leu Gln Ala Arg Pro Ala Ala Ala
 65                  70                  75                  80
Pro His Asp Ala Glu Pro Glu Leu Gly Ala Pro Leu Glu Pro Glu Leu
                 85                  90                  95
Glu Ser Pro Leu Gly Pro Glu Gly Arg Leu Arg Gly Ala Pro Leu
                100                 105                 110
Arg Glu Gly Pro Val Phe Val Leu Ser Ala Pro Arg Ser Gly Ser Thr
                115                 120                 125
Leu Leu Arg Val Met Leu Ala Gly His Ser Arg Leu Phe Ala Pro Pro
                130                 135                 140
Glu Leu His Leu Leu Val Ala Ala Asp Leu Ala Ala Trp Arg Asp Ser
145                 150                 155                 160
Pro Arg His Leu Asp Glu Gly Leu Leu Glu Ala Leu Val Gln Leu Gly
                165                 170                 175
Gln Gly Thr Pro Glu Asp Val Arg Ala Leu Ile Asp Gln Trp Val Ala
                180                 185                 190
Glu Gly Leu Ser Ile Ala Asp Thr Tyr Arg Arg Leu Met Asp Leu Cys
                195                 200                 205
Ala Pro Leu Ala Leu Val Asp Lys Ser Pro Ser Ser Val Met Asp Arg
                210                 215                 220
Asp Ala Leu Met Arg Val Ala Arg Glu Phe Pro Asp Ala Arg Phe Val
225                 230                 235                 240
Trp Leu Val Arg His Pro Leu Ala Val Val Glu Ser Met Ile Arg Arg
                245                 250                 255
Arg Ile His Ala Val Gly Ala Val Glu Asp Pro Gln Thr Phe Ala
                260                 265                 270
Glu Gln Thr Trp Cys Gln Ser Val Asp Asn Ala Leu Ala Leu Arg Asp
                275                 280                 285
Glu Val Gly Ala Glu Arg Phe Val Thr Leu Arg Tyr Glu Ala Leu Val
                290                 295                 300
Arg Asp Pro Ala Ala Met Ala His Leu Cys Asp Ala Leu Gly Leu
305                 310                 315                 320
Ala Tyr Glu Asp Ala Leu Leu Arg Pro Tyr Glu Gly Glu Arg Met Thr
                325                 330                 335
Asp Gly Leu His Asp Gly Ser Leu Ser Ile Gly Asp Pro Gly Phe Lys
                340                 345                 350
Glu Arg Arg Asp Ile Glu Pro Thr Leu Ala Asp Ala Trp Arg Glu Val
                355                 360                 365
Arg Leu Pro Arg Pro Ser Ala Ala Leu Cys Glu Arg Ala Gln Arg
370                 375                 380
Leu Gly Tyr Pro Val Ala Ser Gln Arg Glu Leu Val Ser Asp Leu Val
385                 390                 395                 400
Leu Ser Thr Trp Gly Pro Glu Ser Gly Asp Ala Val Val Cys Ile His
                405                 410                 415
Gly His Leu Asp Gln Gly Pro Leu Trp Thr Pro Val Ala Asp Arg Leu
                420                 425                 430
Ala Ala Gln Gly Leu Arg Val Leu Ala Pro Asp Leu Arg Gly His Gly
                435                 440                 445
```

```
Arg Ser Pro His Gly Ser Leu Gly Leu Phe Glu His Leu Ala Asp Leu
    450                 455                 460
Asp Ala Leu Leu Ala Ala Gln Ala Pro Gly Arg Ile Val Leu Val Gly
465                 470                 475                 480
His Ser Leu Gly Ala Leu Ile Ala Ala Phe Tyr Ala Ala Ala Arg Pro
                485                 490                 495
Glu Arg Val Ala Lys Leu Val Leu Leu Asp Pro Gly Leu Pro Ser Pro
            500                 505                 510
Leu Ser Glu Gly Pro Gly Ala Ala Leu Ala Arg Ala Leu Asp Arg Arg
        515                 520                 525
Arg Asp Ala Ala His Ala Pro Met Ala Gly Leu Asp Glu Ala Ala Arg
    530                 535                 540
Arg Leu Arg Arg Ala Ile Pro Asp Leu Ser Glu Ala Trp Ser Arg Glu
545                 550                 555                 560
Leu Ala Glu Arg Val Ser Glu Gln Arg Gly Glu His Arg Val Trp Arg
                565                 570                 575
Trp Asp Pro Arg Leu Arg Val Leu Ser Gly Glu Gly Phe Asp Arg Asp
            580                 585                 590
Thr Ala Leu Glu Ile Leu Ala Ser Gln His Ala Pro Val Thr Val Ala
        595                 600                 605
Phe Ala Ala Arg Gly Asp Arg Ala Arg Pro Glu Asp Arg Arg Ala Ile
    610                 615                 620
Glu Asp Ala Leu Gly Ser Ala Thr Phe Val Glu Leu Asp Thr Ala Ser
625                 630                 635                 640
His His Leu His Leu Ala Arg Thr Glu Asp Val Val Gly Leu Ile Val
                645                 650                 655
Glu Arg Ala Ala Ala Gln Ser Thr Met Ser Ser Pro Asp Arg Ser Thr
            660                 665                 670
Asn Ala Pro
        675

<210> SEQ ID NO 24
<211> LENGTH: 688
<212> TYPE: PRT
<213> ORGANISM: Synechococcus PCC7002

<400> SEQUENCE: 24

Ile Asn Leu Glu Ala Ser Gln Arg Ala Asp Tyr Leu Leu Asp Tyr Leu
1               5                   10                  15
Arg Arg Ser Val Ala Gln Ile Leu Lys Leu Glu Ile Glu Gln Ile Gln
            20                  25                  30
Ser His Asp Ser Leu Leu Asp Leu Gly Met Asp Ser Leu Met Ile Met
        35                  40                  45
Glu Ala Ile Ala Ser Leu Lys Gln Asp Leu Gln Met Leu Tyr Pro
    50                  55                  60
Arg Glu Ile Tyr Glu Arg Pro Arg Leu Asp Val Leu Thr Ala Tyr Leu
65                  70                  75                  80
Ala Ala Glu Phe Thr Lys Ala His Asp Ser Glu Ala Ala Thr Ala Ala
                85                  90                  95
Ala Ala Ile Pro Ser Gln Ser Leu Ser Val Lys Thr Lys Lys Gln Trp
            100                 105                 110
Gln Lys Pro Asp His Lys Asn Pro Asn Pro Ile Ala Phe Ile Leu Ser
        115                 120                 125
Ser Pro Arg Ser Gly Ser Thr Leu Leu Arg Val Met Leu Ala Gly His
    130                 135                 140
```

```
Pro Gly Leu Tyr Ser Pro Pro Glu Leu His Leu Pro Phe Glu Thr
145                 150                 155                 160

Met Gly Asp Arg His Gln Glu Leu Gly Leu Ser His Leu Gly Glu Gly
                165                 170                 175

Leu Gln Arg Ala Leu Met Asp Leu Glu Asn Leu Thr Pro Glu Ala Ser
            180                 185                 190

Gln Ala Lys Val Asn Gln Trp Val Lys Ala Asn Thr Pro Ile Ala Asp
        195                 200                 205

Ile Tyr Ala Tyr Leu Gln Arg Gln Ala Glu Gln Arg Leu Leu Ile Asp
    210                 215                 220

Lys Ser Pro Ser Tyr Gly Ser Asp Arg His Ile Leu Asp His Ser Glu
225                 230                 235                 240

Ile Leu Phe Asp Gln Ala Lys Tyr Ile His Leu Val Arg His Pro Tyr
                245                 250                 255

Ala Val Ile Glu Ser Phe Thr Arg Leu Arg Met Asp Lys Leu Leu Gly
            260                 265                 270

Ala Glu Gln Gln Asn Pro Tyr Ala Leu Ala Glu Ser Ile Trp Arg Thr
        275                 280                 285

Ser Asn Arg Asn Ile Leu Asp Leu Gly Arg Thr Val Gly Ala Asp Arg
    290                 295                 300

Tyr Leu Gln Val Ile Tyr Glu Asp Leu Val Arg Asp Pro Arg Lys Val
305                 310                 315                 320

Leu Thr Asn Ile Cys Asp Phe Leu Gly Val Asp Phe Asp Glu Ala Leu
                325                 330                 335

Leu Asn Pro Tyr Ser Gly Asp Arg Leu Thr Asp Gly Leu His Gln Gln
            340                 345                 350

Ser Met Gly Val Gly Asp Pro Asn Phe Leu Gln His Lys Thr Ile Asp
        355                 360                 365

Pro Ala Leu Ala Asp Lys Trp Arg Ser Ile Thr Leu Pro Ala Ala Leu
    370                 375                 380

Gln Leu Asp Thr Ile Gln Leu Ala Glu Thr Phe Ala Tyr Asp Leu Pro
385                 390                 395                 400

Gln Glu Pro Gln Leu Thr Pro Gln Thr Gln Ser Leu Pro Ser Met Val
                405                 410                 415

Glu Arg Phe Val Thr Val Arg Gly Leu Glu Thr Cys Leu Cys Glu Trp
            420                 425                 430

Gly Asp Arg His Gln Pro Leu Val Leu Leu His Gly Ile Leu Glu
        435                 440                 445

Gln Gly Ala Ser Trp Gln Leu Ile Ala Pro Gln Leu Ala Ala Gln Gly
    450                 455                 460

Tyr Trp Val Val Ala Pro Asp Leu Arg Gly His Gly Lys Ser Ala His
465                 470                 475                 480

Ala Gln Ser Tyr Ser Met Leu Asp Phe Leu Ala Asp Val Asp Ala Leu
                485                 490                 495

Ala Lys Gln Leu Gly Asp Arg Pro Phe Thr Leu Val Gly His Ser Met
            500                 505                 510

Gly Ser Ile Ile Gly Ala Met Tyr Ala Gly Ile Arg Gln Thr Gln Val
        515                 520                 525

Glu Lys Leu Ile Leu Val Glu Thr Ile Val Pro Asn Asp Ile Asp Asp
    530                 535                 540

Ala Glu Thr Gly Asn His Leu Thr Thr His Leu Asp Tyr Leu Ala Ala
545                 550                 555                 560
```

```
Pro Pro Gln His Pro Ile Phe Pro Ser Leu Glu Val Ala Ala Arg Arg
                565                 570                 575

Leu Arg Gln Ala Thr Pro Gln Leu Pro Lys Asp Leu Ser Ala Phe Leu
            580                 585                 590

Thr Gln Arg Ser Thr Lys Ser Val Glu Lys Gly Val Gln Trp Arg Trp
        595                 600                 605

Asp Ala Phe Leu Arg Thr Arg Ala Gly Ile Glu Phe Asn Gly Ile Ser
610                 615                 620

Arg Arg Arg Tyr Leu Ala Leu Asp Ile Gln Ala Pro Ile Thr Leu Ile
625                 630                 635                 640

Tyr Gly Asp Gln Ser Glu Phe Asn Arg Pro Ala Asp Leu Gln Ala Ile
                645                 650                 655

Gln Ala Ala Leu Pro Gln Ala Gln Arg Leu Thr Val Ala Gly Gly His
            660                 665                 670

Asn Leu His Phe Glu Asn Pro Gln Ala Ile Ala Gln Ile Val Tyr Gln
        675                 680                 685

<210> SEQ ID NO 25
<211> LENGTH: 697
<212> TYPE: PRT
<213> ORGANISM: Cyanothece PCC 7424

<400> SEQUENCE: 25

Pro Gln Arg Thr Glu Val Leu Ile Thr Tyr Leu Gln Ser Ser Ile Ala
1               5                   10                  15

Arg Ile Leu His Leu Ser Pro Ala Asp Ile Ser Pro Ser Asp Ser Leu
            20                  25                  30

Val Asp Leu Gly Met Asp Ser Leu Met Val Met Glu Ala Ile Asn Thr
        35                  40                  45

Leu Lys Lys Asp Leu Gln Leu Met Leu Tyr Pro Arg Glu Ile Tyr Glu
50                  55                  60

His Pro Lys Ile Glu Ala Leu Ala Thr Tyr Leu Gly Thr Glu Phe Glu
65                  70                  75                  80

Gly Thr His Gly Gln Ser Pro Lys Ser Pro Gln His Asn Pro Gln Lys
                85                  90                  95

Gln Glu Leu Val Val Ser Arg Phe Ser Lys Thr Tyr Gln Pro Leu Thr
            100                 105                 110

Ile Thr Lys Lys Leu Pro Gly Ile Ile Phe Ile Leu Ser Ser Pro Arg
        115                 120                 125

Ala Gly Ser Thr Leu Leu Arg Val Met Phe Ala Gly His Pro Asp Leu
130                 135                 140

Ile Ser Pro Pro Glu Leu His Leu Leu Pro Phe Asn Thr Met Gly Gln
145                 150                 155                 160

Arg Asp Gln Glu Leu Ala Leu Ser Tyr Leu Gly Glu Gly Leu Gln Arg
                165                 170                 175

Ala Phe Met Glu Leu Gly Gly Leu Asp Ser Gln Thr Ser Gln Ser Leu
            180                 185                 190

Ile Glu Glu Leu Ile His Gln Asn Thr Ser Ile Pro Asp Val Tyr Gln
        195                 200                 205

Arg Leu Gln Glu Leu Ala Gly Asn Arg Leu Leu Val Asp Lys Ser Pro
210                 215                 220

Thr Tyr Gly Met Gln Arg Glu Ile Leu Asp Arg Gly Glu Ala Met Phe
225                 230                 235                 240

Glu Gly Ala Lys Tyr Ile His Leu Val Arg His Pro Tyr Ser Val Ile
                245                 250                 255
```

```
Asp Ser Phe Ser Arg Met Arg Met Asp Lys Leu Val Gly Val Ser Gly
            260                 265                 270

Asp Asn Pro Tyr Ser Ile Ala Glu Ser Val Trp Leu Glu Ser Asn Arg
            275                 280                 285

Asn Ile Leu Asp Phe Ser Gln Thr Ile Asp Lys Glu Arg Tyr Tyr Gln
            290                 295                 300

Leu Arg Tyr Glu Asp Leu Val Thr Gln Pro Ser Gln Met Met Arg Ser
305                 310                 315                 320

Leu Cys Glu Phe Leu Asp Ile Pro Phe Asn Ser Ala Leu Leu Asp Pro
                325                 330                 335

Tyr Gln Gly Asp Arg Met Thr Asp Gly Val Tyr Asn Gln Ser Ile Ser
            340                 345                 350

Val Gly Asp Pro Asn Phe Ser Gln Arg Arg Gln Ile Asp Pro Lys Leu
            355                 360                 365

Ala Asp Ala Trp Lys Lys Ile His Leu Pro Gln Pro Leu Gly Asp Thr
            370                 375                 380

Thr Leu Arg Leu Ala Ala Ser Phe Asn Tyr Glu Leu Pro His Glu Thr
385                 390                 395                 400

Val Leu Pro Ser Pro Pro Arg Arg Gly Val Gly Gly Glu Val Ile Ser
                405                 410                 415

Ile Pro Met Gln Glu Asn Tyr Leu Thr Ile Arg Gly Leu Lys Leu Cys
            420                 425                 430

Leu Cys Ser Trp Gly Pro Glu Asp Gly Glu Leu Ile Leu Cys Ile His
            435                 440                 445

Gly Ile Leu Glu Gln Gly Ala Ala Trp Glu Glu Val Ala Thr Arg Leu
450                 455                 460

Ala Gln Lys Gly Tyr Arg Val Ile Ala Pro Asp Leu Arg Gly His Gly
465                 470                 475                 480

Lys Ser Asp His Val Gly Asn Gly Gly Ser Tyr Asn Leu Ile Asp Phe
                485                 490                 495

Leu Gly Asp Leu Asp Ala Ile Ala Thr His Leu Thr Asp Lys Pro Phe
            500                 505                 510

Thr Leu Val Gly His Ser Leu Gly Ser Ile Ile Ala Ala Met Phe Thr
            515                 520                 525

Ser Ile Arg Pro Glu Lys Val Lys His Leu Val Leu Val Glu Thr Val
530                 535                 540

Leu Pro Thr Glu Val His Glu Gly Asp Thr Val Glu Gln Leu Ala Thr
545                 550                 555                 560

His Leu Asn Tyr Leu Ser Ser Pro Pro Lys His Pro Val Phe Pro Asp
                565                 570                 575

Val Glu Thr Ala Ala Lys Arg Leu Gln Thr Ala Thr Pro Ala Met Ser
            580                 585                 590

Glu Gln Leu Ala Met Lys Leu Ala Lys Arg Ile Thr Gln Ala Gly Glu
            595                 600                 605

Gly Gly Ile Gln Trp Arg Trp Asp Ser Leu Leu Arg Thr Arg Ala Gly
            610                 615                 620

Ile Glu Phe Asn Gly Ile Asn Arg Ser Arg Tyr Leu Ser Leu Leu Lys
625                 630                 635                 640

Gln Ile Gln Ala Lys Ile Thr Leu Ile Tyr Gly Asp Gln Ser Asp Phe
                645                 650                 655

Asn Arg Pro Glu Asp Leu Gln Leu Gln Gln Thr Met Ser Gln Ala
            660                 665                 670
```

```
Asn Arg Ile Val Val Asn Gly Gly His Asn Leu His Leu Glu Ala Phe
            675                 680                 685

Glu Glu Leu Ala Asn Ile Ile Asn Gly
        690                 695

<210> SEQ ID NO 26
<211> LENGTH: 705
<212> TYPE: PRT
<213> ORGANISM: Cyanothece PCC 7822

<400> SEQUENCE: 26

Ala Leu Ser Pro Glu Gln Arg Thr Glu Ala Leu Thr Ala Tyr Leu Gln
1               5                   10                  15

Ser Ala Met Ala Gln Ile Met Gln Leu Ser Pro Ser Gln Ile Ser Gly
            20                  25                  30

Glu Asp Ser Leu Leu Asp Ile Gly Met Asp Ser Leu Met Ile Met Glu
        35                  40                  45

Ala Ile Asn Gln Leu Lys Arg Asp Leu Gln Leu Met Leu Tyr Pro Arg
    50                  55                  60

Glu Ile Tyr Gln His Pro Lys Ile Glu Ala Leu Ala Asn Tyr Leu Ala
65                  70                  75                  80

Ala Glu Phe Glu Arg Thr His Gly Lys Gly Gln Ile Pro Val Thr Ser
                85                  90                  95

Lys Gln Glu Leu Val Val Ser Arg Leu Thr Ile Ala Asn Gln Pro Leu
            100                 105                 110

Thr Ile Thr Lys Lys Leu Pro Gly Ile Leu Phe Ile Leu Ser Ser Pro
        115                 120                 125

Arg Ala Gly Ser Thr Leu Leu Arg Val Met Leu Ala Gly His Pro Asp
    130                 135                 140

Leu Ala Ser Pro Pro Glu Leu His Leu Leu Pro Phe Asn Ser Met Gly
145                 150                 155                 160

Gln Arg Asn Gln Glu Leu Ala Leu Ser Tyr Leu Gly Glu Gly Leu Gln
                165                 170                 175

Arg Ala Phe Met Asp Leu Gln Gly Leu Asp Ser Ala Thr Ser Gln Gln
            180                 185                 190

Leu Ile Glu Arg Leu Ile Ala Glu Asp Ile Ser Ile Pro Asp Val Tyr
        195                 200                 205

Glu Met Leu Gln Gln Ser Ala Gly Lys Arg Leu Leu Val Asp Lys Ser
    210                 215                 220

Pro Thr Tyr Gly Met Gln Arg Glu Ile Leu Asp Arg Ala Glu Ala Ile
225                 230                 235                 240

Phe Glu Gly Ala Lys Tyr Ile His Leu Val Arg His Pro Tyr Pro Val
                245                 250                 255

Ile Asp Ser Phe Cys Arg Met Arg Met Asp Lys Leu Val Gly Ser Glu
            260                 265                 270

Gly Asp Asn Pro Tyr Gln Leu Ala Glu Ser Ile Trp Trp Glu Ser Asn
        275                 280                 285

Arg Asn Ile Ile Glu Phe Ser Lys Thr Ile Ser Ser Asp Arg Tyr Tyr
    290                 295                 300

Gln Leu Arg Tyr Glu Asp Leu Val Thr Gln Pro Ser Gln Ala Met Gln
305                 310                 315                 320

Ala Leu Cys Glu Phe Leu Asp Ile Pro Phe Asp Ser Ala Leu Leu Asp
                325                 330                 335

Pro Tyr Gln Gly Gln Arg Met Thr Asp Gly Val Tyr Asn Gln Ser Met
            340                 345                 350
```

```
Ser Val Gly Asp Pro Asn Phe Ser Lys Arg Lys Gln Ile Asp Pro Lys
        355                 360                 365

Leu Ala Asp Ala Trp Lys Asp Ile Gln Leu Pro His Pro Leu Gly Asp
    370                 375                 380

Asn Thr Arg Gln Leu Ala Ile Ser Leu Asn Tyr Pro Leu Pro His Gln
385                 390                 395                 400

Asn Ile Pro Pro Leu Leu Arg Gly Glu Gly Ile Thr Glu Glu Val
                405                 410                 415

His Leu Glu Glu Glu Tyr Ile Asn Ile Arg Gly Leu Asn Leu Cys Leu
                420                 425                 430

Cys Ser Trp Gly Pro Lys Gln Gly Glu Leu Ile Leu Cys Val His Gly
        435                 440                 445

Ile Leu Glu Gln Gly Ala Ala Trp Gly Gln Met Ala Thr Arg Leu Ala
    450                 455                 460

Gly Leu Gly Tyr Arg Val Val Ala Pro Asp Leu Arg Gly Gln Gly Lys
465                 470                 475                 480

Ser Asp His Val Gly Lys Gly Ser Tyr Asn Leu Ile Asp Phe Leu
                485                 490                 495

Ala Asp Leu Asp Ala Ile Ala Asn Ser Leu Thr Asp Gln Pro Phe Thr
            500                 505                 510

Leu Val Gly His Ser Leu Gly Ser Ile Ile Ala Ala Met Phe Thr Ser
        515                 520                 525

Ile Arg Pro Glu Lys Val Lys Asn Leu Val Leu Val Glu Thr Val Leu
    530                 535                 540

Pro Thr Glu Val Ser Gln Thr Asp Ala Val Glu Gln Leu Ala Thr His
545                 550                 555                 560

Leu Asn Tyr Leu Ala Ser Pro Pro Glu His Pro Val Phe Pro Asp Val
                565                 570                 575

Glu Thr Ala Ala Lys Arg Leu Gln Thr Ala Thr Pro Ala Met Ser Glu
            580                 585                 590

Ala Leu Ala Ile Ser Leu Ala Lys Arg Ile Thr Glu Pro Cys Glu Gly
        595                 600                 605

Gly Ile Arg Trp Arg Trp Asp Ser Leu Leu Arg Thr Arg Ala Gly Ile
    610                 615                 620

Glu Phe Asn Gly Ile Asn Arg Ser Arg Tyr Ile Ser Leu Leu Glu Gln
625                 630                 635                 640

Ile Gln Ala Pro Ile Thr Leu Ile Tyr Gly Asp Asn Ser Asp Phe Asn
                645                 650                 655

Arg Pro Glu Asp Leu Gln Ala Gln Gln Lys Ala Met Ser Ala Ala Lys
            660                 665                 670

Arg Ile Ile Leu Lys Gly Gly His Asn Leu His Leu Asp Ala Tyr Glu
        675                 680                 685

Gln Leu Ala Asn Ile Ile Lys Gln Ile Leu Gly Lys Thr Gly Gln Ser
    690                 695                 700

Phe
705
```

METHOD FOR ENZYMATIC PRODUCTION OF DECARBOXYLATED POLYKETIDES AND FATTY ACIDS

CROSS REFERENCE TO RELATED APPLICATIONS

The benefit of U.S. Provisional Application No. 61/227,987, filed Jul. 23, 2009 is claimed, and the disclosure of which is incorporated by reference herein in its entirety.

STATEMENT OF U.S. GOVERNMENTAL INTEREST

This invention was made with government support under DK042303 and CA108874 awarded by the National Institutes of Health. The Government has certain rights in the invention.

BACKGROUND

Curacin A is a mixed polyketide/non-ribosomal peptide with antimitotic properties produced by the marine cyanobacterium *Lyngbya majuscula* (4). The hybrid polyketide synthase (PKS)/non-ribosomal peptide synthase (NRPS) biosynthetic pathways that produces curacin A (5) contains numerous unique chemical steps, many of which have been previously investigated (1,3,6,22). The synthesis of a terminal alkene, instead of the carboxyl typical for this class of linear natural products, and the unique domain arrangement in the terminal PKS module are mysteries yet to be fully elucidated.

In CurM, the terminal module, a sulfotransferase (ST) and thioesterase (TE) domain follow the acyl carrier protein (ACP) (FIG. 1a.) STs catalyze the transfer of a sulfate group from the donor 3'-adenosine 5'-phosphosulfate (PAPS) to a hydroxyl or amine of their acceptor small molecule or protein (10). STs are involved in vital processes such as detoxification, hormone regulation, and signaling and have been studied in a wide variety of organisms. However, the ST in the curacin pathway is the first observation of a ST within a PKS module and contains low (15%) sequence identity to other studied STs.

The TE, although identifiable as a thioesterase, does not resemble any of the previously established fatty acid synthase (FAS), PKS or NRPS TE families (24). Many PKS offloading TEs have been studied to date including the TEs of the pikromycin synthase (Pik) (25,26) and erythromycin synthase (DEBS) (27) pathways. PKS offloading TEs typically perform either hydrolysis to produce a carboxylic acid or catalyze the attack of an intramolecular hydroxyl to form a macrolactone. These TEs are dimers, with two N-terminal alpha helices forming a lid-to-lid dimer interface, and adopt the α/β hydrolase fold characteristic of some serine hydrolases. Access to the classic nucleophile-His-acid catalytic triad active site is restricted by a narrow tunnel formed by a closed lid. Many PKS and NRPS pathways also include a second non-modular thioesterase called a TE II (in addition to an offloading TE, also known as TE I), which performs an editing function within the pathway. The curacin TE shows low similarity to sequences in all parts of the phylogenic tree (24), also pointing the need to more closely study curacin TE to understand its activity.

SUMMARY

Disclosed herein are methods of preparing alkenes by decarboxylation of beta-sulfate carboxylic acids or carboxylic acid derivatives. More specifically, disclosed herein are methods of preparing alkenes by decarboxylative elimination to form the alkene.

Thus, in one aspect, provided herein is a method of contacting a beta-sulfate carboxylic acid or carboxylic acid derivative with a TE such that the TE mediates decarboxylative elimination of the beta-sulfate carboxylic acid or carboxylic acid derivative to form the alkene. In some cases, the TE comprises an amino acid sequence of SEQ ID NO: 3 or an enzymatically active fragment thereof which maintains the TE activity of SEQ ID NO: 3.

The method disclosed herein can further comprise contacting a beta-hydroxy carboxylic acid or carboxylic acid derivative with a sulfonating reagent and a sulfotransferase (ST) such that the ST mediates the formation of the beta-sulfate carboxylic acid or carboxylic acid derivative. In some cases, the ST comprises an amino acid sequence of SEQ ID NO: 4, or an enzymatically active fragment thereof which maintains the ST activity of SEQ ID NO: 4. The ST and TE can be in the same polypeptide or in different polypeptides.

The carboxylic acid derivative can comprise a carboxylic acid conjugated to an acyl carrier protein (ACP). In some cases, the ACP comprises an amino acid sequence SEQ ID NO: 5 or active fragment thereof. In various embodiments, the ACP and at least one of the TE and ST (e.g., ACP and TE and/or ACP and ST) are in the same polypeptide. In some cases, the ACP, TE and ST are all in the same polypeptide. In some embodiments, the ACP, TE and ST are all in the same polypeptide and that polypeptide comprises an amino acid sequence of SEQ ID NO: 1.

In some embodiments, the alkene is a terminal alkene. In various cases, the alkene has a structure of formula (II) and the beta-sulfate or beta-hydroxy carboxylic acid or carboxylic acid derivative has a structure of formula (I):

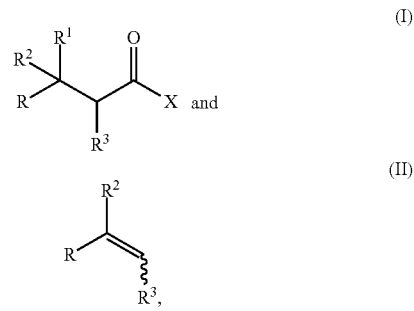

wherein R is alkyl, heteroalkyl, cycloalkyl, aryl, heteroaryl, heterocycloalkyl, alkenyl, or alkynyl and can be optionally substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

$R^2$ and $R^3$ are each independently selected from the group consisting of hydrogen, alkyl, heteroalkyl, cycloalkyl, aryl, heteroaryl, heterocycloalkyl, alkenyl, or alkynyl and can be optionally substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

X is OH, SH, $OR^2$, or $SR^2$;

$R^1$ is hydroxy or sulfate; and $R^2$ is optionally substituted alkyl, optionally substituted alkenyl, or a peptide. One example of a peptide of formula (I) is an ACP.

In another aspect, disclosed herein is an isolated crystalline form of a sulfotransferase (ST) polypeptide comprising an amino acid sequence of SEQ ID NO: 19, a space group P2$_1$2$_1$2$_1$, unit cell parameters of a=45.8 Å, b=67.3 Å, c=118.0 Å, β=β=γ=90°, and one ST molecule in an asymmetric unit.

In yet another aspect, disclosed herein is an isolated crystalline form of a thioesterase (TE) polypeptide comprising an amino acid sequence of SEQ ID NO: 21, a space group P2$_1$, unit cell parameters of a=74.5 Å, b=86.9 Å, c=87.6 Å, α=γ=90°, β=90.8°, and four TE molecules in an asymmetric unit.

In still another aspect, disclosed herein is an isolated thioesterase (TE) polypeptide comprising an amino acid sequence that is greater than 75% identical to SEQ ID NO: 3 and exhibits TE activity. In some cases, the sequence is greater than 90%, greater than 95%, or greater than 98% identical to SEQ ID NO: 3. In a specific embodiment, the sequence is SEQ ID NO: 3.

Further disclosed herein is a polynucleotide encoding an isolated TE polypeptide disclosed herein. Also disclosed herein is a vector comprising such a polynucleotide, and a host cell comprising the polynucleotide or vector.

In another aspect, provided herein is a method of preparing a disclosed isolated TE polypeptide comprising culturing a host cell as disclosed herein and recovering the polypeptide.

In a further aspect, the invention provides an antibody specifically reactive with a polypeptide described herein.

BRIEF DESCRIPTION OF THE FIGURES

FIG. 12 shows the sequence alignment of tandem ACP-ST-TE domains encompassing CurM residues 1505-2211 of SEQ ID NO: 1. Other species used in the alignment are: *Pseudomonas entomophila* L48(Accession number: YP_610919) (SEQ ID NO: 22), *Haliangium ochraceum* DSM 14365(YP_003265308) (SEQ ID NO: 23), *Synechococcus* PCC7002(YP_001734428) (SEQ ID NO: 24), *Cyanothece* PCC 7424(YP_002377174) (SEQ ID NO: 25), *Cyanothece* PCC 7822(ZP_03153601) (SEQ ID NO: 26).

DETAILED DESCRIPTION

Figure 1:
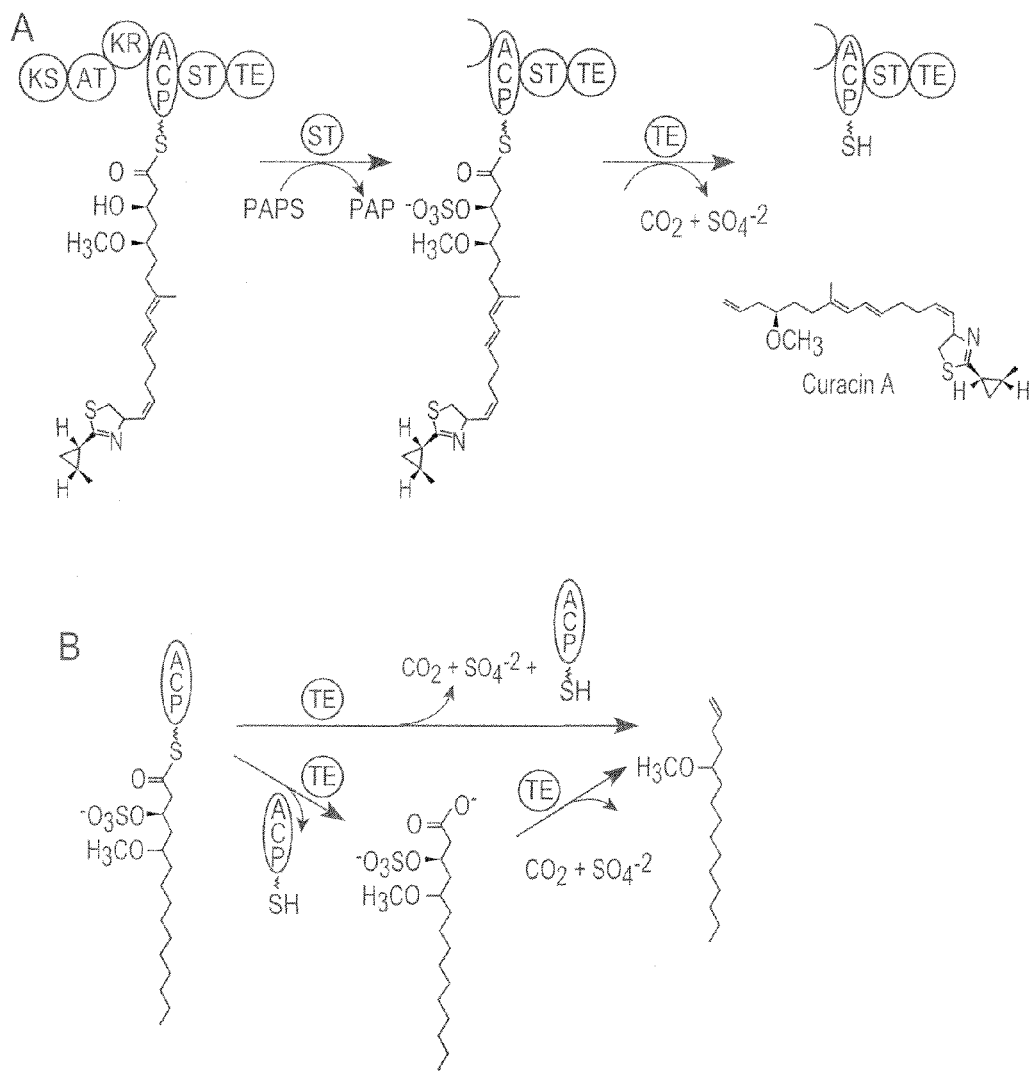
FIG. 1 shows the chain termination of the curacin A PKS/NRPS biosynthetic pathway; (a) offloading performed by the final module, CurM (ACP, acyl carrier protein; AT, acyltransferase; KR, ketoreductase; KS ketosynthase; ST sulfotransferase; TE thioesterase; PAPS, 3'-adenosine 5'-phosphosulfate); (b) experimental scheme used in TE activity assay; holo ACP is detected by a change in retention time during HPLC.

Disclosed herein are methods of synthesizing an alkene, e.g., a terminal alkene, using natural or engineered enzymes. In particular, disclosed herein are methods of preparing an alkene from a beta-sulfate (OSO$_3^-$) carboxylic acid or carboxylic acid derivative by contacting the beta-sulfate carboxylic acid or carboxylic acid derivative with a thioesterase (TE) or fragment of a TE having TE enzymatic activity to form the alkene by decarboxylative elimination. The method can further comprise formation of the beta-sulfate carboxylic acid or carboxylic acid derivative by contacting a beta-hydroxy carboxylic acid or carboxylic acid derivative with a sulfotransferase (ST) or fragment of a ST having ST enzymatic activity to form the beta-sulfate carboxylic acid or carboxylic acid derivative thereof. Any beta-hydroxy (or sulfate) carboxylic acid A representative beta-hydroxy (sulfate) carboxylic acid or derivative thereof is illustrated in Formula (I), and can form an alkene of Formula (II):

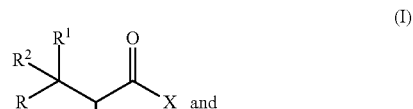

where R is alkyl, heteroalkyl, cycloalkyl, aryl, heteroaryl, heterocycloalkyl, alkenyl, or alkynyl, and optionally can be substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

$R^2$ and $R^3$ are each independently selected from the group consisting of hydrogen, alkyl, heteroalkyl, cycloalkyl, aryl, heteroaryl, heterocycloalkyl, alkenyl, or alkynyl and can be optionally substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

X is OH, SH, $OR^2$, or $SR^2$;

$R^1$ is hydroxy or sulfate (e.g., $OSO_3^-$); and $R^2$ is optionally substituted alkyl, optionally substituted alkenyl, or a peptide, such as, e.g., an ACP.

"Decarboxylative elimination" used herein refers to elimination of a carboxylic acid or derivative thereof and optionally a beta-hydroxy (or sulfate) moiety to form an alkene. This process can be illustrated in the following reaction scheme:

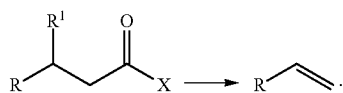

A "carboxylic acid derivative" as used herein refers to a moiety such as an ester, a thioester, an amide, or the like.

The term "alkyl" used herein refers to a saturated or unsaturated straight or branched chain hydrocarbon group of one to ten carbon atoms, including, but not limited to, methyl, ethyl, n-propyl, isopropyl, n-butyl, isobutyl, tert-butyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halo, aryl, heteroaryl, cycloalkyl, heterocycloalkyl, and amino. It is specifically contemplated that in the analogs described herein the alkyl group consists of 1-40 carbon atoms, 1-25 carbon atoms, 1-15 carbon atoms, 1-12 carbon atoms, 1-10 carbon atoms, 1-8 carbon atoms, and 1-6 carbon atoms. "Heteroalkyl" is defined similarly as alkyl, except the heteroalkyl contains at least one heteroatom independently selected from the group consisting of oxygen, nitrogen, and sulfur.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, $C(O)NH_2$, $NH_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "alkenyl" used herein refers to a straight or branched chain hydrocarbon group of two to thirty, or more, carbon atoms containing at least one carbon double bond including, but not limited to, 1-propenyl, 2-propenyl, 2-methyl-1-propenyl, 1-butenyl, 2-butenyl, and the like. "Alkynyl" refers to a straight or branched chain hydrocarbon group of two to thirty, or more, carbon atoms containing at least one carbon triple bond.

The term "halo" used herein refers to fluoro, chloro, bromo, or iodo.

The term "alkylene" used herein refers to an alkyl group having a substituent. For example, the term "alkylene aryl" refers to an alkyl group substituted with an aryl group. The alkylene group is optionally substituted with one or more substituent previously listed as an optional alkyl substituent. For example, an alkylene group can be —$CH_2CH_2$—.

As used herein, the term "alkenylene" is defined identical as "alkylene," except the group contains at least one carbon-carbon double bond.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "alkoxy" used herein refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "amino" as used herein refers to $NR_2$, where R is independently hydrogen, optionally substituted alkyl, optionally substituted heteroalkyl, optionally substituted cycloalkyl, optionally substituted heterocycloalkyl, optionally substituted aryl or optionally substituted heteroaryl. In some cases, R is independently hydrogen or alkyl. Non-limiting examples of amino groups include $NH_2$ and $N(CH_3)_2$.

The term "amido" as used herein refers to —$C(O)NH_2$, —$C(O)NR_2$, —NRC(O)R or —NHC(O)H, where each R is independently hydrogen, optionally substituted alkyl, optionally substituted heteroalkyl, optionally substituted cycloalkyl, optionally substituted heterocycloalkyl, optionally substituted aryl or optionally substituted heteroaryl. In some cases, the amido group is —NHC(O)alkyl or —NHC(O)H. A non-limiting example of an amido group is —NHC(O)$CH_3$.

The term "carboxy" or "carboxyl" used herein refers to —COOH or its deprotonated form —$COO^-$. Carboxyalkyl refers to optionally substituted alkyl or alkenyl groups having a carboxy moiety. Examples include, but are not limited to, —$CH_2COOH$, —$CH_2CH(COOH)CH_3$, and $CH_2CH_2CH_2COOH$.

The TE, ST, and/or ACP can be in separate polypeptides or in the same polypeptide. For example, CurM (SEQ ID NO: 1—amino acid sequence; SEQ ID NO: 2—nucleic acid sequence) comprises a TE, ST, and ACP domain at residues 1929 to 2211 (TE) (SEQ ID NO: 3); 1622 to 1905 (ST) (SEQ ID NO: 4); and 1504 to 1592 (ACP) (SEQ ID NO: 5).

It is contemplated that longer or indeed shorter peptides of TE, ST, and/or ACP also may prove useful. Thus, also contemplated are peptides that comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90 or more amino acids from the TE, ST, and/or ACP peptide added to its N-terminus. For example, the amino acid at position 1928 of SEQ ID NO: 1, 1621 of SEQ ID NO:1, and/or 1503 of SEQ ID NO:1 could be added to a peptide described herein, if the addition of 1 amino acid to the N-terminus of a peptide sequence described herein is desired. Similarly, the amino acids from any one of positions 1502, 1501, 1500, 1499, 1498, 1497, 1496, 1495, 1494, 1489, or 1484 to 1503 of SEQ ID NO: 1 could be added to a peptide described herein if the addition of 2, 3, 4, 5, 6, 7, 8, 9, 10, 15, or 20 amino acids, respectively, to the N-terminus of the ACP peptide is desired. The amino acids from any one of positions 1620, 1619, 1618, 1617, 1616, 1615, 1614, 1613, 1612, 1607, or 1602 to 1621 of SEQ ID NO: 1 could be added to a peptide described herein if the addition of 2, 3, 4, 5, 6, 7, 8, 9, 10, 15, or 20 amino acids, respectively, to the N-terminus of the ST peptide is desired. The amino acids from any one of positions 1927, 1926, 1925, 1924, 1923, 1922, 1921, 1920, 1919, 1914, or 1909 to 1928 of SEQ ID NO: 1 could be added to a peptide described herein if the addition of 2, 3, 4, 5, 6, 7, 8, 9, 10, 15, or 20 amino acids, respectively, to the N-terminus of the TE peptide is desired.

In some embodiments, a peptide described herein comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90 or more amino acids added to its C-terminus. These amino acids can be from the native CurM sequence or can be unnatural additional amino acids added that still at least substantially maintain the enzymatic activity of the ACP, ST, and/or TE. For example, the amino acid at position 1593 of SEQ ID NO: 1 and/or 1906 of SEQ ID NO:1 could be added to a peptide described herein to the ACP and/or ST peptide, respectively. Similarly, the amino acids from 1593 to any one of positions 1594, 1595, 1596, 1597, 1598, 1599, 1600, 1601, 1602, 1607, or 1612 of SEQ ID NO: 1 could be added to a peptide described herein if the addition of 2, 3, 4, 5, 6, 7, 8, 9, 10, 15, or 20 amino acids, respectively, to the C-terminus of the ACP peptide is desired. The amino acids from 1906 to any one of positions 1607, 1908, 1909, 1910, 1911, 1912, 1913, 1914, 1915, 1920, or 1925 of SEQ ID NO: 1 could be added to a peptide described herein if the addition of 2, 3, 4, 5, 6, 7, 8, 9, 10, 15, or 20 amino acids, respectively, to the C-terminus of the ST peptide is desired. Since the CurM protein (SEQ ID NO: 1) ends with the TE peptide, non-native amino acids can be added to the TE peptide C-terminus, e.g., 1, 2, 3, 4, 5, 6, 7, 8, 9, 10, 16, or 20 amino acids.

In some embodiments, the addition of amino acids to both the N- and C-termini of a peptide described herein is contemplated.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications can include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and/or transfer-RNA mediated addition of amino acids to protein such as arginylation. (See Proteins—Structure and Molecular Properties 2nd Ed., T. E. Creighton, W. H. Freeman and Company, New York (1993); Posttranslational Covalent Modification of Proteins, B. C. Johnson, Ed., Academic Press, New York, pp. 1-12 (1983)).

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. However, the term "purified" also includes nucleic acids that have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein or produced from a DNA construct by enzymes (transcribed by an RNA polymerase and translated by ribosomes, tRNAs and accessory proteins outside a cell). "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when the RNA polymerase that initiates transcription at the promoter will transcribe the coding sequence into mRNA.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 g of plasmid or DNA fragment is used with about 2 units of enzyme in about 20 1 of buffer solution. For the purpose of isolating DNA fragments for plasmid construction, typically 5 to 50 g of DNA are digested with 20 to 250 units of enzyme in a larger volume. Appropriate buffers and substrate amounts for particular restriction enzymes are specified by the manufacturer. Incubation times of about 1 hour at 37 C are ordinarily used, but may vary in accordance with the supplier's instructions. After digestion the gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acid sequences or polypeptides, refers to two or more sequences that have greater than 60%, greater than 70%, greater than 80%, greater than 90%, greater than 91%, greater than 92%, greater than 93%, greater than 94%, greater than 95%, greater than 96%, greater than 97%, greater than 98%, or greater than 99% nucleotide or amino acid residue identity, when compared and aligned for maximum correspondence, as measured using one of the known sequence comparison algorithms or by visual inspection. The substantial identity can exists over a region of at least about 100 residues, and in some cases, the sequences are substantially identical over at least about 150-200 residues. In some embodiments, the sequences are substantially identical over the entire length of the nucleotide or polypeptide.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a haloalkane dehalogenase polypeptide, resulting in modification of the structure of the polypeptide, without significantly altering its biological activity. Modified polypeptide sequences of the invention can be assayed for haloalkane dehalogenase biological activity by any number of methods, including contacting the modified polypeptide sequence with an haloalkane dehalogenase substrate and determining whether the modified polypeptide decreases the amount of specific substrate in the assay or increases the bioproducts of the enzymatic reaction of a functional haloalkane dehalogenase polypeptide with the substrate.

"Fragments" as used herein are a portion of a naturally occurring or recombinant protein that can exist in at least two different confirmations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are greater than about 50%, but more typically greater than about 70%, greater than about 85%, or greater than about 90% identical. Fragments that have different three-dimensional structures as the naturally occurring protein are also included. An example of this, is a "pro-form" molecule, such as a low activity proprotein that can be modified by cleavage to produce a mature enzyme with significantly higher activity.

"Enzymatically active fragment" refers to a fragment of, e.g., TE, ST, and ACP, which retains some or all of the enzymatic activity of the full TE, ST, and/or ACP sequence. The activity of the fragment can be for example, at least 30%, at least 40%, at least 50%, at least 60%, at least 70%, at least 80%, at least 90%, or at least 95% the activity of the original sequence.

CurM

CurM was sequenced and additional parts of the 3' flanking region of the cur cluster in another cosmid (pLM14), from the *L. majuscula* genomic DNA library (14), and compared the data with those from a *L. majuscula* genome sequencing project. It revealed that the 3' end of the deposited cur gene cluster (5) starting from the middle of curM TE region was indeed chimeric. The revised gene cluster lacks "curN", and a complete TE domain is encoded by the 3' end of curM (5). The adjacent downstream genes show high homology to tRNA 2-selenouridine synthase (ATPase) and adenylate/guanylate cyclase (Cy), and are not likely involved in curacin biosynthesis (FIG. 1A). Thus, curM now appears to mark the 3'-end boundary of the cur, gene cluster, and the ST-TE di-domain presumably functions as the chain termination module.

To biochemically assess the ST-TE mediated chain termination process, CurM ACP, ST and TE were cloned and overexpressed as soluble single domain constructs. ST was eluted as a monomer and TE as a dimer from an analytical size-exclusion column. ACP was overexpressed in the apo form in order to generate ACP-linked substrates. A simplified model substrate, 3-hydroxy-5-methoxytetradecanoyl-CoA (1-CoA, FIG. 1B) was designed to mimic the full-length chain intermediate tethered to CurM ACP (FIG. 1B). Two β-hydroxyl enantiomers, (3S)-1-CoA and (3R)-1-CoA, were synthesized to test the stereoselectivity of the enzymes. The ACP-linked substrates were generated by loading the acyl-CoA substrates to the apo ACP by using the highly flexible *Streptomyces verticillus* Svp phosphopantetheinyltransferase (15).

With the soluble enzymes and model substrates in hand, the key issues in curacin A chain termination were investigated, including, 1) whether the sulfonated carboxylic acid (2, FIG. 1B) will be generated; 2) the timing of the putative ST sulfonation and TE hydrolysis (FIG. 1B); 3) whether 2 can lead to the formation of 3 via a decarboxylative elimination mechanism (FIG. 1B).

Polyketide Chain Release by TE hydrolysis.

Figure 2:
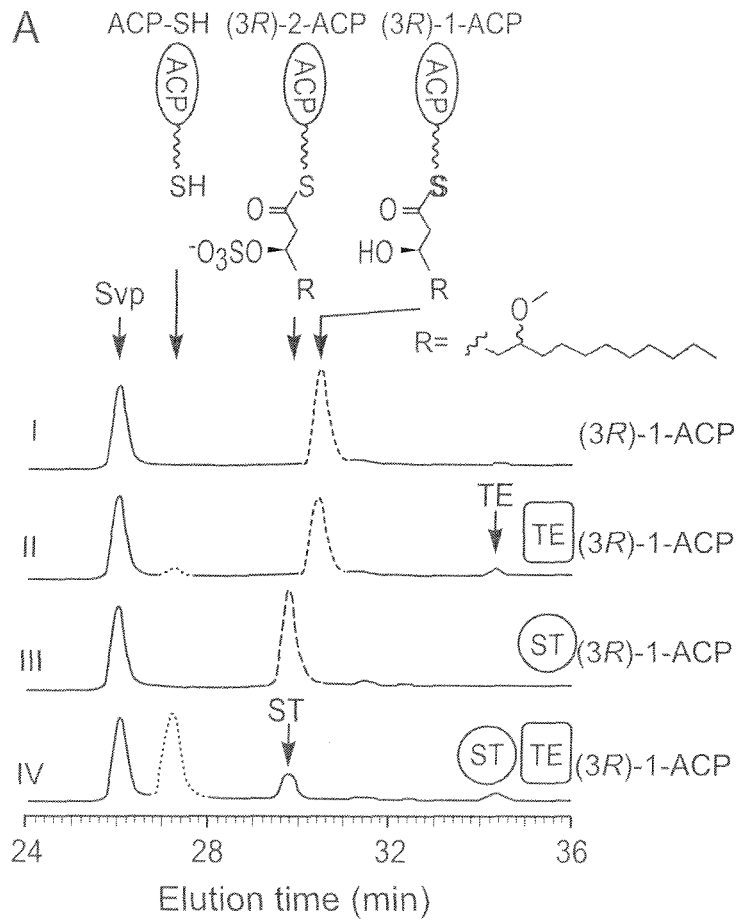
FIG. 2 shows liquid chromatography (HPLC) and Fourier transform ion cyclotron resonance mass spectrometry (FTICR-MS) analysis for ST and TE reactions with ACP-linked substrates: (A) HPLC analysis of ST and TE reactions with (3R)-1-ACP after 30 min; (B) Partial FTICR mass spectra (+12 charge state) for the ACP-linked substrate and products, with the ACP species with and without an N-terminal methionine indicated by black diamond.
Figure 2:
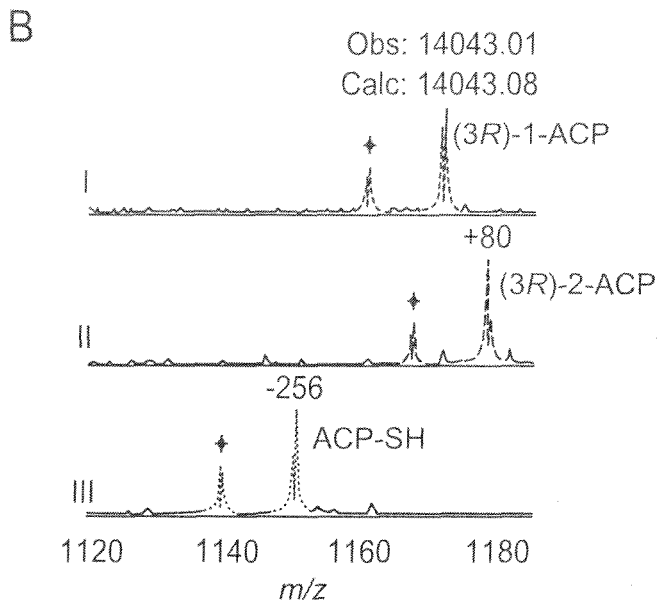
Figure 5:
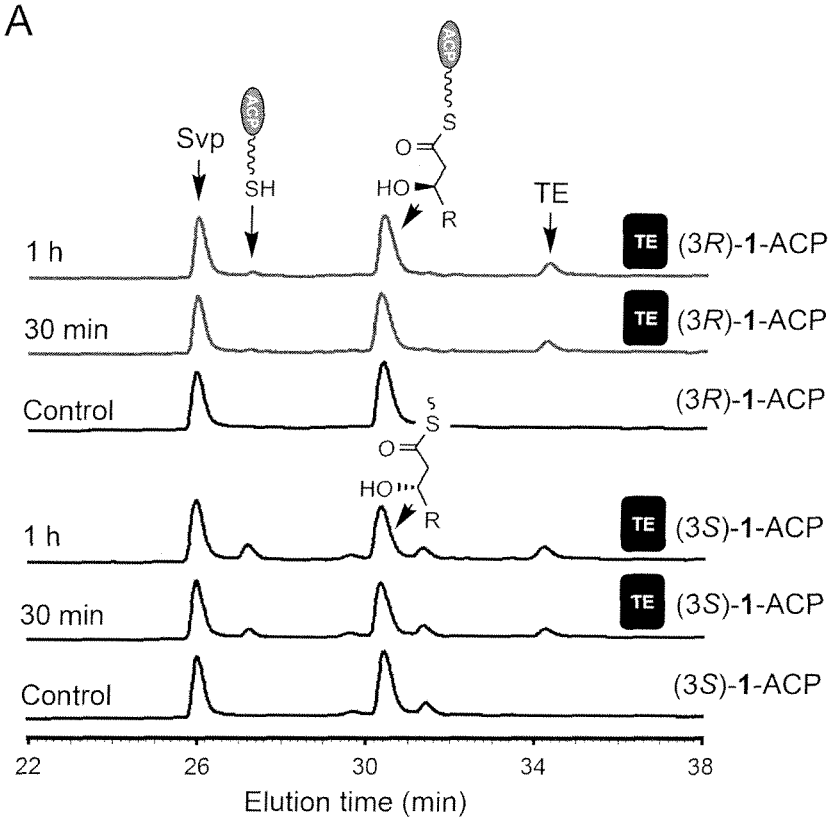
FIG. 5 shows (A) HPLC analysis of TE stereoselectivity using ACP-linked substrates and (B) HPLC analysis of TE stereoselectivity using CoA-linked substrates.
Figure 5:
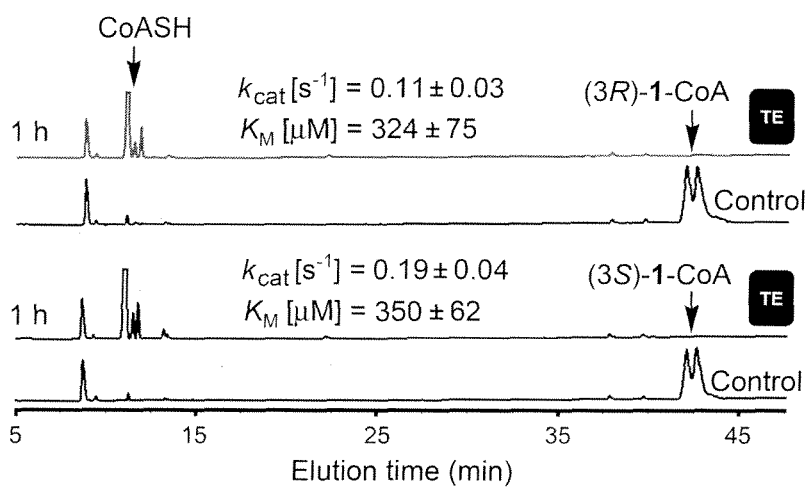

First, it was investigated whether the CurM TE exhibits canonical hydrolysis activity to cleave the thioester bond. (3S)-1-ACP and (3R)-1-ACP were prepared as the TE substrates to test its stereoselectivity for the β-hydroxyl group. The reactions were analyzed by reverse-phase HPLC, and the separated ACP fractions were examined by Fourier transform ion cyclotron resonance mass spectrometry (FTICR-MS) and infrared multiphoton dissociation (IRMPD) (16) techniques. In addition, the chain-release products were detected by LC-MS and confirmed by co-injection with authentic standards. Both of the acyl groups were found to be hydrolyzed from (3S)-1-ACP and (3R)-1-ACP with low efficiency (FIGS. 2A ii, 2B iii, 3A ii and 5A). However, TE-catalyzed hydrolysis of (3S)-1-ACP was about 5-fold faster than with (3R)-1-ACP (FIG. 5A). In addition, the steady-state kinetic analysis using the CoA-linked substrates confirmed that (3S)-1 is the preferred substrate for TE (FIG. S2B). However, based on bioinformatic analysis of PKS ketoreductase (KR) sequences (17), the CurM KR was predicted to reduce the β-keto to a (R)-β-hydroxyl group in the full-length chain intermediate.

On-Assembly-Line Sulfonation by CurM ST.

Figure 6:
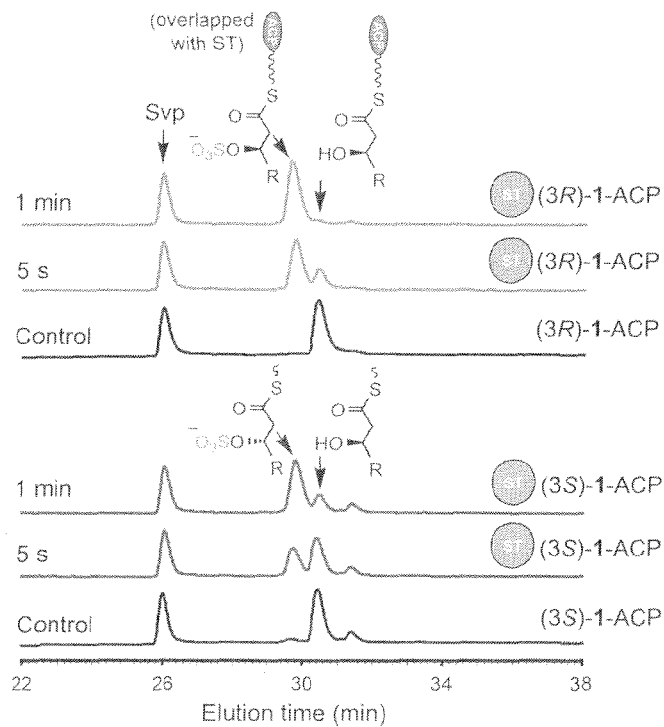
FIG. 6 shows HPLC analysis of the ST stereoselectivity using ACP-linked substrates.

Based on the known mechanism of ST enzyme function, CurM ST was predicted to bind to PAPS, and transfer a sulfonate moiety to the β-hydroxyl group of the intermediate tethered to or released from CurM ACP (FIG. 1B). First, the ST substrate was identified by testing the sulfonation of 1 and 1-ACP. The sulfonation of 1 was analyzed by LC-MS, and that of 1-ACP was examined by HPLC and FTICR-MS. No substrate conversion was observed for 1 in the presence of ST and PAPS. In contrast, complete conversion of (3R)-1-ACP was determined by HPLC (FIG. 2A iii), and the product with an 80-dalton mass addition was confirmed to be (3R)-2-ACP by FTICR-MS (FIG. 2B ii). Notably, for (3R)-1-ACP substrate, the ST catalyzed sulfonation was about 1000-fold faster than TE hydrolysis. Likewise, the stereoselectivity of ST for the β-hydroxyl group was determined by comparing the sulfonation efficiency of (3S)-1-ACP and (3R)-1-ACP. Under the same reaction condition, ST sulfonation with (3R)-1-ACP was about 2.5-fold faster than with (3S)-1-ACP (FIG. 6). Thus, CurM ST stereoselectivity is consistent with the predicted formation of a (R)-β-hydroxyl group by CurM KR. The catalytic efficiency and substrate preference of ST and TE revealed in these experiments provide convincing evidence that ST sulfonation precedes the TE hydrolysis step.

Terminal Olefin Formation via Decarboxylative Elimination in the Cur Pathway.

Figure 7:
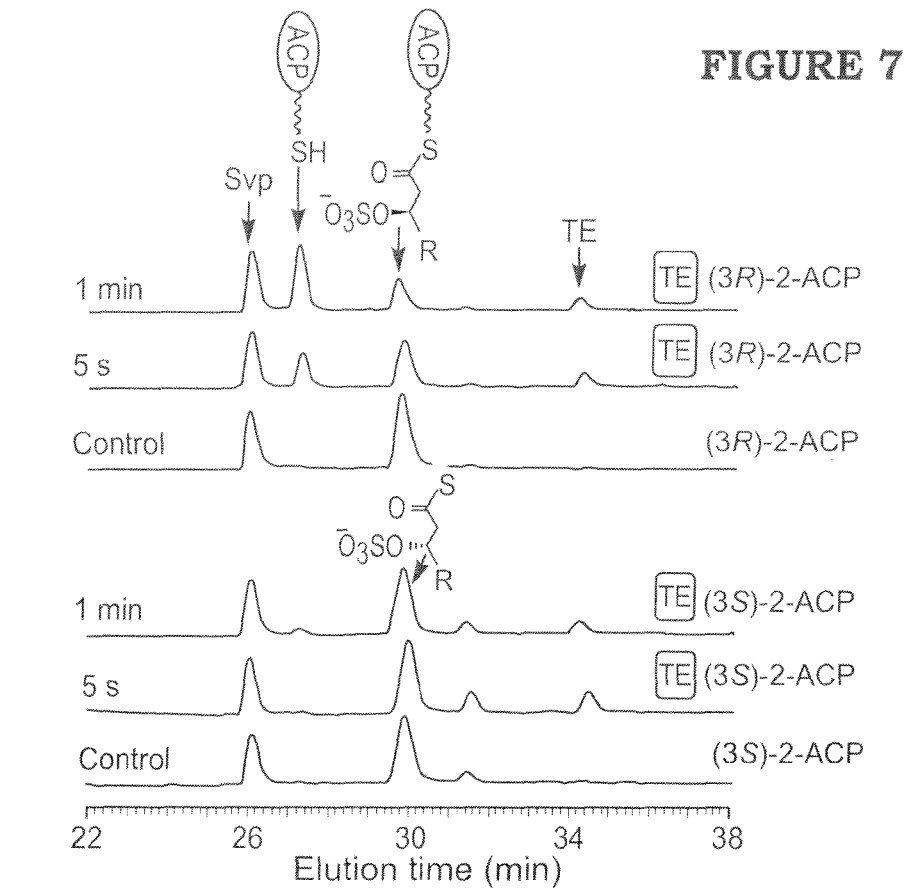
FIG. 7 shows HPLC analysis of TE stereoselectivity using sulfonated ACP substrates.

With the order of the ST and TE reactions established for the acyl-ACP intermediate, the next investigation was to couple the two reactions in one pot. When (3R)-1-ACP was treated with both ST and TE, complete release of the acyl chain from CurM ACP was observed by HPLC (FIG. 2A iv), and confirmed by FTICR-MS (FIG. 2B iii) and IRMPD. Under the same reaction conditions, it was discovered that the CurM TE catalyzed hydrolysis reaction with sulfonated product (3R)-2-ACP was about 800-fold faster than with (3R)-1-ACP. Moreover, TE catalyzed hydrolysis of (3R)-2-ACP was about 120-fold faster than (3S)-2-ACP (FIG. 7). These results further corroborated the timing and stereoselectivity of the ST sulfonation and TE hydrolysis reactions.

Figure 3:
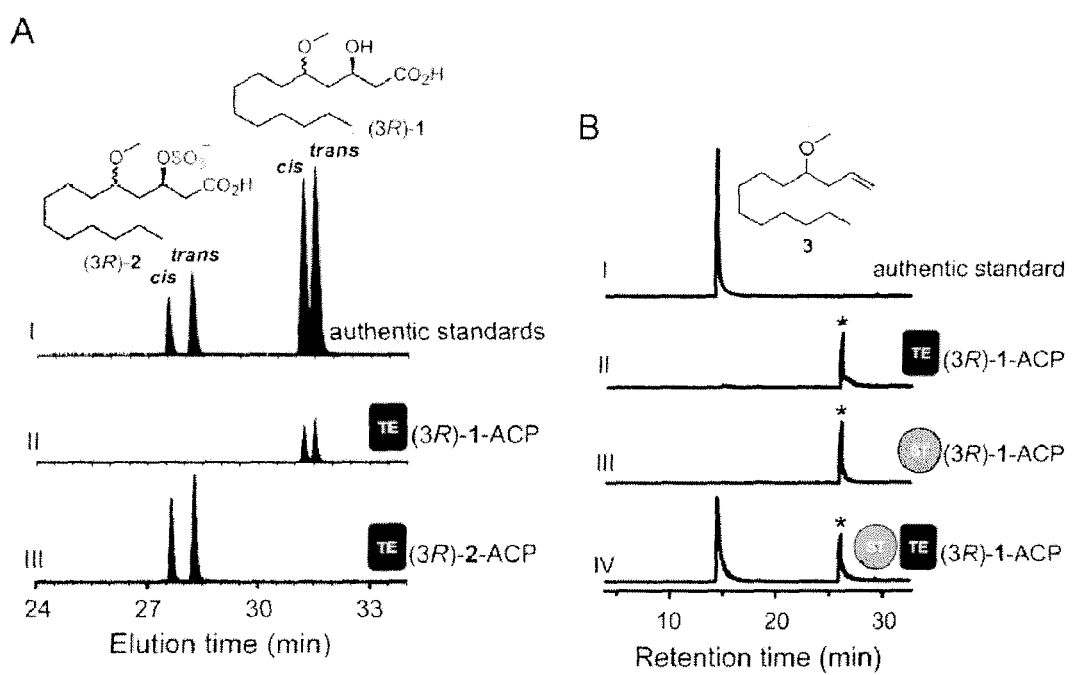
FIG. 3 shows LC-MS and GC-MS analysis of products from ST and TE reactions: (A) LC-MS chromatograms (273.2 and 353.1 mass range) of TE reactions with (3R)-1-ACP or (3R)-2-ACP; (B) GC-MS chromatograms of ST and TE reactions (asterisks denote unidentified species).

Next, experiments were performed to assess whether the proposed sulfonated intermediate (3R)-2 (FIG. 3A) is released following hydrolysis of (3R)-2-ACP, or whether formation of 3 (FIG. 3B) occurs directly by a coordinated decarboxylative elimination process. First, the ST-TE coupled reactions with (3R)-1-ACP were analyzed by LC-MS and a single product was confirmed to be (3R)-2 by co-injection with the corresponding authentic standard (FIG. 3A iii). Due to the expected volatility of 3, the contents of the coupled reaction were extracted with hexane and analyzed by GC-MS. A second product was thus detected and confirmed to be 3 by co-injection with the corresponding authentic standard (FIG. 3B iv). It was found that 2 was relatively stable in the reaction mixture, and was not spontaneously converted to 3. To determine which enzyme catalyzes the decarboxylative elimination of 2, authentic (e.g. synthetic) (3R)-2 was separately treated with CurM ST or TE, and a small amount of 3 was observed only for the TE reaction (about 2% conversion in 1 hour). Under the same conditions, the TE reaction with (3R)-2-ACP leading to 3 was more efficient than with (3R)-2 (about 20% conversion in 5 min), suggesting that the decarboxylative elimination is likely coupled with hydrolysis in the TE active site.

Figure 4:
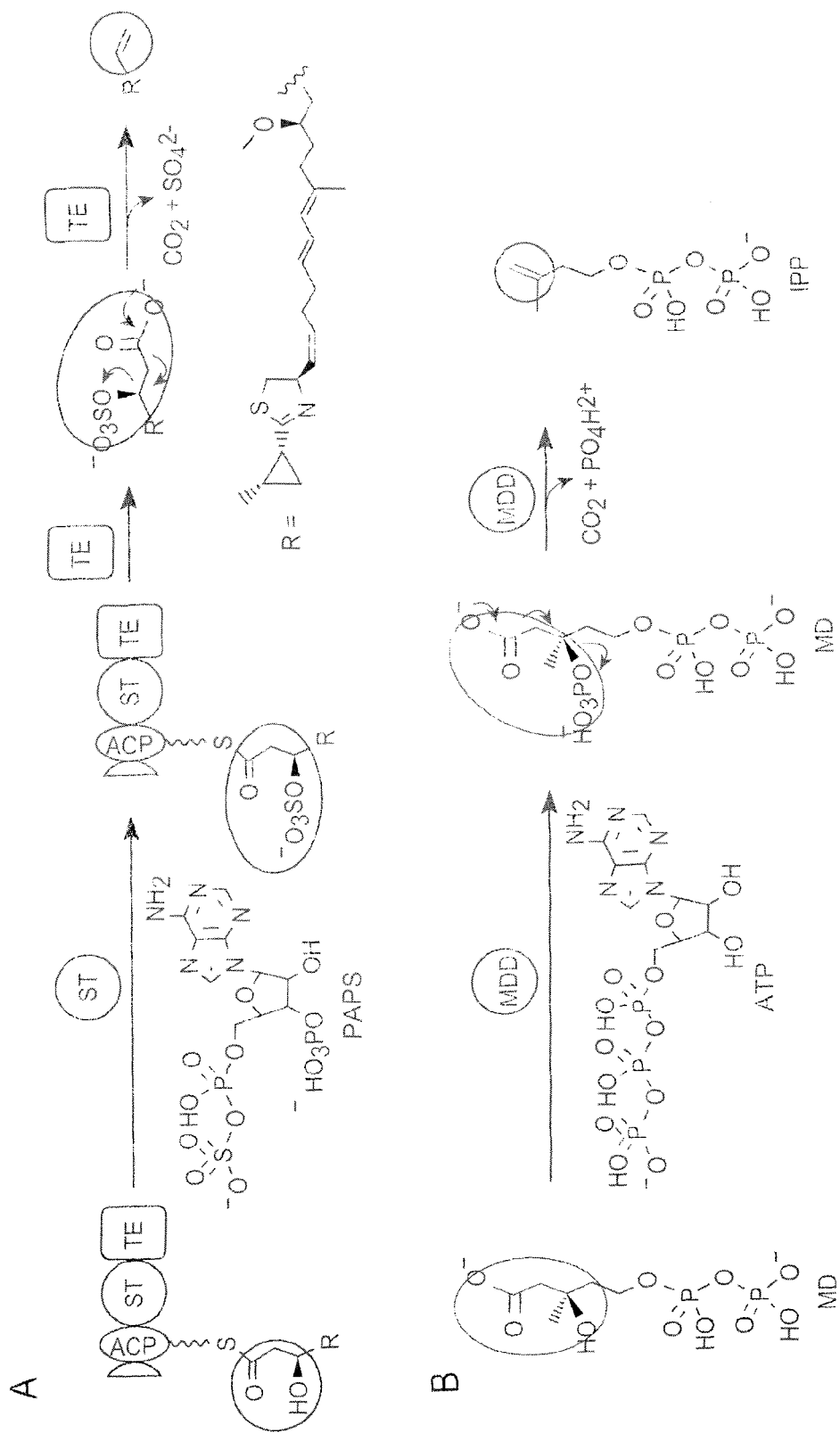
FIG. 4 shows the decarboxylative elimination mechanisms for curacin (A) and mevalonate by MDD (mevalonate-5-diphosphate decarboxylase) (B).

Disclosed herein are the biochemical reactions for the natural product biosynthesis of curacin A. A functional ST is inserted into the CurM PKS chain termination module leading to a unique series of on-assembly-line reactions. Specifically, these catalytic events transform the β-hydroxyl of the penultimate chain elongation intermediate into a β-sulfate, an excellent leaving group that is positioned chemically to facilitate decarboxylative elimination in the presence of the terminal carboxylate following TE-mediated hydrolysis of the acyl-thioester (FIG. 4A).

The significant levels of (3R)-2 (greater than 50%) as a product of the TE reaction from model substrate (3R)-1-ACP (FIG. 3A) suggests that some interactions between the native substrate and TE active site are involved in efficient coupling of the hydrolysis and decarboxylative elimination reactions. This could reflect a kinetic propensity for the sulfonated acyl-acid product of the model substrate to be released from the CurM TE active site prematurely, thus enabling isolation of (3R)-2. Indeed, given the substrate tolerance of the ST-TE module, this discovery represents a useful new metabolic engineering tool for deliberate incorporation of terminal olefins into high value natural products and other long chain hydrocarbons, including liquid fuels.

Finally, a highly similar strategy of terminal olefin formation occurs in the mevalonate pathway for isoprenoid biosynthesis (18). Specifically, mevalonate-5-diphosphate decarboxylase (MDD), along with mevalonate kinase and mevalonate-5-phosphate kinase catalyze a decarboxylative elimination reaction by first converting a β-hydroxyl group into a phosphate leaving group (FIG. 4B). In contrast, introduction of a terminal olefin as the final step in tautomycetin biosynthesis, a polyketide metabolite isolated from *Streptomyces* sp. CK4412, is more likely generated by the action of a discrete decarboxylase via yet another unique mechanism (19).

Structural Insights into Terminal Alkene Formation by the Thioesterase in the Curacin A Biosynthetic Pathway The crystal structure of CurM TE was determined to 1.7 Å. CurM TE has the expected α/β hydrolase fold but differs from other offloading TEs in lid structure and dimer interface position, which results in an open-cleft active site. Comparison with uncharacterized sequences of putative tandem ST-TE domains with presumably similar activity reveals dense conservation within the cleft. A model of the predicted acyl enzyme intermediate shows a conserved Arg205, which may confer specificity to TE for the β-sulfate, a prediction that is supported by site-directed mutagenesis studies.

Using a simplified analogue, 3-hydroxy-5-methoxytetradecanoyl-ACP, of the penultimate pathway intermediate, it has been recently demonstrated that offloading and terminal bond formation starts with the ST sulfating the β-hydroxyl group of the intermediate using the sulfate donor PAPS (28) (FIG. 1B). The TE acts upon the sulfated intermediate and produces two products: a desulfated and decarboxylated terminal double bond and a hydrolyzed carboxylic acid retaining the β-sulfate group (FIG. 1B). The TE acted very slowly on the non-sulfated substrate. This unprecedented requirement of a β-sulfate for even hydrolytic catalysis as well as the unique decarboxylation and desulfation activity points to a different catalytic strategy and active site than other FAS, PKS, or NRPS TEs.

In order to understand this novel decarboxylation and desulfation activity, CurM TE was crystallized and its three-dimensional structure was determined. Significant differences from the PKS offloading TEs were observed, especially in the lid region. Using information from the structure, and sequence alignments, a prediction of β-sulfate recognition was developed. Point mutations were made and the activity in these mutants was tested to lend support to the initial prediction, giving a mechanism for the decarboxylation and desulfation activity and specificity towards the sulfated β-hydroxyl.

Structure Determination

Since the TE is a single domain at the terminus of a larger polypeptide (CurM), the N-terminal boundary of the TE domain was ambiguous. Constructs were made with three different N-termini with the addition of the fusion protein Mocr necessary to obtain a useable yield of soluble protein. The construct starting at amino acid 1929 of CurM yielded crystals with three amino acids (SNA) added to the N-terminus (SEQ ID NO: 21). The structure was solved by SAD phasing using selenomethionyl CurM TE to 2.2 Å. A native dataset of the same crystal form was collected to 1.7 Å and was used for refinement (Table 1). The CurM TE crystal structure is deposited in the public database for three-dimensional structures of biological macromolecules (Protein Data Bank, PDB, http://www.rcsb.org) and is available with the accession code 2H7X.

TABLE 1

|  | CurM TE (SeMet) | CurM TE (native) |
|---|---|---|
| Diffraction Data |  |  |
| Space group | $P2_1$ | $P2_1$ |
| a, b, c (Å) | 74.1, 86.9, 87.1 | 74.5, 86.9, 87.6 |
| α, β, γ (°) | 90, 90.4, 90 | 90, 90.8, 90 |
| Wavelength (Å) | 0.97948 | 1.0332 |
| Resolution$^a$ (Å) | 50-2.14 (2.22-2.14) | 50-1.68 (1.74-1.68) |
| $<I/\sigma_I>$ | 16.3 (5.5) | 18.1 (2.1) |
| $R_{symm}$ | 0.113 (0.362)$^b$ | 0.059 (0.384) |
| Completeness | 99.5 (99.9) | 90.2 (49.8) |
| Average redundancy | 6.4 (6.3) | 3.4 (2.0) |
| Unique reflections | 60,509 | 127,036 |
| Total reflections | 784700 | 808,263 |
| Refinement |  |  |
| Data range (Å) | 47.46-2.14 | 34.82-1.68 |
| No. reflections | 57,064 | 108,716 |
| $R_{work}/R_{free}$$^c$ | 0.188/0.237 | 0.178/0.221 |
| RMS deviations |  |  |
| Bonds (Å) | 0.013 | 0.013 |
| Angles (°) | 1.351 | 1.331 |
| B-factors (Å$^2$) |  |  |
| Protein | 17.9 | 26.8 |
| Water | 22.5 | 39.6 |
| Ramachandran |  |  |
| allow | 99.90% | 99.60% |
| outliers | 0.10% | 0.40% |
| Protein Atoms | 8177 | 8349 |
| Water Molecules | 455 | 1119 |

Figure 8:
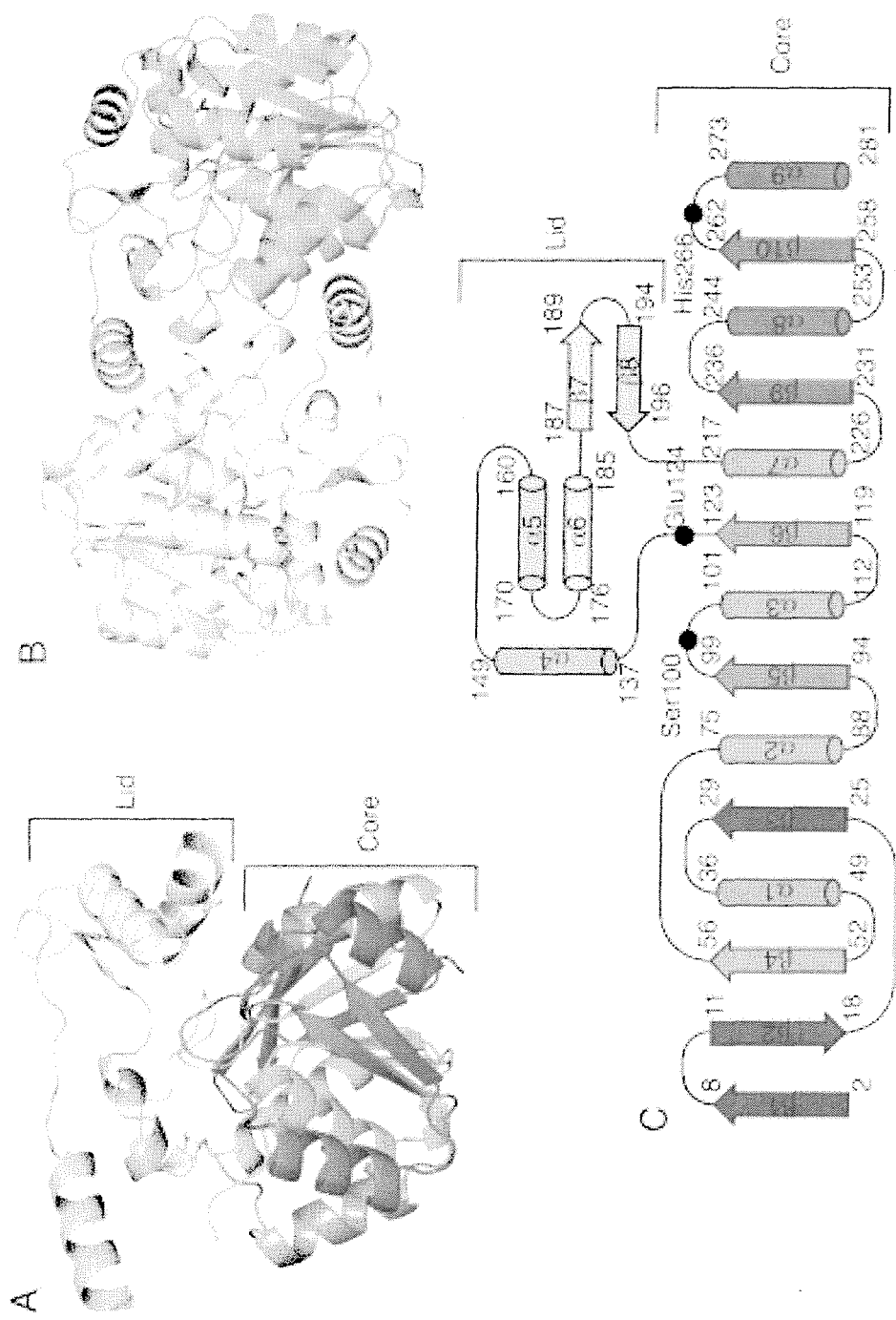
FIG. 8 shows the structure of Curacin A Thioesterase: (a) backbone trace of CurTE showing lid and core sub-domains; (b) backbone trace of CurM TE dimer viewed along the twofold; (c) topology diagram, CurM TE has an α/β hydrolase fold with conserved topology within the core and a novel lid topology.

The CurM TE structure adopts the α/β hydrolase fold with residues 1-128 and 217-283 of SEQ ID NO: 21 comprising the core domain and residues 136-204 comprising the lid (FIGS. 8A, 8C). Each of the 4 monomers in the asymmetric unit contains a disordered region in one of the two lid-to-core linking segments 129-140 and 205-216 (monomer A is disordered 131-135, B 205-216, C 130-140 and 207-215, D 134-135 and 212-215). While no single monomer provides a complete view of these loops, superposition of the monomers provides a representation of continuous connection.

Figure 13A:
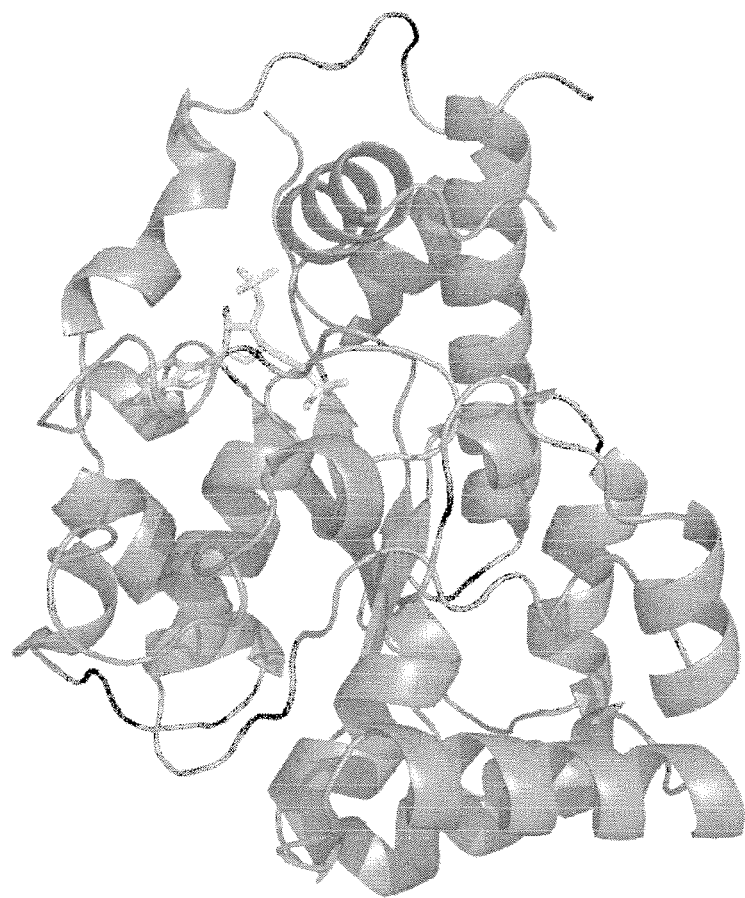
FIG. 13 shows the structure of the CurM ST domain: (a) is the polypeptide shown as a ribbon with bound PAP in stick rendering and (b) is the active site region with key amino acids indicated.
Figure 13B:
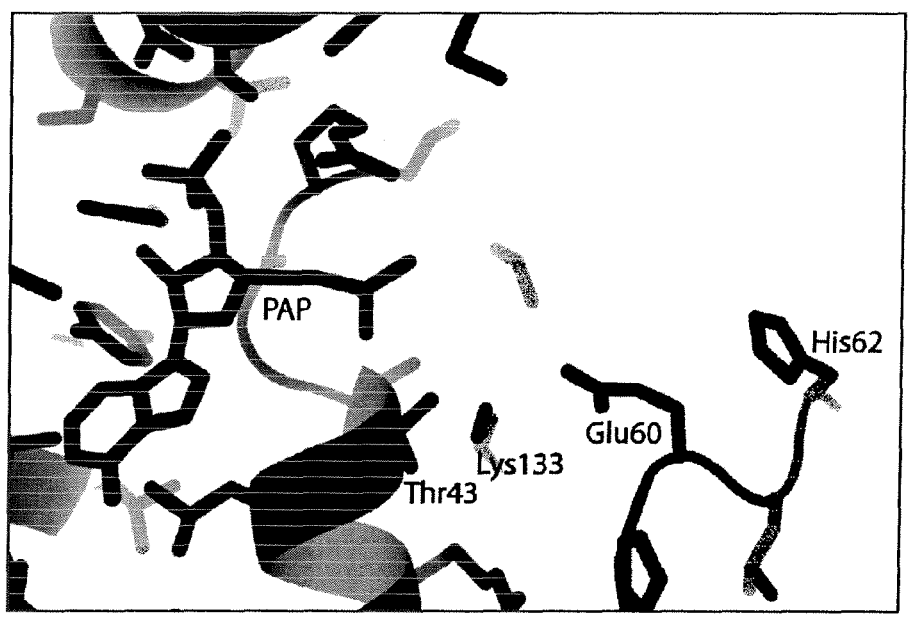

Despite its sulfotransferase (ST) catalytic activity, the CurM ST sequence could not be mapped onto any known ST structure due to low sequence identity. The CurM ST was excised from CurM as an individual domain comprising residues 1598-1917 of SEQ ID NO:1 and a three amino acid addition to the N-terminus—SNA (at positions-3, -2, and -1) (SEQ ID NO:19, renumbered as -3-320 for purposes of the description in this paragraph). Single amino acid substitutions of Gln259Ala and Lys260Ala (SEQ ID NO: 20) were engineered to reduce surface entropy and enable crystallization of the monomeric protein, and the 1.6-Å crystal structure of the recombinant ST was determined (Table 2). The core of CurM ST, representing only about 60% of the structure, has a fold similar to those of other STs, but the CurM ST has additional loops and helices in unique positions surrounding the core (FIG. 13A, 13B). The structure revealed the detailed binding of adenosine-3',5'-diphosphate (PAP), the product of the sulfate donor, 3'-phosphoadenosine 5'-phosphosulfate (PAPS). With knowledge of the PAPS/PAP binding site, the catalytic base was identified as Glu60. Other active site residues, which may be involved in substrate recognition or may assist catalysis, include His62, Lys133 and Thr43 (FIG. 13B). The CurM ST crystal structure is deposited in the public database for three-dimensional structures of biological macromolecules (Protein Data Bank, PDB, http://www.rcsb.org) and is available with the accession code 4 GBM.

TABLE 2

| Diffraction Data | |
|---|---|
| Space group | P2₁2₁2₁ |
| a, b, c (Å) | 45.8 Å, 67.3 Å, 118.0 Å |
| α, β, γ (°) | 90, 90, 90 |
| Wavelength (Å) | 1.0332 |
| Data range$^a$ (Å) | 50-1.62 (1.68-1.62) |
| Avg. I/σ$_I$ | 17.5 (4.9) |
| R$_{symm}$ | 0.074 (0.375) |
| Completeness (%) | 98.5 (89.6) |
| Average redundancy | 6.6 (5.9) |
| Unique reflections | 46,830 |
| Refinement | |
| Data range (Å) | 36.34-1.62 |
| No. reflections | 42,456 |
| R$_{work}$/R$_{free}$ | 0.185/0.205 |
| RMS deviations | |
| Bonds (Å) | 0.012 |
| Angles (°) | 1.416 |
| B-factors (Å²) | |
| Protein | 15.5 |
| Water | 24.7 |
| Ramachandran | |
| Allowed | 100.0% |
| Outliers | 0.0% |
| Protein atoms (#) | 2281 |
| Water sites (#) | 187 |
| Ligands & ions (#) | 15 |

Comparison to other Offloading TEs

Figure 9:
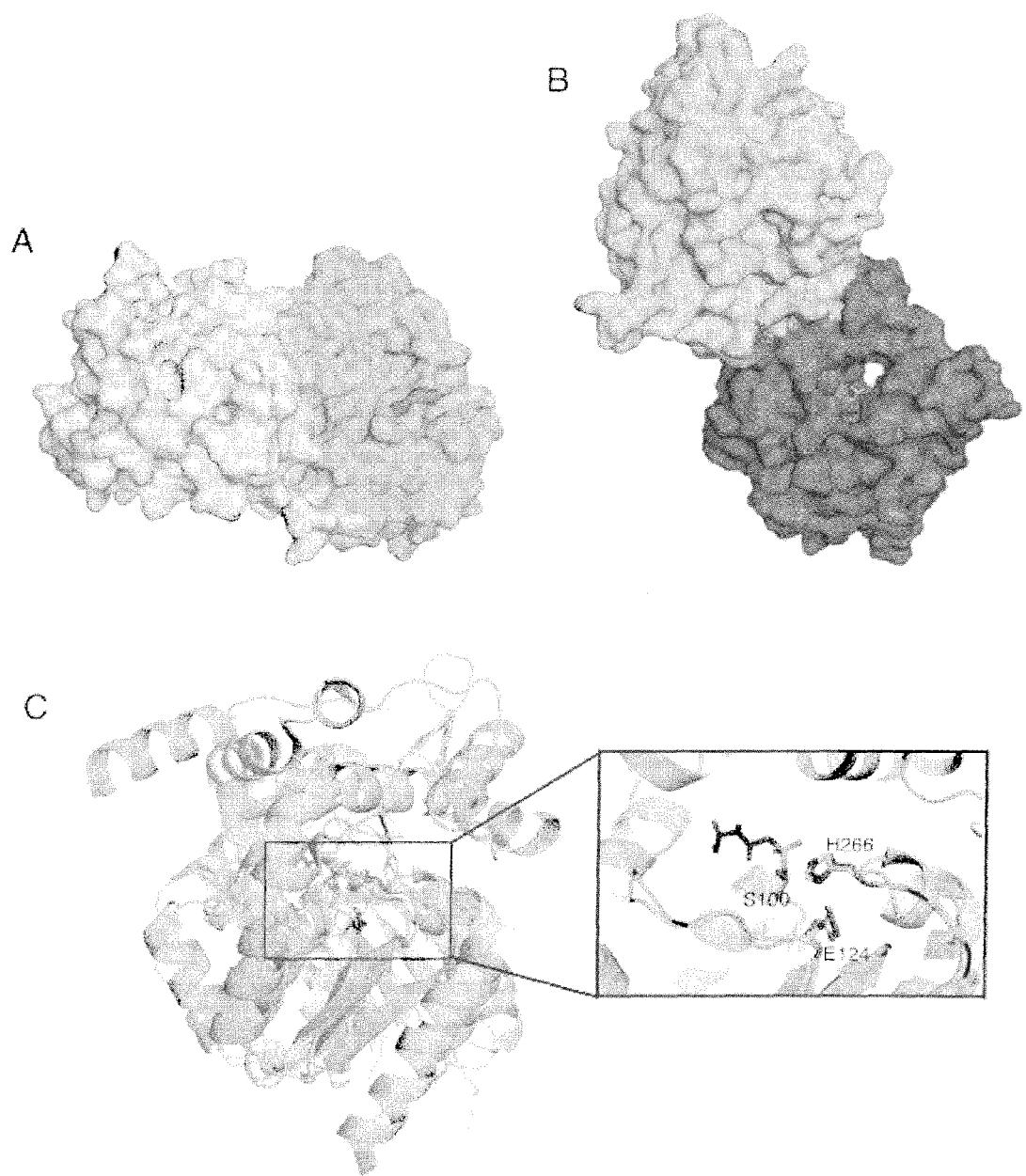
FIG. 9 shows a comparison of curacin TE to Pikromicin offloading TE (2H7X): (a) surface representation of the CurM TE dimer with the active site residues highlighted; (b) surface representation of the Pik TE dimer (affinity label in grey), where chain A of Cur and Pik are in the same orientation, showing a different dimer interface and active site access; (c) alignment of the core of CurM TE and Pik TE (RMSD=3.309 Å for 183 C-alpha atoms in the core of the structure), showing that the secondary structure is conserved in the core, but not in the lid, and the magnification shows the conservation of the active site catalytic triad position of both CurM TE and Pik TE as well as the affinity label for Pik TE.

CurM TE has similar secondary structure to other PKS offloading TEs in the core, but significant differences in secondary structure arrangement exist in the lid region (FIG. 9C). CurM TE lacks the two N-terminal dimerization helices present in the lid of PKS TEIs, which are responsible for their lid-to-lid dimerization. In the CurM TE crystal structure, this lid-to-lid dimerization is not present. However, size exclusion chromatography data indicate that CurM TE is dimeric in solution and a dimer interface different that the PKS TEI interface is observed in the crystal structure (FIGS. 8A; 9A; 9B). The CurM TE dimer interface has an average surface area of 1220 Å². It is a side-to-side dimer with a protruding helix in the lid making extensive contacts with the core of its dimeric partner. This results in a dimer that serves to hold the lid in an open conformation. When active site accessibility is compared to Pik TE, drastic differences are seen. A narrow tunnel in Pik TE contrasts an exposed cleft in CurM TE (FIGS. 9A; 9B). In both instances the specific dimer interface serves to create the environment around the active site.

Despite these differences, the position of the catalytic triad in the active site is well conserved compared to the PKS TEIs, but with the replacement of the Asp from the PKS TEIs with Glu in CurM TE (FIG. 9C). There are no other residues near the active site of CurM TE that appear to be assisting with catalysis. Using knowledge of the serine protease catalytic cycle, a catalytic scheme was predicted, which would produce the observed products (Scheme 1). In the scheme, CurM TE reacts in the same way as an offloading TE, up to the acyl-enzyme intermediate. At this point, instead of breakdown of the acyl-enzyme simply by hydrolysis, hydrolysis would be followed by an enzyme-assisted concerted decarboxylation and desulfation producing the terminal alkene (Scheme)). However, this scheme alone is not able to explain why CurM TE will perform the decarboxylation and desulfation instead of just hydrolysis or explain the selectivity of CurM TE for the sulfated β-hydroxyl. Presumably, other residues in CurM TE provide specificity and regulation. The structure was examined more closely to assess if any such residues existed.

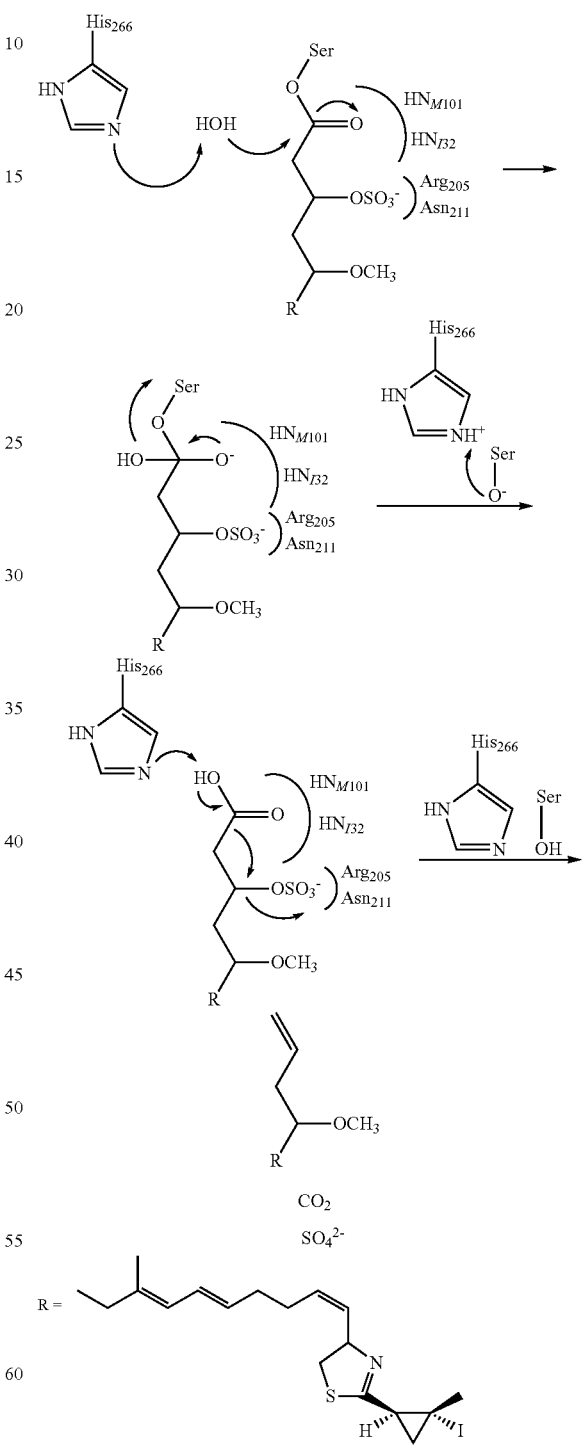

Figure 11A:
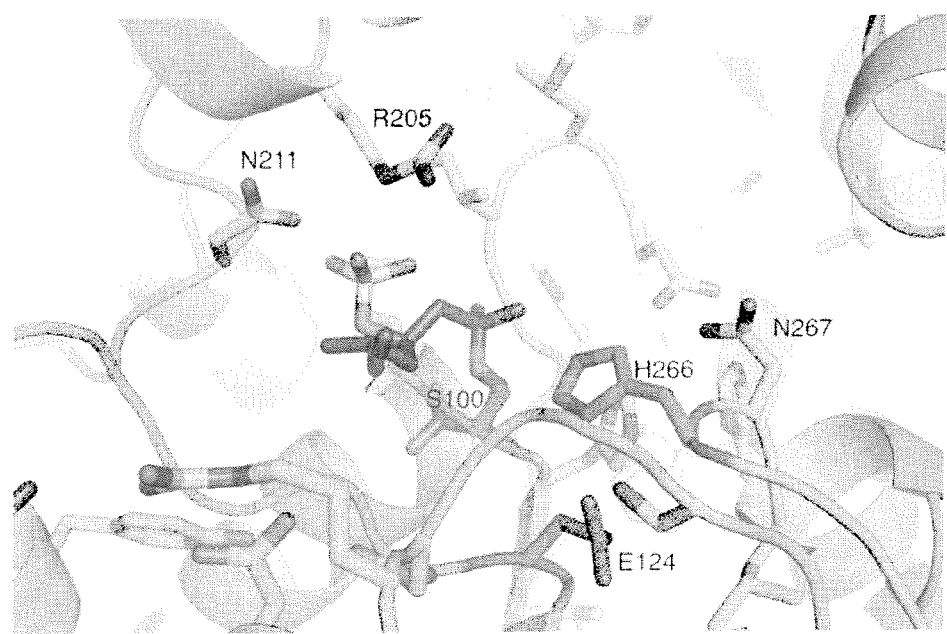
FIG. 11 shows invariant conserved residues from ACP-ST-TE with tetrahedral intermediate model: (a) modeled tetrahedral intermediate surrounded by conserved residues and catalytic triad active site residues; (b) surface model with conserved residues noted.
Figure 11B:
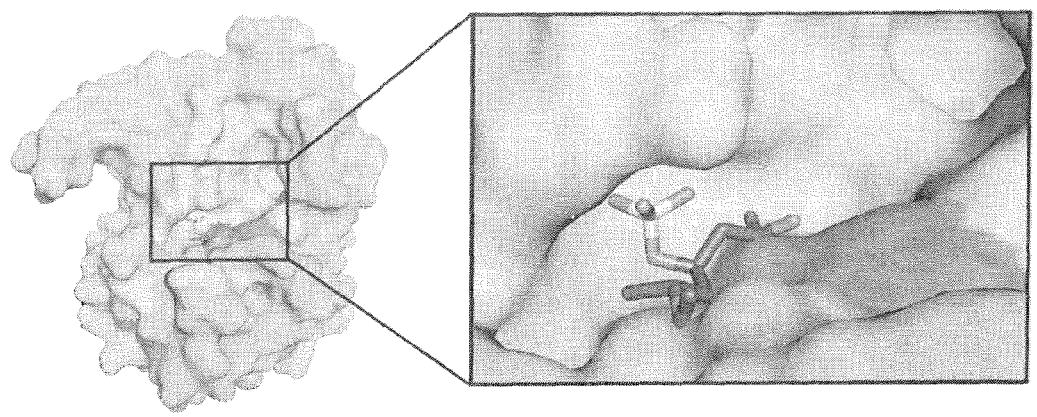

The predicted sulfated tetrahedral intermediate was modeled into the crystal structure using knowledge of nucleophile-His-acid active site catalysis and geometry and the affinity label from Pik TE (25) as a guide (FIG. 11). This shows Arg205 in a position to recognize the β-sulfate group of the modeled intermediate, suggesting it could be responsible for pushing catalysis toward decarboxylation and desulfation after hydrolysis (Scheme 1). Additionally, Arg205 can provide specificity towards sulfated substrates by helping to position the substrate for catalysis in the large open cleft, whereas the non-sulfated substrate will have no such extra guidance.

Comparison with Conserved ACP-ST-TE Sequences

When blasting the ACP-ST-TE amino acid sequence from CurM into the NCBI protein database, five other sequences were identified with 51-33% identity with CurM ACP-ST-TE (FIG. 12). These sequences are unstudied protein products from bacterial genome sequences. The high degree of conservation in all three domains led to an assumption that those gene products catalyze a similar decarboxylation and desulfation reaction. Subsequently, investigation of conserved residues within these sequences may illuminate residues important for this function.

Figure 10:
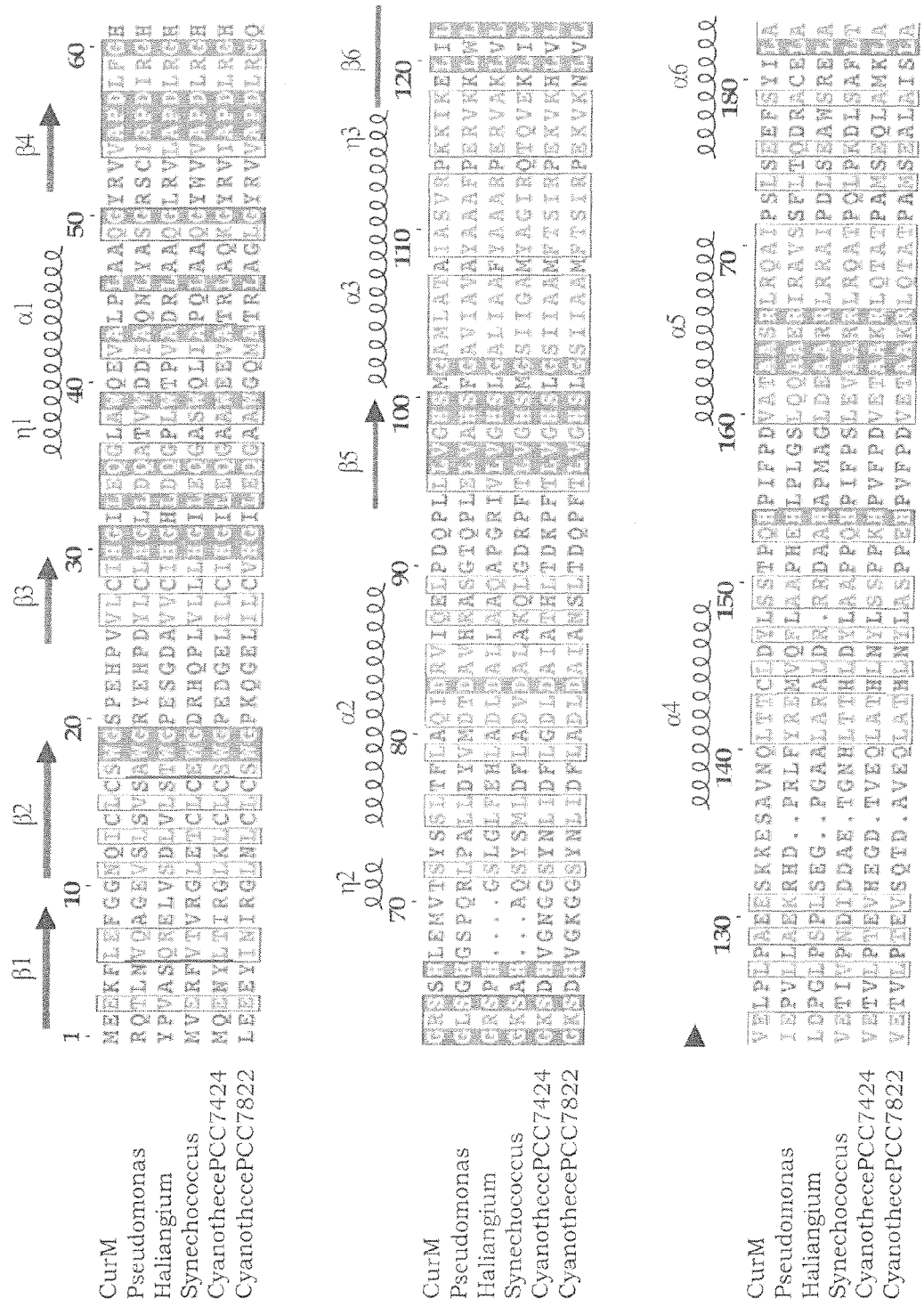
FIG. 10 shows the sequence alignment of TEs containing tandem ACP-ST-TE domains. Species used in the alignment: *Pseudomonas entomophila* L48 (SEQ ID NO: 11), *Haliangium ochraceum* DSM 14365 (SEQ ID NO: 12), *Synechococcus* PCC 7002 (SEQ ID NO: 13), *Cyanothece* PCC 7424 (SEQ NO: 14), and *Cymothece* PCC 7822 (SEQ ID NO: 15).
Figure 10:
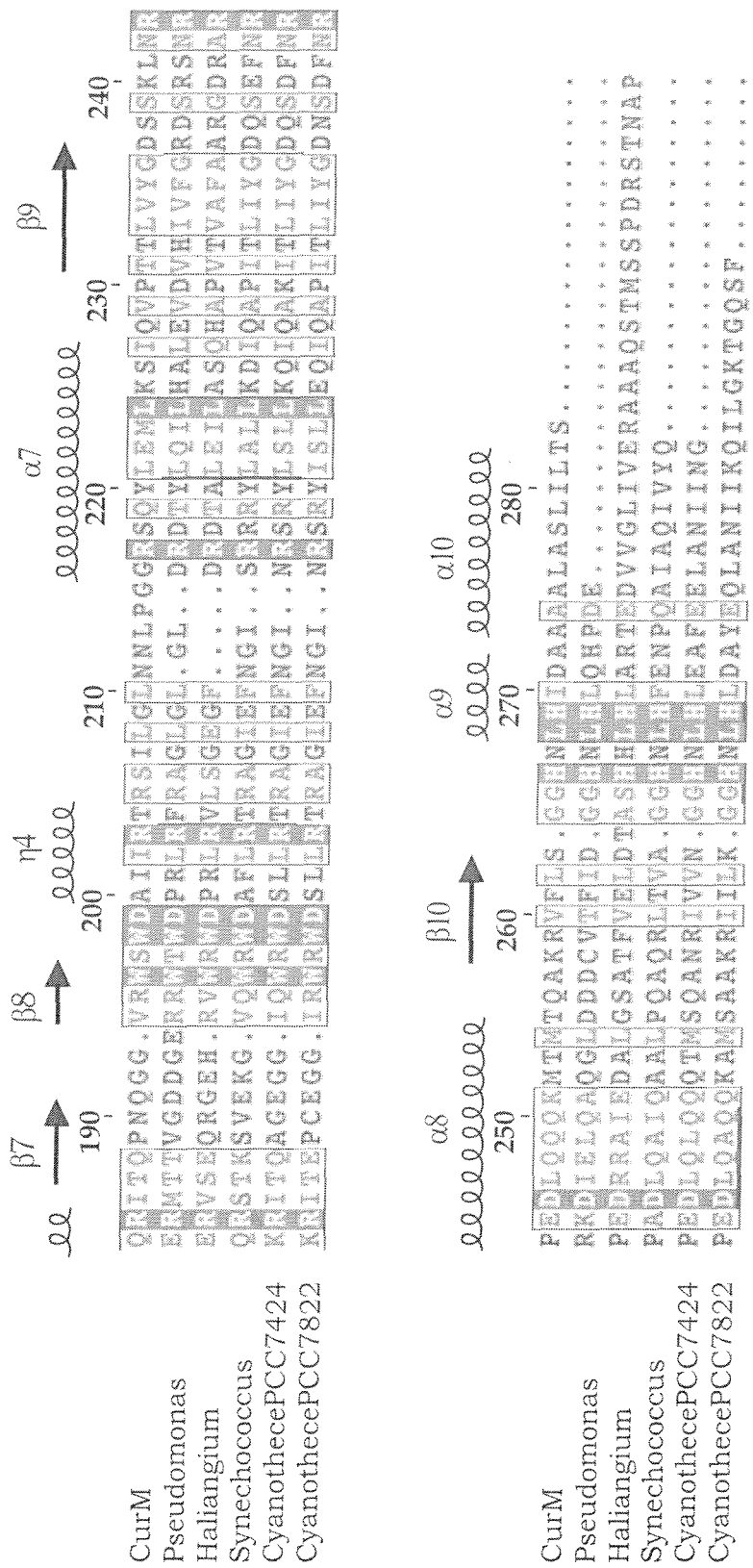

Aligning these five sequences with CurM results in 51%-32% identity (FIG. 10). When mapped onto the CurM TE structure, a dense area of conservation appears in the active site cleft (FIG. 11). The protruding helix (α4) participating in the dimer interface notably does not have invariant residues but has conservation of hydrophobic character, indicating all of the gene products should have the same dimer interface as CurM TE. The conservation in the cleft above the active site (in the opposite direction of the modeled intermediate) may serve as a docking and recognition site for ACP and Ppant arm. The conservation around the modeled intermediate could be playing a more direct role in catalysis especially R205, the residue in position to recognize the modeled sulfate. This residue is conserved in all but one sequence, *H. ochraceum*, which has two other arginines in proximity, which could serve this role. To elucidate the role of R205 and other conserved residues along the active site cleft, a series of point mutations were made.

Activity of Point Mutants

The activity of these mutants was tested using the same assay described previously (28). A one-pot reaction was used where CurM ACP was loaded with a synthesized substrate mimic (FIG. 1B) using Svp, after which CurM ST sulfates the β-hydroxyl. Lastly, CurM TE was added and the reaction is quenched after 1 minute. The liberation of holo ACP was detected by a shift on the HPLC. The ratio of holo ACP to ACP with the sulfated substrate was measured. Mutant activity was compared to the activity of wild type CurM TE and free hydrolysis without enzyme in order to obtain percent activity for the mutants (Table 3). All mutants showed reduced or no activity compared to wild type. A control mutation in the catalytic triad, H266R, showed significantly reduced (1% of WT) activity, as expected. Two conserved Asn mutants, one next to the catalytic His (N267A) and one interacting with R205 (N211A) had catalytic activity, but at a reduced rate. Notably, all R205 mutants had very reduced (1-6% of wild type) activity. When tested with the non-sulfated substrate, neither the wild type nor any of the mutants showed any detectable reaction except for the non-physiological S-β-hydroxy-substrate with the wild type CurM TE.

TABLE 3

|  | % Activity |
| --- | --- |
| WT | 100 |
| R205Q | 1.8 ± 0.3 |
| R205E | 2.3 ± 2.1 |

TABLE 3-continued

|  | % Activity |
| --- | --- |
| R205A | 6.1 ± 3.1 |
| N267A | 38.4 ± 3.1 |
| N211A | 54.7 ± 1.8 |
| H266R | 1.4 ± 0.2 |
| NO TE | 0 |

These studies result in an overall scheme of double bond formation where the β-sulfate group interacts with Arg205 to bind and react with CurM TE. It is important to note that the wild type and mutants do not react with the non-sulfated substrate, indicating CurM TE is selective for a β-sulfate group. This selection could come from the β-sulfate acting as a "handle" which R205 can use to position the substrate for catalysis. The open active site may not have sufficient specificity to allow for non-sulfated substrates to be positioned for catalysis, resulting in the observed inactivity. R205 could also plays a role in driving the concerted release of $CO_2$ and $SO_4^{-2}$ instead of the production of a carboxylic acid as would be seen in a canonical PKS TE I. The production of the sulfated carboxylic acid as well as the terminal alkene product were detected (28), indicating that in the system tested, at least part of the catalysis proceeds via the carboxylic acid. The analogous carboxylate and sulfated curacin product was never detected as being produced from *L. majuscula*, on the experimental detection of the carboxylated and sulfated product may be an off-pathway result of the experimental conditions.

CurM TE represents a new branch of the thioesterase family, optimized to work in concert with a ST to create a terminal double bond. There are already five other cases in the protein database where this type of TE appears. It may be that other organisms that have been found to produce hydrocarbons with terminal alkenes, such as *Botryococcus braunii* (44) may use this same ST-TE offloading strategy. This ability to create a terminal double bond could have applications in introducing diversity into natural products through combinatorial biosynthesis of FAS and PKS pathways, or producing hydrocarbons with terminal alkenes for possible use as a biofuel.

CurM TE has been found to have an intact catalytic triad active site, which is much more open compared to other studied PKS TEs. The unique lid arrangement and dimer interface facilitates the open-cleft surrounding the active site. High sequence conservation within the active site cleft point to its importance in CurM TE specificity and activity. Specificity is invoked through R205 guiding the β-sulfated substrate into position for catalysis in a cleft that is excessively for correct positioning of non-sulfated substrates.

Recombinant Production of Proteins

DNA encoding a polypeptide disclosed herein may be isolated and sequenced from a host cell secreting the protein using conventional procedures. Sequence determination will generally require isolation of at least a portion of the gene or cDNA of interest. Usually this requires cloning the DNA or, preferably, mRNA (i.e., cDNA) encoding the polypeptide. Cloning is carried out using standard techniques (see, e.g., Sambrook et al. (1989) *Molecular Cloning: A Laboratory Guide*, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. Nucleotide probe reactions and other nucleotide hybridization reactions are carried out at conditions enabling the identification of polynucleotides that hybridize to each other under specified conditions.

One exemplary set of conditions is as follows: stringent hybridization at 42° C. in 50% formamide, 5×SSC, 20 mM Na.PO4, pH 6.8; and washing in 1×SSC at 55° C. for 30 minutes. Formulae for calculating equivalent hybridization conditions and/or selecting other conditions to achieve a desired level of stringency are well known. It is understood in the art that conditions of equivalent stringency can be achieved through variation of temperature and buffer, or salt concentration as described Ausubel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51

In a preferred embodiment, however, the polymerase chain reaction (PCR) is used to amplify cDNAs (or portions of full-length cDNAs) encoding a polypeptide of interest. The amplified sequences can be readily cloned into any suitable vector, e.g., expression vectors, minigene vectors, or phage display vectors. It will be appreciated that the particular method of cloning used is not critical, an long as it is possible to determine the sequence of some portion of the polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The sequence of the amplified or cloned nucleic acid is then determined. Typically the sequence encoding the entire polypeptide is determined.

Sequencing can be carried out on clones isolated from any source, such as a single isolate, a cDNA library, or, when PCR is used, after subcloning the amplified sequence or by direct PCR sequencing of the amplified segment. Sequencing is carried out using standard techniques (see, e.g., Sambrook et al. (1989) *Molecular Cloning: A Laboratory Guide*, Vols 1-3, Cold Spring Harbor Press, and Sanger, F. et al. (1977) Proc. Natl. Acad. Sci. USA 74: 5463-5467, which is incorporated herein by reference).

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells, to obtain the synthesis of the polypeptide of interest in the recombinant host cells. Recombinant production of polypeptides is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome-binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells, as well as transfectants and transfected cells, include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

In an alternative embodiment, the amino acid sequence of a polypeptide of interest may be determined by direct protein sequencing. Suitable encoding nucleotide sequences can be designed according to a universal codon table.

Amino acid sequence variants of the desired polypeptide may be prepared by introducing appropriate nucleotide changes into the encoding DNA, or by peptide synthesis. Such variants include, for example, deletions from, and/or insertions into and/or substitutions of, residues within the amino acid sequences of the polypeptides. Any combination of deletion, insertion, and substitution is made to arrive at the final construct, provided that the final construct possesses the desired characteristics. The amino acid changes also may alter post-translational processes of the polypeptide, such as changing the number or position of glycosylation sites.

Nucleic acid molecules encoding amino acid sequence variants of the polypeptide are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the polypeptide.

The invention also provides isolated nucleic acid encoding polypeptides of the invention, optionally operably linked to control sequences recognized by a host cell, vectors and host cells comprising the nucleic acids, and recombinant techniques for the production of the polypeptides, which may comprise culturing the host cell so that the nucleic acid is expressed and, optionally, recovering the polypeptide from the host cell culture or culture medium.

For recombinant production of the polypeptide, the nucleic acid encoding the polypeptide is isolated and inserted into a replicable vector for further cloning (amplification of the DNA) or for expression. DNA encoding the polypeptide is readily isolated and sequenced using conventional procedures (e.g., by using oligonucleotide probes that are capable of binding specifically to genes encoding the polypeptide). Many vectors are available. The vector components generally include, but are not limited to, one or more of the following: a signal sequence, an origin of replication, one or more selective marker genes, an enhancer element, a promoter, and a transcription termination sequence.

(1) Signal sequence component: The polypeptides of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The signal sequence selected preferably is one that is recognized and processed (i.e., cleaved by a signal peptidase) by the host cell. If prokaryotic host cells do not recognize and process the native polypeptide signal sequence, the signal sequence may be substituted by a signal sequence selected, for example, from the group of the pectate lyase (e.g., pelB) alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO90/13646. In mammalian cell expression, mammalian signal sequences as well as viral secretory leaders, for example, the herpes simplex gD signal, are available.

The DNA for such precursor region is ligated in reading frame to DNA encoding the polypeptide.

(2) Origin of replication component: Each of expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μm plasmid origin is suitable for yeast, and various viral origins are useful for cloning vectors in mammalian cells. Generally, the origin of replication component is not needed for mammalian expression vectors (the SV40 origin may typically be used only because it contains the early promoter).

(3) Selective marker component: Expression and cloning vectors may contain a selective gene, also termed a selectable marker. Typical selection genes encode proteins that (a) confer resistance to antibiotics or other toxins, e.g., ampicillin, neomycin, methotrexate, tetracycline, G418, geneticin, histidinol, or mycophenolic acid (b) complement auxotrophic deficiencies, or (c) supply critical nutrients not available from complex media, e.g., the gene encoding D-alanine racemase from *Bacillus*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the polypeptide-encoding nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding the polypeptide of the invention, wild-type DHFR protein, and another selectable marker such as aminoglycoside 3'-phosphotransferase (APH) can be selected by cell growth in medium containing a selection agent for the selectable marker such as an aminoglycoside antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1. Jones, (Genetics 85:12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. Ura3-deficient yeast strains are complemented by plasmids bearing the ura3 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* Van den Berg, (Bio/Technology, 8:135 (1990)). Stable multi-copy expression vectors for secretion of mature recombinant human serum albumin by industrial strains of *Kluyveromyces* have also been disclosed (Fleer et al, Bio/Technology, 9:968-975 (1991)).

(4) Promoter component: Expression and cloning vectors usually contain a promoter that is recognized by the host organism and is operably linked to the polypeptide-encoding nucleic acid. Promoters suitable for use with prokaryotic hosts include the arabinose (e.g., araB) promoter phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Polypeptide transcription from vectors in mammalian host cells is controlled, for example, by promoters obtained from the genomes of viruses such as Abelson leukemia virus, polyoma virus, fowlpox virus, adenovirus (such as Adenovirus 2), bovine papilloma virus, avian sarcoma virus, most preferably cytomegalovirus, a retrovirus, hepatitis-B virus, Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297: 598-601 (1982) on expression of human β-interferon cDNA in mouse cells under the control of a thymidine kinase promoter from herpes simplex virus. Alternatively, the Rous sarcoma virus long terminal repeat can be used as the promoter.

(5) Enhancer element component: Transcription of a DNA encoding the polypeptide of this invention by higher eukaryotes is often increased by inserting an enhancer sequence into the vector. Many enhancer sequences are known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(6) Transcription termination component: Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein. Another is the mouse immunoglobulin light chain transcription terminator.

(7) Selection and transformation of host cells: Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhinwrium, Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. Inctrxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of polypeptides are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for polypeptide production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of polypeptides.

(8) Culturing the host cells: The host cells used to produce the polypeptides of this invention may be cultured in media suitable for promoting growth in the cell expression system utilized. Yeast and baceterial cells may be expressed using media well-known in the art, such as defined media, undefined media or dropout media (e.g., lacking certain amino acids or sugars for selection of cells) as appropriate for the expression system used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian host cells. In addition, any of the media described in Ham et al., (Meth. Enz. 58: 44, 1979), Barnes et al., Anal. Biochem. 102: 255 (1980), U.S. Pat. Nos. 4,767,704; 4,657, 866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of polypeptides: When using recombinant techniques, the polypeptide can be produced intracellularly, in the periplasmic space, or directly secreted into the medium, including from microbial cultures. If the polypeptide is produced intracellularly, as a first step, the particulate debris, either host cells or lysed fragments, is removed, for example, by centrifugation or ultrafiltration. Better et al. (Science 240: 1041-43, 1988; ICSU Short Reports 10:105 (1990); and Proc. Natl. Acad. Sci. USA 90:457-461 (1993) describe a procedure for isolating antibodies which are secreted to the periplasmic space of *E. coli*. [See also, (Carter et al., Bio/Technology 10:163-167 (1992)].

The polypeptide composition prepared from microbial or mammalian cells can be purified using, for example, hydroxylapatite chromatography cation or anion exchange chromatography, and affinity chromatography, with affinity chromatography being a preferred purification technique. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE® chromatography on an anion or cation exchange resin (such as a polyaspartic acid column), chromatofocusing, SDS-PAGE, ammonium sulfate precipitation and immunoaffinity are also available depending on the polypeptide to be recovered.

Antibodies

In one embodiment, the invention contemplates an antibody that is specifically reactive with the polypeptides described herein. As used herein "antibody" refers to an antibody or fragment thereof, or a polypeptide comprising an antigen binding domain of an antibody. Exemplary antibodies or antibody fragments include polyclonal antibodies, monoclonal antibodies, chimeric antibodies, humanized antibodies, human antibodies, multispecific antibodies, Fab, Fab', F(ab')2, Fv, domain antibody (dAb), complementary determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences.

As used herein, an antibody that "specifically binds" is "antigen specific," is "specific for" antigen target or is "immunoreactive" with an antigen refers to an antibody that binds an antigen with greater affinity than other antigens of similar sequence. In one aspect, the antibodies contemplated, or fragments, variants, or derivatives thereof, will bind with a greater affinity to target antigen as compared to its binding affinity to similar antigens derived form other sources, e.g., other species, but antibodies that recognize and bind orthologs of the target are within the scope of the invention.

Immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. An antibody contemplated herein, if it comprises a constant domain, may be of any of these subclasses or isotypes.

Various procedures known in the art may be used for the production of polyclonal or monoclonal antibodies to the polypeptide of the invention. For the production of antibodies, various host animals (including but not limited to rabbits, mice, rats, hamsters, and the like) are immunized by injection with a polypeptide described herein. Various adjuvants may be used to increase the immunological response, depending on the host species, including but not limited to Freund's (complete and incomplete) adjuvant, mineral gels such as aluminum hydroxide, surface active substances such as lysolecithin, pluronic polyols, polyanions, oil emulsions, keyhole limpet hemocyanins, dinitrophenol, and potentially useful human adjuvants such as BCG (Bacille Calmette-Guerin) and *Corynebacterium parvum*.

Monoclonal antibodies may be made by techniques well-known in the art, including, but not limited to the hybridoma technique originally described by Köhler et al., *Nature,* 256: 495-497 (1975), and the more recent human B-cell hybridoma technique [Kosbor et al., *Immunology Today,* 4:72 (1983)] and the EBV-hybridoma technique [Cole et al., *Monoclonal Antibodies and Cancer Therapy*, Alan R Liss, Inc., pp. 77-96 (1985),] or by recombinant DNA methods (see, e.g., U.S. Pat. No. 4,816,567) (all specifically incorporated herein by reference). The monoclonal antibodies may also be isolated from phage antibody libraries using the techniques described in, for example, Clackson et al., (*Nature* 352:624-628, 1991) and Marks et al., (*J. Mol. Biol.* 222:581-597, 1991).

In addition to the production of monoclonal antibodies, techniques developed for the production of "chimeric antibodies," e.g., the splicing of an antibody gene from one species to antibody genes of another species to obtain a molecule with appropriate antigen specificity and biological activity, can be used [Morrison et al., *Proc. Natl. Acad. Sci.* 81:6851-6855 (1984); Neuberger et al., *Nature* 312:604-608 (1984); Takeda et al., *Nature* 314:452-454 (1985)]. Alternatively, techniques described for the production of single-chain antibodies (U.S. Pat. No. 4,946,778) can be adapted to produce antibodies.

Antibody fragments that contain the idiotype of the molecule may be generated by known techniques. For example, such fragments include, but are not limited to, the F(ab')$_2$ fragment which may be produced by pepsin digestion; the Fab' fragments which may be generated by reducing the disulfide bridges of the F(ab')$_2$ fragment, and the two Fab fragments which may be generated by treating the antibody molecule with papain and a reducing agent. Additionally, using techniques known in the art to isolate CDRs, compositions comprising CDRs are generated. CDRs are characterized by six polypeptide loops, three loops for each of the heavy or light chain variable regions. The amino acid position in a CDR is defined by Kabat et al., "Sequences of Proteins of Immunological Interest," U.S. Department of Health and Human Services (1983), which is incorporated herein by reference.

Screening assays to determine binding specificity of an antibody for use in the methods of the invention are well known and routinely practiced in the art. For a comprehensive discussion of such assays, see Harlow et al. (Eds), *Antibodies A Laboratory Manual*; Cold Spring Harbor Laboratory; Cold Spring Harbor, N.Y. (1988), Chapter 6. Antibodies for use in the invention can be produced using any method known in the art.

EXAMPLES

The following examples are provided to illustrate the invention, but are not intended to limit the scope thereof.
Chemical Synthesis

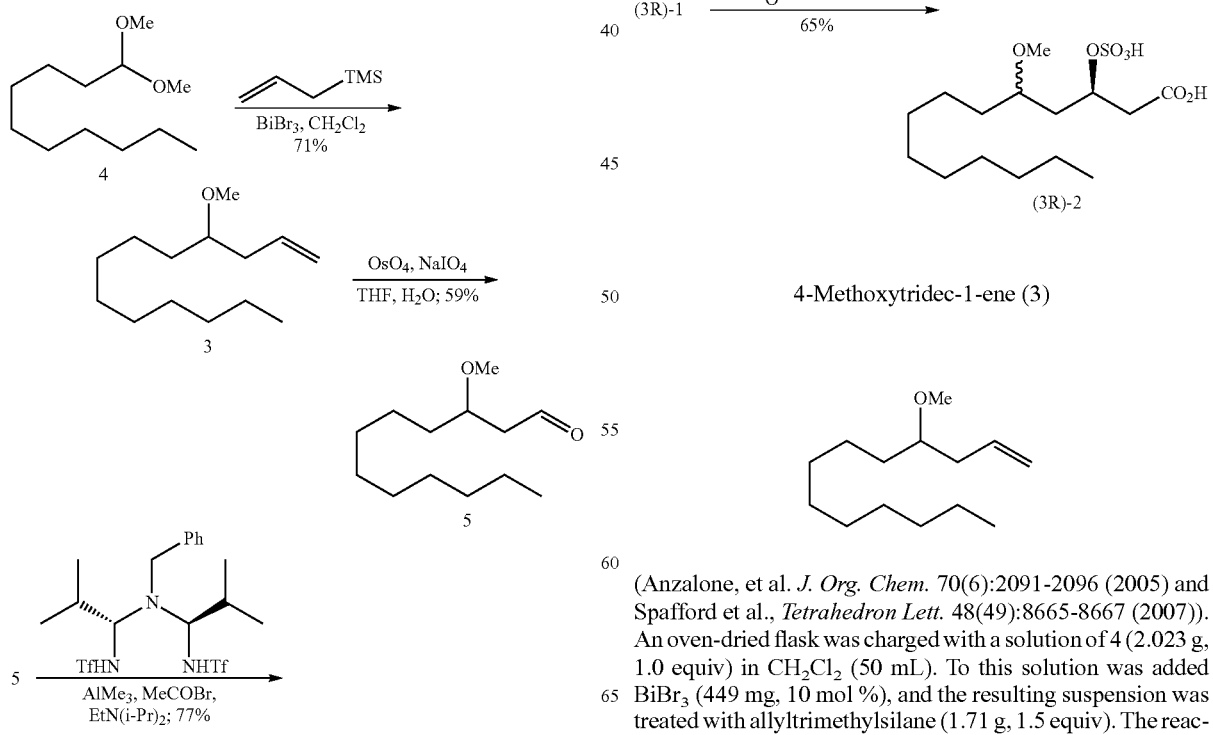

4-Methoxytridec-1-ene (3)

(Anzalone, et al. *J. Org. Chem.* 70(6):2091-2096 (2005) and Spafford et al., *Tetrahedron Lett.* 48(49):8665-8667 (2007)). An oven-dried flask was charged with a solution of 4 (2.023 g, 1.0 equiv) in CH$_2$Cl$_2$ (50 mL). To this solution was added BiBr$_3$ (449 mg, 10 mol %), and the resulting suspension was treated with allyltrimethylsilane (1.71 g, 1.5 equiv). The reaction mixture was stirred for 4 h at rt, and quenched by pouring into a separatory funnel containing 1 M HCl (50 mL). The organic layer was washed with saturated NaHCO$_3$ (50 mL) and brine (50 mL), dried (Na$_2$SO$_4$, and the solvent was removed in vacuo. The crude residue was purified by chromatography on SiO$_2$ (2% EtOAc/hexanes) to afforded 2(1.508 g, 71%) as a colorless oil: $^1$H NMR (CDCl$_3$) δ 5.9-5.75 (m, 1H), 5.1-5.0 (m, 2H). 3.35; (s, 3H), 3.21 (p, 1H, J=5.7 Hz), 2.29-2.25 (m, 2H), 1.50-1.40 (m, 2H), 1.40-1.25 (m, 14H), 0.90 (t, 3H, J=6.9 Hz); $^{13}$C NMR (CDCl$_3$) δ 134.9, 116.6, 80.4, 56.4, 37.7, 33.3, 31.8, 29.7, 29.5, 29.3, 25.2, 22.6, 14.0.

3-Methoxydodecanal (5)

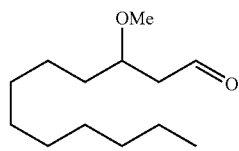

A solution of 3 (424.7 mg. 1.0 equiv) in THF (8 mL) was treated with NaIO$_4$ (2.14 g, 5.0 equiv) and water (4 mL). The reaction mixture was stirred at rt for ca. 2 min, treated with OsO$_4$ (0.67 mL of a 0.3 M solution in toluene) and stirred at rt for 3 h. The mixture was poured into a separatory funnel containing H$_2$O (10 mL) and EtOAc (10 mL). The organic layer was washed with brine (20 mL), dried (Na$_2$SO$_4$), and the solvent was removed in vacuo to afford a pale yellow oil. Purification by chromatography on SiO$_2$ (2% EtOAc/hexanes to 4% EtOAc/hexanes) afforded 5 (253 mg, 59%) as a pale yellow oil that was used without further purification: $^1$H NMR (CDCl$_3$) δ 9.8 (t, 1H, J=1 Hz), 3.75-3.65 (m, 1H), 3.34 (s, 3H), 2.65-2.45 (m, 2H), 1.70-1.40 (m, 2H), 1.40-1.20 (m, 14H), 0.85 (t, 3H, J=6.8 Hz).

(4R)-4-((2RS)-2-Methoxyundecyl)oxetan-2-one (6)

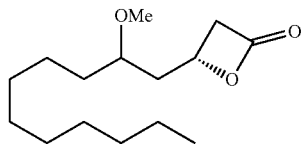 [SMILES: CCCCCCCCCC(C[C@@H]1CC(=O)O1)OC]

A solution of N,N'-(1R,1'R)-1,1'-(benzylazanediyl)bis(2-methylpropane-1,1-diyl)bis(1,1,1-trifluoromethanesulfonamide) (81.2 mg, 0.15 mmol, 30 mol %) in CH$_2$Cl$_2$ (1 mL) was treated at rt under N$_2$ slowly with a solution of AlMe$_3$ (10.8 mg, 0.15 mmol) in CH$_2$Cl$_2$ (0.5 mL). The mixture was stirred at room temperature (rt) for 2 h, cooled to −45° C. and treated sequentially with diisopropylethylamine (11 mg, 1.7 equiv), acetyl bromide (117 mg, 1.9 equiv) and 5 (107 mg, 0.500 mmol, 1.0 equiv). The resulting pale yellow solution was stirred for 14 h at −45° C., warmed to rt, and poured into a separatory funnel containing 0.1 N HCl (10) mL). The organic layer was washed with saturated NaHCO$_3$, brine, and dried (Na$_2$SO$_4$). The solvent was removed in vacuo and the yellow oily product was purified by chromatography on SiO$_2$ (4% EtOAc/hexanes to 6% EtOAc/hexanes) to give 6 (99.1 mg, 77%) as a colorless oil: 1H NMR (CDCl$_3$) δ 4.8-4.65 (m, 1H), 3.60-3.50 (m, 1H), 3.3-3.2 (m, 1H), 3.35, 3.32 (2s, 3H), 3.22-3.08 (m, 1H), 2.18-1.82 (m, 2H) 1.65-1.35 (m, 2H), 1.35-1.20 (m, 14H), 0.90-0.80 (m, 3H).

(3R,5RS)-3-Hydroxy-5-methoxytetradecanoic acid ((3R)-1)

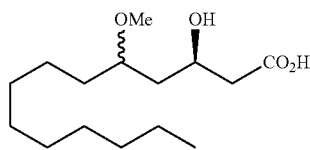 [SMILES: CCCCCCCCCC(C[C@@H](O)CC(=O)O)OC]

(ref. Gu, et al. *Nature* 459, 731-735 (2009)). To a solution of 6 (92.0 mg, 0.359 mmol, 1.0 equiv) in THF (1.5 mL) was added a solution of NaOH (15.7 mg, 0.394 mmol, 1.1 equiv) in water (1.5 mL). The reaction mixture was stirred at rt for 1 h. During this time, its appearance changed from turbid to clear (t=about 0.5 h). The solution was quenched by addition of 1 M HCl (1 mL) and extracted with ether (2×5 mL). The combined organic layers were washed with water (5 mL) and brine (5 mL), dried (Na$_2$SO$_4$) and concentrated in vacuo to afford a pale yellow oil. Purification of the crude product by chromatography on SiO$_2$ (1:1 EtOAc/hexanes containing 0.5% AcOH) provided (3R)-1 (94.4 mg, 96%) as a colorless oil: ATR/IR 2920, 2851, 1709, 1413, 1187, 1079, 736 cm$^{-1}$; $^1$H NMR (CDCl$_3$) δ 4.35-4.20 (m, 1H), 3.55-3.45 (m, 1H), 3.38, 3.37 (2s, 3H), 2.56-2.50 (m, 2H), 1.80-1.35 (m, 3H), 1.35-1.25 (m, 14H), 0.90 (t, 3H, J=6.9 Hz); $^{13}$C NMR (CDCl$_3$) δ 176.4, 175.7, 68.1, 65.4, 56.7, 56.0, 41.6, 41.5, 39.7, 39.1, 32.9, 32.8, 31.9, 29.8, 29.6, 29.5, 29.3, 25.2, 24.5, 22.7, 14.1.

(4S)-4-((2RS)-2-Methoxyundecyl)oxetan-2-one (7)

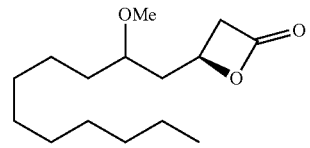 [SMILES: CCCCCCCCCC(C[C@H]1CC(=O)O1)OC]

(ref. Nelson, et al., *J. Am. Chem. Soc.* 121(41):9742-9743 (1999)). A solution of N,N'-(1S,1'S)-1,1'-(benzylazanediyl) bis(2-methylpropane-1,1-diyl)bis(1,1,1-trifluoromethanesulfonamide) (81.2 mg, 0.15 mmol, 30 mol %) in CH$_2$Cl$_2$ (1 mL) was treated at rt under N$_2$ slowly with a solution of AlMe$_3$ (10.8 mg, 0.15 mmol) in CH$_2$Cl$_2$ (0.5 mL). The mixture was stirred at rt for 2 h, cooled to −45° C. and treated sequentially with diisopropylethylamine (11 mg, 1.7 equiv), acetyl bromide (117 mg, 1.9 equiv) and 3 (107 mg, 0.500 mmol, 1.0 equiv). The resulting pale yellow solution was stirred for 14 h at −45° C., warmed to rt, and poured into a separatory funnel containing 0.1 N HCl (10 mL). The organic layer was washed with saturated NaHCO$_3$, brine, and dried (Na$_2$SO$_4$). The solvent was removed in vacuo and the yellow oily product was purified by chromatography on SiO$_2$ (4% EtOAc/hexanes to 6% EtOAc/hexanes) to give 7 (87 mg, 81%) as a colorless oil that was saponified without further purification.

(3S,5RS)-3-Hydroxy-5-methoxytetradecanoic acid ((3S)-1)

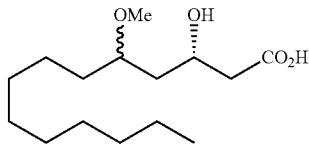 [SMILES: CCCCCCCCCC(C[C@H](O)CC(=O)O)OC]

To a solution of 7 (187 mg, 0.729 mmol, 1.0 equiv) in THF (2.5 mL) was added a solution of NaOH (32.) mg, 0.802 mmol, 1.1 equiv) in water (1 L). The reaction mixture was stirred at rt for 2 h, transferred to a separatory funnel, diluted with water (5 mL) and extracted with ether. The aqueous layer was acidified with 2 N HCl (3 mL) and extracted with ether (2×15 mL). The combined organic layers were dried ($Na_2SO_4$) and concentrated in vacuo to afford (3S)-1 (187 mg, 93%) as a colorless oil that was used without further purification: ATR/IR 2920, 2851, 1709, 1412, 1189, 1079, 738 $cm^{-1}$; $^1H$ NMR ($CDCl_3$) δ 4.85-4.7 (m, 1H), 3.55-3.45 (m, 1H), 3.39, 3.38 (2s, 3H), 2.56-2.52 (m, 2H), 1.80-1.35 (m, 3H), 1.35-1.25 (m, 14H), 0.90 (t, 3H, J=6.9 Hz); $^{13}C$ NMR ($CDCl_3$) δ 176.5, 175.8, 81.5, 78.7, 68.0, 65.3, 56.7, 55.9, 41.5, 39.6, 39.0, 32.8, 32.6, 31.8, 29.7, 29.5, 29.2, 25.1, 24.4, 22.6, 14.1; MS (EI) m/z 274 ($M^+$, 0.5), 256 (0.5), 171, 25, 129 (100), 97 (15).

(3R,5RS)-3-Sulfonatooxy-5-methoxytetradecanoic acid ((3R)-2)

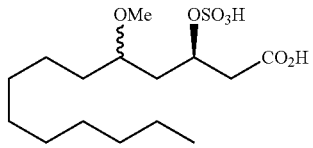

(ref. Strehmel, et al., *Tetrahedron Letters* 49(4):586-588 (2008)). To a solution of 5 (5.5 mg, 0.02 mmol, 1.0 equiv) in methylene chloride (1 mL) was added slowly a solution of trimethylsilyl chlorosulfonate (3.8 mg, 0.02 mmol, 1.0 equiv) in methylene chloride (1 mL) under $N_2$. The reaction mixture was stirred at 0° C. for 6 h before warmed it up to rt. The mixture was concentrated in vacuo to yield a pale yellow oil containing (3R)-2 (about 65% yield), which was applied as an authentic standard for the intermediates of ST and TE reactions. Due to instability of (3R)-2, the mixture was not purified before subjected to LC-MS and MS/MS analysis. MS (ESI) calculated for [M-H]⁻ 353.17, found 353.09. MS/MS fragmentation of 353.09, found 273.17 and 309.09, corresponding to the losses of $SO_3$ and $CO_2$ respectively.

(3R)-1-CoA/(3S)-1-CoA.

The CoA thioesterification of (3R)-1 and (3S)-1, as we as product purification, was performed in the similar way as previously described Gu, et al., *J. Am. Chem. Soc.* 128(28): 9014-9015 (2006) and Geders, et al., *J. Biol. Chem.*, 282: 35954-35963(2007)). For both (3R)-1-CoA and (3S)-1-CoA, MS (ESI) calculated for [M-H]⁻ 1022.32, found 1022.28.

Bioinformatic Analysis for Prediction of CurM KR Stereospecificity

Based on alignments of KR domains, the CurL and CurM KR domains contain the LDD motif, indicating that they catalyze formation B-type hydroxyl groups. Chirality of the carbon atom bearing the methoxyl group in curacin A confirms the prediction for CurL KR stereospecificity.

Bacterial Strains, Media and Culture Conditions

*Escherichia coli* DH5α MCR (Invitrogen) was used for DNA propagation. *E. coli* BL21 (DE3) transformed with the pET24b and pET28b constructs were used for protein overexpression in Luria-Bertani medium. Ampicillin (100 μg/mL), carbenicillin (100 μg/mL), kanamycin (50 μg/mL), and apramycin (50 μg/mL) were used for the corresponding plasmid construct resistance marker selection in *E. coli* cultures.

DNA Sequencing of curM and 3' Flanking Region

To identify cosmids containing the 3' end of cur gene cluster, the previous cosmid genomic library of *L. majuscula* strain L19 (Chang et al, *Gene* 296, 235-247 (2002)) was screened by PCR using an oligonucleotide primer pair to amplify the curM ST gene: (F) 5'-GGA TGC GGA TGC AAA AAC TTG-3' (SEQ ID NO: 6) and (R) 5'-CGG ATG CAA AAA CTT GTC GGG-3' (SEQ ID NO: 7). Two cosmids, pLM14 and pLM19, in addition to pLM17, were identified to contain curM ST. These three cosmids were also examined by comparing their restriction enzyme digestion patterns. The pLM14 was chosen to be sequenced by primer walking method for the 3' end of curM and the flanking region. The new sequence was compared with the genome sequencing data (unpublished), and is SEQ ID NO: 1 (amino acid sequence) and SEQ ID NO: 2 (DNA sequence).

Plasmid Construction

CurM ACP, ST and TE genes were amplified from the pLM14. The CurM ACP and TE genes were inserted into pET24b plasmid at the NdeI and NotI restriction sites. The CurM ST gene was inserted into pET28b plasmid with NdeI and BamHI restriction sites. All the constructs were verified by DNA sequencing. The primers for the plasmid construction are: ACP (F): 5'-<u>CATATG</u> ACA GAC GAA CGC ATT TTA G-3'(SEQ ID NO: 8), ACP (R): 5'-<u>GCGGCCGCT</u> AAG CTT GTT GGA GAT GG-3'(SEQ ID NO: 9), ST (F): 5'-<u>CATATG</u> ATC TTT GCA ACC AAA AGT TCA-3'(SEQ ID NO: 10), ST (R): 5'-<u>GGATCC</u> TTA TTG AGG CTG TTG ATT TGT CG-3'(SEQ ID NO: 16), TE (F): 5'-<u>CATATG</u> CAA GTC TCT ACA ACT CCC T-3'(SEQ ID NO: 17), and TE (R): 5'-<u>GCGGCCGCG</u> GAT GTT AAG ATA AGT GAT GC-3' (SEQ ID NO: 18).

Protein Overexpression

*E. coli* BL21 (DE3) was transformed with pET24b::ACP or pET24b::TE plasmid to overexpress C-terminal Histagged proteins, and by pET28b::ST plasmid to overexpress N-terminal His-tagged protein. ACP was overexpressed in the apo form. Cells were grown at 30° C. to an OD (590 nm)=0.5-0.6, and then cooled to 15° C. prior to the addition of 1 mM isopropyl-β-D-galactopyranoside. The cultures were grown at 15° C. for another 18-20 h before harvesting.

Protein Purification

Protein purifications were performed at 4° C. *E. coli* cells were harvested by centrifugation (5,000 g, 15 min, 4° C.), resuspended in ice cold lysis buffer A (50 mM PBS buffer, pH 8.0, 300 mM NaCl, 10 mM imidazole, 20% glycerol) and disrupted by sonication on ice. The cell debris was removed by centrifugation at 15,000 g for 50 min. The supernatant was gently removed and loaded onto the 5 ml HisTrap column (GE Healthcare pre-equilibrated with lysis buffer A. The resin was washed successively with ~10 column volumes of the washing buffer B (50 mM PBS buffer, pH 8.0, 300 mM NaCl, 20 mM imidazole, 10% glycerol) to remove nonspecifically bound contaminants. Bound proteins were eluted with imidazole by a linear gradient of the elution buffer C (50 mM PBS buffer, pH 8.0, 300 mM NaCl, 250 mM imidazole, 20% glycerol). The eluate fractions were examined by SDS-PAGE for purity, pooled and concentrated using Amicon Ultra-15 (10 kDa or 5 kDa) centrifugal devices (Millipore). The concentrated eluate was loaded onto HiLoad 26/60 Superdex 200 column (GE Healthcare) equilibrated with the storage buffer D (50 mM PBS buffer, pH 7.5, 200 mM NaCl, 20% glycerol). The fractions were pooled, concentrated, flash-frozen in 50-100 µl aliquots in liquid $N_2$, and stored at −80° C. for future use. The purity of the proteins was analyzed by SDS-PAGE and the protein concentrations were determined using the Bradford assay (Bio-Rad).

Preparation of the ACP-Linked Substrates

The (3R)-1-ACP and (3S)-1-ACP substrates were prepared by loading the (3R)-1-CoA and (3S)-1-CoA onto the (apo) CurM ACP by using *S. verticillus* Svp. Briefly, 500 µM acyl-CoA and 50 µM (apo) ACP were incubated with 10 µM Svp, and 10 mM $MgCl_2$ in 50 mM Tris-HCl buffer, pH 8.1, at room temperature for about 2 h. Reaction mixtures were desalted by PD10 column equilibrated with buffer D. The desalted acyl-ACPs were concentrated by using Amicon Ultra-4 (5 kDa, Millipore), flash-frozen in 10-50 µl aliquots in liquid $N_2$, and stored at −80° C. The ACP samples were analyzed by reverse-phase HPLC using a Jupiter C4 column (250×2.0 mm, 5 µm, 300 Å, Phenomenex), and a linear elution gradient from 5% to 100% of $CH_3CN$ (0.1% $CF_3CO_2H$)/$H_2O$ (0.1% $CF_3CO_2H$).

Kinetic Studies of TE Hydrolysis Using CoA-Linked Substrates

HPLC-based analyses of the TE hydrolysis were performed using XBridge C18 column (4.6×250 mm, 5 µm, Waters) on the Gold HPLC system equipped with an autosampler and controlled by 32 Karat software (Beckman Coulter). Samples were eluted with a linear gradient from 10% to 90% of $MeOH/H_2O$ (10 mM $CH_3CO_2NH_4$). For steady state kinetic studies. TE hydrolysis was examined in 40 µl 50 mM Tris-HCl buffer (pH 7.0) with 100 µM, 200 µM, 500 µM, 1000 µM and 2000 µM (3R)-1-CoA or (3S)-1-CoA. 1.25 µM TE was incubated with the CoA substrates at room temperature for 10 min before quenched by 40 µl 1M $CH_3CO_2H$. The reaction mixtures were then added with isovaleryl-CoA as an internal standard before filtered by Microcon YM-10 (Millipore), neutralized by 20 µl 1M NaOH, and stored at −80° C. before HPLC analysis. Control reactions without enzymes were run at the same time. The TE hydrolysis reaction was measured by consumption of CoA substrates. The HPLC peak areas of CoA substrates were normalized based on the internal standards.

ST and TE Assays Using ACP-Linked Substrates

The ST and TE assays were performed using R)-1-ACP and (3S)-1-ACP substrates. Typically, for the ST reactions, about 300 µM ACP-linked substrate was added with 2 µM ST and 2 mM PAPS in 50 mM Tris-HCl buffer (pH 7.0). For the TE reactions, about 300 µM ACP-linked substrate was added with 2 µM TE in 50 mM Tris-HCl buffer (pH 7.0). All the reactions were incubated at room temperature, quenched by addition of 10% formic acid, and analyzed by reverse-phase HPLC using Jupiter C4 column. The ACP fractions were collected, lyophilized and analyzed by FTICR-MS and IRMPD. To detect products cleaved from ACP by LC-MS, the reaction mixtures were filtered Microcon YM-10 to remove the enzymes. The samples were loaded onto XBridge C18 column (2.1×150 mm, 3.5 µm, Waters), and LC-MS analysis was performed on a Surveyor HPLC system equipped with a ESI-LTQ mass spectrometer (Thermo Scientific). For the coupled ST-TE reactions, the products were extracted with 2×2 ml hexane and dried under nitrogen prior to GC/MS analysis.

GC/EI-MS Analysis

The samples and authentic standard were analyzed by a 6890N gas chromatograph equipped with a 5973 mass selective quadrupole detector (Agilent). The butylamides were separated on a HP-5MS (Agilent J&W) capillary column (30 m×250 µm×0.25 µm), which was operated with helium-carrier gas and splitless injection. Both the injector and detector temperatures were set as 250° C. After an initial setting at 50° C., the oven temperature was raised to 300° C. at 6° C./min and held for 20 minutes. Total ion chromatograms were recorded using a mass range of 60-420 amu, and the selective ion chromatograms were recorded by monitoring the two to three most abundant masses plus the parent masses of target compounds.

Analysis of ACP Samples by Electrospray Ionization (ESI)-FTICR-MS

The observed and calculated masses for the ACP samples are listed in Table 4. Preparation of ACP samples for FTICR-MS analysis was performed as previously described in Gu, et al., *Science,* 318:970-974 (2007) All samples were analyzed with an actively shielded 7 Tesla quadrupole-FTICR mass spectrometer (APEX-Q, Bruker Daltonics). Target analytes in electrospray solution (1:1 $CH_3CN:H_2O$ with 0.1% HCOOH) were directly infused into an electrospray ionization (ESI) source (Apollo II, Bruker Daltonics) operating in positive ion mode at a flow rate of 70 µL/h and a voltage of −3.8 kV. A counterflow of hot (240° C.) nitrogen gas was applied to assist desolvation of ESI droplets. Multiply protonated ions generated by ESI were externally accumulated in a hexapole and transferred via high voltage ion optics to the ICR cell for analysis. For IRMPD, precursor ions were mass-selectively accumulated in the hexapole with a 5-10 m/z quadrupole isolation window, transferred to the ICR cell, and irradiated for 100-200 ms by 10.6 µm photons at 10 W laser power, (25 W $CO_2$ laser, Synrad). All data were acquired with XMASS software (version 6.1, Bruker Daltonics) in broad-band mode from m/z=200 to 2000 with 512 k data points and summed over 10-30 scans. Mass spectra were analyzed with the MIDAS analysis software. For accurate mass determination, ubiquitin (Sigma) peaks on charge state of 10-11 (ubiquitin was spiked into the ESI solution prior to analysis) was used as internal calibrants to determine the mass of apo-ACP. Once the exact mass of apo-ACP had been determined, its 11 and 13 charge states were selected as external standards for further calibration (ubiquitin was not spiked into all reactions). All frequency-to-m/z calibrations were performed with a two-term calibration equation.

TABLE 4

| $ACP_H$ samples | ESI-FTICR-MS | | IRMPD (PEP) | |
|---|---|---|---|---|
| | Obs. avg mass¶ | Calc. avg mass¶ | Obs. [M + H]⁺ | Calc. [M + H]⁺ |
| ACP-SH | 13786.92 | 13786.88 | 261.134 | 261.127 |
| 1-ACP | 14043.01 | 14043.08 | 517.349 | 517.331 |
| 2-ACP | 14122.99 | 14123.04 | 517.349* | 517.331* |

PEP, Phosphopantetheine ejection product.
¶The ACP species with the N-terminal methionine.
*A same PEP product was observed for 2-ACP and 1-ACP due to laser-induced dissociation of the sulfate group on 2-ACP.

Cloning, Site-Directed Mutagenesis, and Protein Expression

Inserts for CurM ACP (residues 1514-1592), ST (residues 1598-1917) and TE (residues 1929-2211) were generated by polymerase chain reaction amplification from the cosmid pLM14 (28). ACP and ST were inserted into pMCSG7 (29) and TE into pMoCR (30), containing the fusion Mocr to enhance solubility. All constructs were verified by DNA sequencing. The plasmids were transformed into BL21(DE3) E. coli cells and grown at 37° C. in 500 mL TB with 4% glycerol in 2 L baffle flasks until an $OD_{600}$ of 1.0. Trace metals (50 µM $FeCl_3$, 20 µM $CaCl_3$, 10 µM $MnCl_2$, 10 µM $ZnSO_4$, 2 µM $CoCl_2$, 2 µM $CuCl_2$, 2 µM $NiCl_2$, 2 µM $Na_2MoO_4$, 2 µM $Na_2SeO_3$, 2 µM $H_3BO_3$) were added when growing the ACP. The temperature was lowered to 18° C. and IPTG was added to a final concentration of 0.2 mM. The culture grew for an additional 18 hours, the cells were harvested by centrifugation, and frozen at −20° C. Selenomethionyl (SeMet) protein was produce in BL21(DE3) in SelenoMet™ Medium (AthenaES) containing 100 µg/mL seleno-DL-methionine. Site directed mutagenesis was performed using the QuickChange protocol (Stratagene) and confirmed by DNA sequencing.

Protein Purification

Performing all steps at 4° C. unless noted, the cell pellet from 500 mL of cell culture was re-suspended in 40 mL Buffer A (20 mM Tris pH 7.9, 500 mM NaCl, 20 mM imidazole, and 10% glycerol). DNase (2 mg), lysozyme (5 mg), and $MgCl_2$ (4 mM final concentration) were added and incubated for 30 min. The cells were lysed by sonication and the lysate cleared by centrifugation. The supernatant was filtered through 0.45 µm filters and loaded onto a 5 mL HisTrap Ni NTA resin column (GE Healthcare). The column was washed with 8 column volumes Buffer A. The proteins eluted around 150 mM imidazole by a linear gradient up to 650 mM imidazole (Buffer B). The 6× His-Mocr fusion on the TE was removed by incubating the pooled fractions with 1 mM DTT and 2% (w/w) tobacco etch virus (TEV) protease for two hours at room temperature. The imidazole was removed by dialysis overnight at 4° C. in Buffer C (20 mM Tris pH 7.9, 500 mM NaCl, 10% glycerol) with 1 mM DTT. The reaction mixture was loaded again on the HisTrap column and the flow-through fractions were collected and pooled. All proteins were further purified by size exclusion chromatography with a HiLoad 16/60 Superdex 200 (GE Healthcare) pre-equilibrated with Buffer C. Fractions were pooled and concentrated to 5 mg/mL, flash frozen in liquid $N_2$, and stored at −80° C. The SeMet derivative of the TE was purified as described above with 2 mM DTT added to all buffers. 500 mL of culture yielded 5 mg of purified TE, 2 mg of SeMet TE, 10 mg of ACP, and 20 mg of ST.

Crystallization

Crystals of CurM TE were grown at 4° C. within 24-48 hours in hanging drops using the vapor diffusion method. Protein solution containing 2 mg/mL protein, 20 mM Tris pH 7.9, 200 mM NaCl and 2.5% glycerol was mixed in equal volumes with well solution containing 27-32% PEG3350, 100 mM Tris pH 8.3-8.5. Micro-seeding from native crystals was required for crystal growth of the SeMet protein in similar conditions. Crystals were transferred into cryo protection solution containing well solution with 15% glycerol, harvested in loops and flash frozen in liquid $N_2$.

Data Collection and Structure Determination

Data were collected at GM/CA-CAT beamline 23ID-D at the Advanced Photon Source (APS) at Argonne National Lab (Argonne, Ill.). Among 25 SeMet TE crystals, only one diffracted beyond 4 Å, but had multiple lattices in the diffraction and two distinct crystals. A region visually identified as a single crystal was probed in three 10-µm steps using a 20-µm mini-beam (31). The center position was chosen for the best diffraction with the least interference from the second lattice, and data were collected in inverse-beam geometry ($\phi=0°$-$90°$ and $180°$-$270°$ as wedges of $45°$ with $1°$ images). The diffraction images showed significant radiation damage, so a different region of the sample was probed in a perpendicular orientation. The crystal was rotate $90°$ from the initial raster and now looking into the loop, visual identification of a region with a single crystal was impossible. Two separate regions in this orientation were rastered in 3 by 3 boxes in steps of 10-µm with the 10-µm collimator. From these rasters, a single lattice position was identified where data were collected again in inverse beam geometry ($\phi=90°$-$150°$ and $270°$-$330°$ as $30°$ wedges with $0.5°$ images). The two partial datasets were indexed separately resulting in similar unit cell constants and scaled together, all using the HKL2000 suite (32), to yield a complete SAD dataset. The SeMet TE structure was solved using SOLVE/RESOLVE (33, 34) in the PHENIX software suite. 28 Se sites were found (average figure of merit (FOM) =0.401). After density modification and fourfold noncrystallographic symmetry averaging in RESOLVE the figure of merit was 0.81. AUTOBUILD (35) was used to build an 86% complete initial model, which was completed manually in COOT (36). REFMAC5, from the CCP4 suite, was used for refinement with TLS (37-39).

Sequence Alignment, Structure Alignment and Substrate Modeling

Similar ACP-ST-TE sequences were identified by a BLAST search into the NCBI protein database. ClustalW was used to perform the multiple sequence alignment (40). Pymol was used to align structures and to prepare structure illustrations (41). CurM TE was aligned with affinity labeled PikTE (PDB code 2H7X, RMS=3.309) by superposition of the core domains (residues 55-176 and 232-292 in PikTE to residues 1-126 and 217-282 in CurTE). The PRODRG2 server (42) was used to generate initial atomic coordinates and a topology file for the predicted tetrahedral intermediate. The intermediate was modeled using the affinity label in the active site of PikTE (PDB code 2H7X) (25, 26) as a guide.

Preparation of Substrate-Loaded ACP

The substrate-loaded ACP was prepared by loading 3-hydroxy-5-methoxytetradecanoyl-CoA (28) onto the apo ACP using S. verticillus Svp(43). 50 µM ACP and 100 µM 3-hydroxy-5-methoxytetradecanoyl-CoA were incubated with 10 µM Svp and 10 mM $MgCl_2$ in 100 mM Tris pH 7.9 at 30° C. for 2 hours. The reaction was exchanged into Buffer C, concentrated to 550 µM ACP using Amicon Ultra 10 kDa concentrators (Millipore), flash frozen in 20 µL aliquots, and stored at −80° C. Loading efficiency was analyzed by HPLC using the protocol described in the activity assay.

Activity Assay

TE activity was assayed using a modification of the protocol developed by Gu et. al. (28). To generate the sulfated substrate for the TE assay, 225 µM loaded ACP was incubated with 5 µM ST, 1.75 mM PAPS (Sigma), in 100 mM Tris pH 7.9 at room temperature for 10 min. Four µM TE was then added to the mixture and the reaction was quenched with 10% formic acid after 1 min. The samples were analyzed by reverse phase HPLC using a Jupiter C4 column (250×2.0 mm, 5 µm, 300 Å, Phenomenex) and a linear elution gradient from 30% to 90% $CH_3CN$ (0.1% $CF_3CO_2H$)/$H_2O$ (0.1% $CF_3CO_2H$) over 45 min.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

REFERENCES

1. Gu, et al., *Science* 318, 970-974 (2007).
2. Fischbach et al., *Proc. Natl Acad Sci. USA*, 105, 4601-4608 (2008).
3. Gu, et al. *Nature* 459, 731-735 (2009).
4. Verdier-Pinard P. et al. *Molecular Pharmacology* 53, 62-76 (1998).
5. Chang et al., *J Nat Prod* 67, 1356-1367 (2004).
6. Gu et al., *J Am Chem Soc* 128, 9014-9015 (2006).
7. Calderone et al., *Chemistry & Biology* 14, 835-846 (2007).
8. Calderone et al., *Proc. Natl Acad Sci. USA* 103, 8977-8982 (2006).
9. Walsh *Accounts of Chemical Research* 41, 4-10 (2008).
10. Chapman et al *Angew Chem-International Edition* 43, 3526-3548 (2004).
11. Walsh C T *Science* 303, 1805-1810 (2004).
12. Fischbach et al., *Chemical Reviews* 106, 3468-3496 (2006).
13. Khosla et al., *The annual review of biochemistry* 76, 11.11-11.27 (2007).
14. Chang et al., *Gene* 296, 235-247 (2002).
15. Sanchez et al., *Chemistry & Biology* 8, 725-738 (2001).
16. Dorrestein et al., *Biochemistry* 45, 12756-12766 (2006).
17. Caffrey *Chemistry & Biology* 12, 1060-1062 (2005).
18. Bonanno et al. *Proc. Natl Acad Sci. USA* 98, 12896-12901 (2001).
19. Choi et al., *Microbiology-Sgm* 153, 1095-1102 (2007).
20. Senko et al, *Rapid Commun. Mass Spectrom.* 10, 1839-1844 (1996).
21. Ledford et al, *Anal. Chem.* 56, 2744-2748 (1984).
22. Geders, et al., *J Biol Chem*, 2007. 282(49): p. 35954-63.
23. Akey, et al., *Structure*, 2010. 18(1): p. 94-105.
24. Roongsawang, et al., *Chembiochem*, 2007. 8(5): p. 501-12.
25. Giraldes, et al., *Nat Chem Biol*, 2006. 2(10): p. 531-6.
26. Akey, et al., *Nat Chem Biol*, 2006. 2(10): p. 537-42.
27. Tsai, et al., *Proc Natl Acad Sci USA*, 2001. 98(26): p. 14808-13.
28. Gu, et al., *J Am Chem Soc*, 2009. 131(44): p. 16033-5.
29. Donnelly, et al., *Protein Expr Purif*, 2006. 47(2): p. 446-54.
30. DelProposto, et al., *Protein Expr Purif*, 2009. 63(1): p. 40-9.
31. Fischetti, et al., *J Synchrotron Radiat*, 2009. 16(Pt 2): p. 217-25.
32. Otwinowski, *Processing of X-ray Diffraction Data Collected in Oscillation Mode Methods in Enzymology*, 1997. 276(Macromolecular Crystallography, part A,): p. 307-326.
33. Terwilliger, et al., *Acta Crystallogr D Biol Oystallogr*, 1999. 55(Pt 4): p. 849-61.
34. Terwilliger, *Acta Crystallogr D Biol Crystallogr*, 2000. 56(Pt 8): p. 965-72.
35. Terwilliger, *Acta Crystallogr D Biol Crystallogr*, 2003. 59(Pt 1): p. 38-44.
36. Emsley, et al., *Acta Crystallogr D Biol Crystallogr*, 2004. 60(Pt 12 Pt 1): P. 2126-32.
37. The CCP4 suite: programs for protein crystallography. *Acta Crystallogr D Biol Oystallogr*, 1994. 50(Pt 5): p. 760-3.
38. Murshudov, et al., *Acta Crystallogr D Biol Crystallogr*, 1997. 53(Pt 3): p. 240-55.
39. Painter, et al., *Acta Crystallogr D Biol Oystallogr*, 2006. 62(Pt 4): p. 439-50.
40. Thompson, et al., *Curr Protoc Bioinformatics*, 2002. Chapter 2: p. Unit 23.
41. DeLano, *The PyMOL Molecular Graphics System*. In. 2002, DeLano Scientific: Palo Alto, Calif., USA.
42. Schuttelkopf, et al., *Acta Crystallogr D Biol Crystallogr*, 2004. 60(Pt 8): p. 1355-63.
43. Sanchez, et al., *Chem Biol*, 2001. 8(7): p. 725-38.
44. Chan Young, et al., *New Journal of Chemistry*, 1986. 10(12): p. 701-707.

What is claimed:

1. A method for producing an alkene comprising:

(i) contacting a beta-hydroxy carboxylic acid or carboxylic acid derivative with a sulfonating reagent and a sulfotransferase (ST) under conditions that the ST mediates the formation of a beta-sulfate carboxylic acid or carboxylic acid derivative; and, (ii) contacting the beta-sulfate carboxylic acid or carboxylic acid derivative with a thioesterase (TE) under conditions that the TE mediates decarboxylative elimination of the beta-sulfate carboxylic acid or carboxylic acid derivative to form the alkene;

wherein the ST and TE are tandem domains in the same polypeptide.

2. The method of claim 1, wherein the TE comprises an amino acid sequence that is at least 95% identical to SEQ ID NO: 3 or an enzymatically active fragment thereof which maintains the TE activity of SEQ ID NO: 3.

3. The method of claim 1, wherein the ST comprises SEQ ID NO: 4, or an enzymatically active fragment thereof which maintains the ST activity of SEQ ID NO: 4.

4. The method of claim 1, wherein the carboxylic acid derivative comprises the carboxylic acid conjugated to an acyl carrier protein (ACP).

5. The method of claim 4, wherein the ACP comprises the amino acid sequence set out in SEQ ID NO: 5 or active fragment thereof.

6. The method of claim 4, wherein the ACP is in a separate peptide from the ST and TE.

7. The method of claim 4, wherein each of the ACP, ST and TE are in the same polypeptide.

8. The method of claim 7, wherein the polypeptide has the sequence of SEQ ID NO: 1.

9. The method of claim 1, wherein the alkene is a terminal alkene.

10. The method of claim 9, wherein the alkene has a structure of formula (II) and the beta-sulfate or beta-hydroxy carboxylic acid or carboxylic acid derivative has a structure of formula (I):

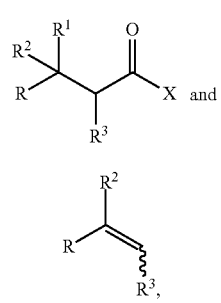

wherein R is alkyl, heteroalkyl, cycloalkyl, aryl, heteroaryl, heterocycloalkyl, alkenyl, or alkynyl and can be optionally substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

$R^2$ and $R^3$ are each independently selected from the group consisting of hydrogen, alkyl, heteroalkyl, cycloalkyl, aryl, heteroaryl, heterocycloalkyl, alkenyl, or alkynyl and can be optionally substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

X is OH, SH, $OR^2$, or $SR^2$;

$R^1$ is hydroxy or sulfate; and $R^2$ is optionally substituted alkyl, optionally substituted alkenyl, or a peptide.

11. The method of claim 10, wherein the peptide of $R^2$ comprises ACP.

12. A method for producing an alkene comprising:
(i) contacting a beta-hydroxy carboxylic acid or carboxylic acid derivative with a sulfonating reagent and a sulfotransferase (ST), wherein the ST comprises SEQ ID NO: 4, or an enzymatically active fragment thereof which maintains the ST activity of SEQ ID NO: 4, under conditions that the ST mediates the formation of a beta-sulfate carboxylic acid or carboxylic acid derivative; and,
(ii) contacting the beta-sulfate carboxylic acid or carboxylic acid derivative with a thioesterase (TE), wherein the TE comprises an amino acid sequence that is at least 95% identical to SEQ ID NO: 3, or an enzymatically active fragment thereof which maintains the TE activity of SEQ ID NO: 3, under conditions that the TE mediates decarboxylative elimination of the beta-sulfate carboxylic acid or carboxylic acid derivative to form the alkene;
wherein the ST and TE are in separate polypeptides.

13. The method of claim 12, wherein the carboxylic acid derivative comprises the carboxylic acid conjugated to an acyl carrier protein (ACP).

14. The method of claim 13, wherein the ACP comprises the amino acid sequence of SEQ ID NO: 5 or active fragment thereof.

15. The method of claim 13, wherein the ACP is in the same polypeptide as either the ST or the TE.

16. The method of claim 13, wherein each of the ACP, ST, and TE are in separate polypeptides.

17. The method of claim 12, wherein the alkene is a terminal alkene.

18. The method of claim 17, wherein the alkene has a structure of formula (II) and the beta-sulfate or beta-hydroxy carboxylic acid or carboxylic acid derivative has a structure of formula (I):

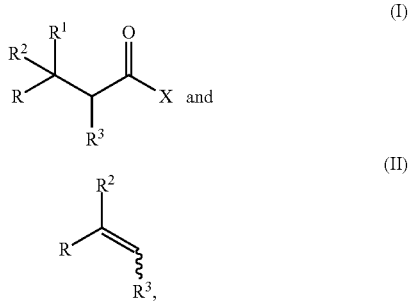

wherein R is alkyl, heteroalkyl, cycloalkyl, aryl, heteroaryl, heterocycloalkyl, alkenyl, or alkynyl and can be optionally substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

$R^2$ and $R^3$ are each independently selected from the group consisting of hydrogen, alkyl, heteroalkyl, cycloalkyl, aryl, heteroaryl, heterocycloalkyl, alkenyl, or alkynyl and can be optionally substituted with one or more of halo, alkyl, heteroalkyl, alkenyl, cycloalkyl, aryl, heteroaryl, heterocycloalkyl, nitro, cyano, amino, alkoxy, carboxy, carboxyalkyl, amido, thiol, hydroxy, and thioether;

X is OH, SH, $OR^2$, or $SR^2$;

$R^1$ is hydroxy or sulfate; and $R^2$ is optionally substituted alkyl, optionally substituted alkenyl, or a peptide.

19. The method of claim 18, wherein the peptide of $R^2$ comprises ACP.

* * * * *